US012751822B2

(12) United States Patent
Arcaro et al.

(10) Patent No.: US 12,751,822 B2
(45) Date of Patent: Oct. 6, 2026

(54) TAPERED HEART VALVE COVERING

(71) Applicant: EDWARDS LIFESCIENCES CORPORATION, Irvine, CA (US)

(72) Inventors: David J. Arcaro, Flagstaff, AZ (US); Kyle W. Colavito, Flagstaff, AZ (US); Dustin V. Dienno, Flagstaff, AZ (US); Cody L. Hartman, Flagstaff, AZ (US); Roy Manygoats, Jr., Flagstaff, AZ (US); Ryan S. Titone, Flagstaff, AZ (US); Ryan D. Smith, Flagstaff, AZ (US); Joshua A. Sprinkle, Flagstaff, AZ (US); Benjamin A. Smith, Flagstaff, AZ (US); James L. Goepfrich, Flagstaff, AZ (US); Michael J. Shepard, Flagstaff, AZ (US)

(73) Assignee: Edwards Lifesciences Corporation, Irvine, CA (US)

( * ) Notice: Subject to any disclaimer, the term of this patent is extended or adjusted under 35 U.S.C. 154(b) by 212 days.

(21) Appl. No.: 18/653,820

(22) Filed: May 2, 2024

(65) Prior Publication Data

US 2024/0277472 A1 Aug. 22, 2024

Related U.S. Application Data

(63) Continuation of application No. 17/476,867, filed on Sep. 16, 2021, now Pat. No. 11,974,916, which is a (Continued)

(51) Int. Cl.

*A61F 2/24* (2006.01)
*A61L 27/16* (2006.01)
(Continued)

(52) U.S. Cl.

CPC .......... *A61F 2/2418* (2013.01); *A61F 2/2409* (2013.01); *A61F 2/2412* (2013.01); (Continued)

(58) Field of Classification Search

CPC ............ A61F 2/24–2418; A61F 2/2475; A61F 2250/0036; A61F 2250/006–0064; A61F 2220/0033

See application file for complete search history.

(56) References Cited

U.S. PATENT DOCUMENTS

| | | | |
|---|---|---|---|
| 654,799 | A | 7/1900 | Levett |
| 3,953,566 | A | 4/1976 | Gore |

(Continued)

FOREIGN PATENT DOCUMENTS

| | | | |
|---|---|---|---|
| AU | 2013363172 | A1 | 7/2015 |
| AU | 2017202405 | A1 | 4/2017 |

(Continued)

OTHER PUBLICATIONS

Cardiac Surgery in the Adult, Third Edition, Chapter Feb. 2008.

(Continued)

*Primary Examiner* — Rebecca S Preston
(74) *Attorney, Agent, or Firm* — Chang & Hale LLP

(57) ABSTRACT

A covering for a prosthetic valve comprises a first portion configured to couple to an outflow side of a prosthetic valve and a second portion configured to couple to an inflow side of the prosthetic valve. The first portion is annular in shape and has a first edge alternating between one or more first tips and one or more first valleys. The second portion is also annular in shape and has a second edge alternating between one or more second tips and one or more second valleys. The one or more second tips are configured to couple to the one (Continued)

or more first tips to at least partially cover posts of the prosthetic valve. The one or more second tips have a tapered form.

16 Claims, 28 Drawing Sheets

Related U.S. Application Data continuation of application No. 16/129,677, filed on Sep. 12, 2018, now Pat. No. 11,154,397.

(60) Provisional application No. 62/667,181, filed on May 4, 2018, provisional application No. 62/579,754, filed on Oct. 31, 2017.

(51) Int. Cl.
*A61L 27/18* (2006.01)
*A61L 27/28* (2006.01)
*A61L 27/56* (2006.01)

(52) U.S. Cl.
CPC ........... *A61F 2/2415* (2013.01); *A61F 2/2427* (2013.01); *A61F 2210/0076* (2013.01); *A61F 2220/0008* (2013.01); *A61F 2220/0033* (2013.01); *A61F 2220/0041* (2013.01); *A61F 2220/005* (2013.01); *A61F 2220/0075* (2013.01); *A61F 2230/0069* (2013.01); *A61F 2250/0051* (2013.01); *A61F 2250/006* (2013.01); *A61F 2250/0069* (2013.01); *A61L 27/16* (2013.01); *A61L 27/18* (2013.01); *A61L 27/28* (2013.01); *A61L 27/56* (2013.01)

(56) References Cited

U.S. PATENT DOCUMENTS 4,178,639 A 12/1979 Bokros
4,222,126 A 9/1980 Boretos et al.
4,265,694 A 5/1981 Boretos et al.
4,340,091 A 7/1982 Skelton et al.
4,477,930 A 10/1984 Totten et al.
4,556,996 A 12/1985 Wallace
4,626,255 A 12/1986 Reichart et al.
4,759,759 A 7/1988 Walker et al.
4,851,000 A 7/1989 Gupta
5,123,918 A 6/1992 Perrier et al.
5,163,955 A 11/1992 Love et al.
5,415,667 A 5/1995 Frater
5,469,868 A 11/1995 Reger
5,489,297 A 2/1996 Duran
5,554,183 A 9/1996 Nazari
5,554,185 A 9/1996 Block et al.
5,562,729 A 10/1996 Purdy et al.
5,628,791 A 5/1997 Bokros et al.
5,708,044 A 1/1998 Branca
5,928,281 A 7/1999 Huynh et al.
5,935,163 A 8/1999 Gabbay
5,944,654 A 8/1999 Crawford
6,019,785 A 2/2000 Strecker
6,086,612 A 7/2000 Jansen
6,117,169 A 9/2000 Moe
6,129,758 A 10/2000 Love
6,171,335 B1 1/2001 Wheatley et al.
6,174,331 B1 1/2001 Moe et al.
6,197,143 B1 3/2001 Bodnar
6,283,994 B1 9/2001 Moe et al.
6,283,995 B1 9/2001 Moe et al.
6,287,334 B1 9/2001 Moll et al.
6,328,763 B1 12/2001 Love et al.
6,334,873 B1 * 1/2002 Lane .................... A61F 2/2412
623/2.14
6,454,798 B1 9/2002 Moe
6,454,799 B1 9/2002 Schreck
6,461,382 B1 10/2002 Cao
6,482,228 B1 11/2002 Norred
6,541,589 B1 4/2003 Baillie
6,558,418 B2 5/2003 Carpentier et al.
6,562,069 B2 5/2003 Cai et al.
6,582,464 B2 6/2003 Gabbay
6,613,086 B1 9/2003 Moe et al.
6,645,244 B2 11/2003 Shu et al.
6,666,885 B2 12/2003 Moe
6,726,715 B2 4/2004 Sutherland
6,730,118 B2 5/2004 Spenser et al.
6,755,857 B2 6/2004 Peterson et al.
6,893,460 B2 5/2005 Spenser et al.
6,916,338 B2 7/2005 Speziali
6,936,067 B2 8/2005 Buchanan
6,953,332 B1 10/2005 Kurk et al.
7,137,184 B2 11/2006 Schreck
7,163,556 B2 1/2007 Xie et al.
7,238,200 B2 7/2007 Lee et al.
7,247,167 B2 7/2007 Gabbay
7,306,729 B2 12/2007 Bacino et al.
7,381,218 B2 6/2008 Schreck
7,462,675 B2 12/2008 Chang et al.
7,510,575 B2 3/2009 Spenser et al.
7,513,909 B2 4/2009 Lane et al.
7,531,611 B2 5/2009 Sabol et al.
7,563,277 B2 7/2009 Case et al.
7,708,775 B2 5/2010 Rowe et al.
7,727,274 B2 6/2010 Zilla et al.
7,758,640 B2 7/2010 Vesely
7,780,725 B2 8/2010 Haug et al.
7,803,186 B1 9/2010 Li et al.
7,879,085 B2 2/2011 Sowinski et al.
7,914,569 B2 3/2011 Nguyen et al.
7,967,853 B2 6/2011 Eidenschink et al.
7,993,394 B2 8/2011 Hariton et al.
8,062,359 B2 11/2011 Marquez et al.
8,092,523 B2 1/2012 Li et al.
8,167,935 B2 5/2012 McGuckin, Jr. et al.
8,226,710 B2 7/2012 Nguyen et al.
8,246,678 B2 8/2012 Salahieh et al.
8,252,037 B2 8/2012 Styrc et al.
8,303,647 B2 11/2012 Case
8,349,000 B2 1/2013 Schreck
8,409,274 B2 4/2013 Li et al.
8,475,512 B2 7/2013 Hunt
8,568,475 B2 10/2013 Nguyen et al.
8,585,757 B2 11/2013 Agathos
8,628,566 B2 1/2014 Eberhardt et al.
8,637,144 B2 1/2014 Ford
8,709,077 B2 4/2014 Schreck
8,722,178 B2 5/2014 Ashmead et al.
8,728,154 B2 5/2014 Alkhatib
8,784,481 B2 7/2014 Alkhatib et al.
8,808,848 B2 8/2014 Bacino
8,845,709 B2 9/2014 Styrc et al.
8,845,721 B2 9/2014 Braido et al.
8,852,272 B2 10/2014 Gross et al.
8,870,948 B1 10/2014 Erzberger et al.
8,945,212 B2 2/2015 Bruchman et al.
8,961,599 B2 2/2015 Bruchman et al.
8,992,608 B2 3/2015 Haug et al.
9,101,469 B2 8/2015 Bruchman et al.
9,107,771 B2 8/2015 Wubbeling et al.
9,125,740 B2 9/2015 Morriss et al.
9,139,669 B2 9/2015 Xu et al.
9,144,492 B2 9/2015 Bruchman et al.
9,168,131 B2 10/2015 Yohanan et al.
9,198,787 B2 12/2015 Kratzberg et al.
9,283,072 B2 3/2016 Bruchman et al.
9,314,355 B2 4/2016 Styrc et al.
9,375,308 B2 6/2016 Norris
9,393,110 B2 7/2016 Levi et al.
9,398,952 B2 7/2016 Bruchman et al.
9,504,565 B2 11/2016 Armstrong
9,554,900 B2 1/2017 Bruchman et al.
9,597,181 B2 3/2017 Christianson et al.
9,629,718 B2 4/2017 Gloss et al.

(56) References Cited

U.S. PATENT DOCUMENTS

| | | | |
|---|---|---|---|
| 9,737,398 | B2 | 8/2017 | Bruchman et al. |
| 9,743,932 | B2 | 8/2017 | Amplatz et al. |
| 9,801,712 | B2 | 10/2017 | Bruchman et al. |
| 9,827,089 | B2 | 11/2017 | Bruchman et al. |
| 9,827,094 | B2 | 11/2017 | Bennett |
| 9,855,141 | B2 | 1/2018 | Dienno et al. |
| 9,931,204 | B2 | 4/2018 | Rothstein et al. |
| 9,937,037 | B2 | 4/2018 | Dienno et al. |
| 9,968,443 | B2 | 5/2018 | Bruchman et al. |
| 10,039,638 | B2 | 8/2018 | Bruchman et al. |
| 10,285,808 | B2 | 5/2019 | Bruchman et al. |
| 10,314,697 | B2 | 6/2019 | Gassler |
| 10,321,986 | B2 | 6/2019 | Bruchman et al. |
| 10,342,659 | B2 | 7/2019 | Bennett |
| 10,368,984 | B2 | 8/2019 | Armstrong |
| 10,376,360 | B2 | 8/2019 | Bruchman et al. |
| 10,441,416 | B2 | 10/2019 | Oba et al. |
| 10,463,478 | B2 | 11/2019 | Bruchman et al. |
| 10,639,144 | B2 | 5/2020 | Bruchman et al. |
| 10,660,745 | B2 | 5/2020 | Bruchman et al. |
| 10,881,507 | B2 | 1/2021 | Bruchman et al. |
| 10,980,633 | B2 | 4/2021 | Dienno et al. |
| 11,020,221 | B2 | 6/2021 | Arcaro et al. |
| 11,039,917 | B2 | 6/2021 | Bruchman et al. |
| D926,322 | S | 7/2021 | Bennett et al. |
| 11,065,112 | B2 | 7/2021 | Gassler |
| 11,090,153 | B2 | 8/2021 | Haarer et al. |
| 11,109,963 | B2 | 9/2021 | Dienno et al. |
| 11,123,183 | B2 | 9/2021 | Bennett et al. |
| 2002/0045936 | A1 | 4/2002 | Moe |
| 2002/0055773 | A1 | 5/2002 | Campbell et al. |
| 2002/0082687 | A1 | 6/2002 | Moe |
| 2002/0133226 | A1 | 9/2002 | Marquez et al. |
| 2002/0183840 | A1 | 12/2002 | Lapeyre et al. |
| 2002/0198594 | A1 | 12/2002 | Schreck |
| 2003/0014105 | A1 | 1/2003 | Cao |
| 2003/0027332 | A1 | 2/2003 | Lafrance et al. |
| 2003/0055496 | A1 | 3/2003 | Cai et al. |
| 2003/0074052 | A1 | 4/2003 | Besselink |
| 2003/0097175 | A1 | 5/2003 | O'Connor et al. |
| 2003/0114913 | A1 | 6/2003 | Spenser et al. |
| 2003/0229394 | A1 | 12/2003 | Ogle et al. |
| 2004/0024448 | A1 | 2/2004 | Chang et al. |
| 2004/0024451 | A1 | 2/2004 | Johnson et al. |
| 2004/0026245 | A1 | 2/2004 | Agarwal et al. |
| 2004/0039436 | A1 | 2/2004 | Spenser et al. |
| 2004/0176839 | A1 | 9/2004 | Huynh et al. |
| 2004/0243222 | A1 | 12/2004 | Osborne et al. |
| 2004/0260393 | A1 | 12/2004 | Rahdert et al. |
| 2005/0027348 | A1 | 2/2005 | Case et al. |
| 2005/0119722 | A1 | 6/2005 | Styrc et al. |
| 2005/0137682 | A1 | 6/2005 | Justino |
| 2005/0261765 | A1 | 11/2005 | Liddicoat |
| 2006/0008497 | A1 | 1/2006 | Gabbay |
| 2006/0041091 | A1 | 2/2006 | Chang et al. |
| 2006/0122693 | A1 | 6/2006 | Biadillah et al. |
| 2006/0154365 | A1 | 7/2006 | Ratcliffe et al. |
| 2006/0229718 | A1 | 10/2006 | Marquez |
| 2006/0229719 | A1 | 10/2006 | Marquez et al. |
| 2006/0259136 | A1 | 11/2006 | Nguyen et al. |
| 2006/0265053 | A1 | 11/2006 | Hunt |
| 2006/0276813 | A1 | 12/2006 | Greenberg |
| 2006/0276888 | A1 | 12/2006 | Lee et al. |
| 2006/0282162 | A1 | 12/2006 | Nguyen et al. |
| 2006/0290027 | A1 | 12/2006 | O'Connor et al. |
| 2007/0010876 | A1 | 1/2007 | Salahieh et al. |
| 2007/0021826 | A1 | 1/2007 | Case et al. |
| 2007/0118210 | A1 | 5/2007 | Pinchuk |
| 2007/0207186 | A1 | 9/2007 | Scanlon et al. |
| 2007/0244552 | A1 | 10/2007 | Salahieh et al. |
| 2008/0009940 | A1 | 1/2008 | Cribier |
| 2008/0026190 | A1 | 1/2008 | King et al. |
| 2008/0039934 | A1 | 2/2008 | Styrc |
| 2008/0065198 | A1 | 3/2008 | Quintessenza |
| 2008/0071369 | A1 | 3/2008 | Tuval et al. |
| 2008/0082154 | A1 | 4/2008 | Tseng et al. |
| 2008/0133004 | A1 | 6/2008 | White |
| 2008/0140178 | A1 | 6/2008 | Rasmussen et al. |
| 2008/0195199 | A1 | 8/2008 | Kheradvar et al. |
| 2008/0208327 | A1 | 8/2008 | Rowe |
| 2008/0220041 | A1 | 9/2008 | Brito et al. |
| 2008/0228263 | A1 | 9/2008 | Ryan |
| 2008/0294248 | A1 | 11/2008 | Yang et al. |
| 2008/0300678 | A1 | 12/2008 | Eidenschink et al. |
| 2009/0117334 | A1 | 5/2009 | Sogard et al. |
| 2009/0138079 | A1 | 5/2009 | Tuval et al. |
| 2009/0157175 | A1 | 6/2009 | Benichou |
| 2009/0240320 | A1 | 9/2009 | Tuval et al. |
| 2009/0264997 | A1 | 10/2009 | Salahieh et al. |
| 2009/0276039 | A1 | 11/2009 | Meretei |
| 2009/0287305 | A1 | 11/2009 | Amalaha |
| 2009/0292350 | A1 | 11/2009 | Eberhardt et al. |
| 2010/0023114 | A1 | 1/2010 | Chambers et al. |
| 2010/0036021 | A1 | 2/2010 | Lee et al. |
| 2010/0036484 | A1 | 2/2010 | Hariton et al. |
| 2010/0049294 | A1 | 2/2010 | Zukowski et al. |
| 2010/0082094 | A1 | 4/2010 | Quadri et al. |
| 2010/0131056 | A1 | 5/2010 | Lapeyre |
| 2010/0137998 | A1 | 6/2010 | Sobrino-Serrano et al. |
| 2010/0145438 | A1 | 6/2010 | Barone |
| 2010/0168839 | A1 | 7/2010 | Braido et al. |
| 2010/0185274 | A1 | 7/2010 | Moaddeb et al. |
| 2010/0185277 | A1 | 7/2010 | Braido et al. |
| 2010/0191320 | A1 | 7/2010 | Straubinger et al. |
| 2010/0204781 | A1 | 8/2010 | Alkhatib |
| 2010/0204785 | A1 | 8/2010 | Alkhatib |
| 2010/0211165 | A1 | 8/2010 | Schreck |
| 2010/0217382 | A1 | 8/2010 | Chau et al. |
| 2010/0248324 | A1 | 9/2010 | Xu et al. |
| 2010/0249923 | A1 | 9/2010 | Alkhatib et al. |
| 2010/0262231 | A1 | 10/2010 | Tuval et al. |
| 2010/0298931 | A1 | 11/2010 | Quadri et al. |
| 2011/0040366 | A1 | 2/2011 | Goetz et al. |
| 2011/0054515 | A1 | 3/2011 | Bridgeman et al. |
| 2011/0064781 | A1 | 3/2011 | Cleek et al. |
| 2011/0160836 | A1 | 6/2011 | Behan |
| 2011/0172784 | A1 | 7/2011 | Richter et al. |
| 2011/0208283 | A1 | 8/2011 | Rust |
| 2011/0218619 | A1 | 9/2011 | Benichou et al. |
| 2011/0251678 | A1 | 10/2011 | Eidenschink et al. |
| 2011/0257739 | A1 | 10/2011 | Corbett |
| 2011/0282439 | A1 | 11/2011 | Thill et al. |
| 2011/0295363 | A1 | 12/2011 | Girard et al. |
| 2012/0035722 | A1 | 2/2012 | Tuval |
| 2012/0078357 | A1 | 3/2012 | Conklin |
| 2012/0083839 | A1 | 4/2012 | Letac et al. |
| 2012/0089223 | A1 | 4/2012 | Nguyen et al. |
| 2012/0101567 | A1 | 4/2012 | Jansen |
| 2012/0101571 | A1 | 4/2012 | Thambar et al. |
| 2012/0116496 | A1 | 5/2012 | Chuter et al. |
| 2012/0116498 | A1 | 5/2012 | Chuter et al. |
| 2012/0123529 | A1 | 5/2012 | Levi et al. |
| 2012/0123530 | A1 | 5/2012 | Carpentier et al. |
| 2012/0130468 | A1 | 5/2012 | Khosravi et al. |
| 2012/0130471 | A1 | 5/2012 | Shoemaker et al. |
| 2012/0185038 | A1 | 7/2012 | Fish et al. |
| 2012/0253453 | A1 | 10/2012 | Bruchman et al. |
| 2012/0290082 | A1 | 11/2012 | Quint et al. |
| 2012/0323315 | A1 | 12/2012 | Bruchman et al. |
| 2013/0018456 | A1 | 1/2013 | Li et al. |
| 2013/0079700 | A1 | 3/2013 | Ballard et al. |
| 2013/0110229 | A1 | 5/2013 | Bokeriya et al. |
| 2013/0116655 | A1 | 5/2013 | Bacino et al. |
| 2013/0150956 | A1 | 6/2013 | Yohanan et al. |
| 2013/0158647 | A1 | 6/2013 | Norris et al. |
| 2013/0166021 | A1 | 6/2013 | Bruchman et al. |
| 2013/0338755 | A1 | 12/2013 | Goetz et al. |
| 2014/0005771 | A1 | 1/2014 | Braido et al. |
| 2014/0005773 | A1 | 1/2014 | Wheatley |
| 2014/0031924 | A1 | 1/2014 | Bruchman et al. |
| 2014/0031927 | A1 | 1/2014 | Bruchman et al. |
| 2014/0094898 | A1 | 4/2014 | Borck |
| 2014/0106951 | A1 | 4/2014 | Brandon |
| 2014/0163671 | A1 | 6/2014 | Bruchman et al. |

(56) References Cited

U.S. PATENT DOCUMENTS

| | | | |
|---|---|---|---|
| 2014/0163673 | A1 | 6/2014 | Bruchman et al. |
| 2014/0172069 | A1 | 6/2014 | Roeder et al. |
| 2014/0172077 | A1 | 6/2014 | Bruchman et al. |
| 2014/0172078 | A1 | 6/2014 | Bruchman et al. |
| 2014/0172079 | A1 | 6/2014 | Bruchman et al. |
| 2014/0172082 | A1 | 6/2014 | Bruchman et al. |
| 2014/0172083 | A1 | 6/2014 | Bruchman et al. |
| 2014/0180400 | A1 | 6/2014 | Bruchman et al. |
| 2014/0194968 | A1 | 7/2014 | Zukowski |
| 2014/0222140 | A1 | 8/2014 | Schreck |
| 2014/0236289 | A1 | 8/2014 | Alkhatib |
| 2014/0277418 | A1 | 9/2014 | Miller |
| 2014/0296969 | A1 | 10/2014 | Tegels et al. |
| 2014/0324160 | A1 | 10/2014 | Benichou et al. |
| 2014/0324164 | A1 | 10/2014 | Gross et al. |
| 2014/0330368 | A1 | 11/2014 | Gloss et al. |
| 2014/0343670 | A1 | 11/2014 | Bakis et al. |
| 2015/0018944 | A1 | 1/2015 | O'Connell et al. |
| 2015/0088250 | A1 | 3/2015 | Zeng et al. |
| 2015/0105856 | A1 | 4/2015 | Rowe et al. |
| 2015/0142100 | A1 | 5/2015 | Morriss et al. |
| 2015/0157456 | A1 | 6/2015 | Armstrong |
| 2015/0224231 | A1 | 8/2015 | Bruchman et al. |
| 2015/0245910 | A1 | 9/2015 | Righini et al. |
| 2015/0366663 | A1 | 12/2015 | Bruchman et al. |
| 2015/0366664 | A1 | 12/2015 | Guttenberg et al. |
| 2016/0001469 | A1 | 1/2016 | Bacchereti et al. |
| 2016/0074161 | A1 | 3/2016 | Bennett |
| 2016/0113699 | A1 | 4/2016 | Sverdlik et al. |
| 2016/0157998 | A1 | 6/2016 | Bruchman et al. |
| 2016/0175095 | A1 | 6/2016 | Dienno et al. |
| 2016/0175096 | A1 | 6/2016 | Dienno et al. |
| 2016/0206424 | A1 | 7/2016 | Al-Jilaihawi et al. |
| 2016/0213465 | A1 | 7/2016 | Girard et al. |
| 2016/0235525 | A1 | 8/2016 | Rothstein et al. |
| 2016/0310268 | A1 | 10/2016 | Oba et al. |
| 2016/0317299 | A1 | 11/2016 | Alkhatib |
| 2017/0027727 | A1 | 2/2017 | Wuebbeling et al. |
| 2017/0042674 | A1 | 2/2017 | Armstrong |
| 2017/0056169 | A1 | 3/2017 | Johnson et al. |
| 2017/0095330 | A1 | 4/2017 | Malewicz et al. |
| 2017/0095331 | A1 | 4/2017 | Spenser et al. |
| 2017/0100236 | A1 | 4/2017 | Robertson et al. |
| 2017/0128199 | A1 | 5/2017 | Gurovich et al. |
| 2017/0156859 | A1 | 6/2017 | Chang et al. |
| 2017/0165066 | A1 | 6/2017 | Rothstein |
| 2017/0165067 | A1 | 6/2017 | Barajas-Torres et al. |
| 2017/0224481 | A1 | 8/2017 | Spenser et al. |
| 2017/0252153 | A1 | 9/2017 | Chau et al. |
| 2017/0348101 | A1 | 12/2017 | Vaughn et al. |
| 2018/0021128 | A1 | 1/2018 | Bruchman et al. |
| 2018/0125646 | A1 | 5/2018 | Bruchman et al. |
| 2018/0221144 | A1 | 8/2018 | Bruchman et al. |
| 2018/0318070 | A1 | 11/2018 | Bruchman et al. |
| 2019/0076245 | A1 | 3/2019 | Arcaro et al. |
| 2019/0091014 | A1 | 3/2019 | Arcaro et al. |
| 2019/0091015 | A1 | 3/2019 | Dienno et al. |
| 2019/0110893 | A1 | 4/2019 | Haarer et al. |
| 2019/0125528 | A1 | 5/2019 | Busalacchi et al. |
| 2019/0125530 | A1 | 5/2019 | Arcaro et al. |
| 2019/0125531 | A1 | 5/2019 | Bennett et al. |
| 2019/0125534 | A1 | 5/2019 | Arcaro et al. |
| 2019/0209292 | A1 | 7/2019 | Bruchman et al. |
| 2019/0247185 | A1 | 8/2019 | Gassler |
| 2019/0254815 | A1 | 8/2019 | Bruchman et al. |
| 2019/0269505 | A1 | 9/2019 | Bruchman et al. |
| 2019/0314154 | A1 | 10/2019 | Armstrong |
| 2019/0328525 | A1 | 10/2019 | Noe et al. |
| 2019/0374339 | A1 | 12/2019 | Bennett |
| 2020/0000578 | A1 | 1/2020 | Bruchman et al. |
| 2020/0237505 | A1 | 7/2020 | Bruchman et al. |
| 2020/0246137 | A1 | 8/2020 | Bruchman et al. |
| 2020/0276014 | A1 | 9/2020 | Burkart et al. |
| 2021/0121289 | A1 | 4/2021 | Bruchman et al. |
| 2021/0177589 | A1 | 6/2021 | Arcaro et al. |
| 2021/0205074 | A1 | 7/2021 | Bruchman et al. |
| 2021/0307905 | A1 | 10/2021 | Arcaro et al. |
| 2021/0338422 | A1 | 11/2021 | Dienno et al. |
| 2021/0346156 | A1 | 11/2021 | Haarer et al. |
| 2021/0361420 | A1 | 11/2021 | Bennett et al. |

FOREIGN PATENT DOCUMENTS

| | | | |
|---|---|---|---|
| CA | 2878691 | A1 | 1/2014 |
| CA | 2964546 | A1 | 1/2014 |
| CA | 2960034 | A1 | 3/2016 |
| CN | 101057796 | A | 10/2007 |
| CN | 101091675 | A | 12/2007 |
| CN | 101188985 | A | 5/2008 |
| CN | 101374477 | A | 2/2009 |
| CN | 101849863 | A | 10/2010 |
| CN | 101902989 | A | 12/2010 |
| CN | 102119013 | A | 7/2011 |
| CN | 102292053 | A | 12/2011 |
| CN | 102438546 | A | 5/2012 |
| CN | 102573703 | A | 7/2012 |
| CN | 102652694 | A | 9/2012 |
| CN | 102764169 | A | 11/2012 |
| CN | 102791223 | A | 11/2012 |
| CN | 102883684 | A | 1/2013 |
| CN | 103079498 | A | 5/2013 |
| CN | 103228232 | A | 7/2013 |
| CN | 103237524 | A | 8/2013 |
| CN | 103384505 | A | 11/2013 |
| CN | 103732183 | A | 4/2014 |
| CN | 103781439 | A | 5/2014 |
| CN | 104114127 | A | 10/2014 |
| CN | 104487023 | A | 4/2015 |
| CN | 104507417 | A | 4/2015 |
| CN | 105007955 | A | 10/2015 |
| CN | 105101911 | A | 11/2015 |
| CN | 105263445 | A | 1/2016 |
| CN | 105792780 | A | 7/2016 |
| CN | 106668949 | A | 5/2017 |
| CN | 106714733 | A | 5/2017 |
| CN | 106794065 | A | 5/2017 |
| CN | 107106294 | A | 8/2017 |
| DE | 212013000104 | U1 | 11/2014 |
| EP | 1235537 | A1 | 9/2002 |
| EP | 1318775 | A1 | 6/2003 |
| EP | 1395205 | A1 | 3/2004 |
| EP | 2109417 | A1 | 10/2009 |
| EP | 2193762 | A1 | 6/2010 |
| EP | 2359774 | A2 | 8/2011 |
| EP | 2400923 | A1 | 1/2012 |
| EP | 2591100 | A2 | 5/2013 |
| EP | 3142608 | A1 | 3/2017 |
| FR | 2591100 | A1 | 6/1987 |
| GB | 2312485 | A | 10/1997 |
| GB | 2513194 | A | 10/2014 |
| JP | 44032400 | | 12/1969 |
| JP | 1969032400 | | 12/1969 |
| JP | 10507097 | A | 7/1998 |
| JP | 2000511459 | A | 9/2000 |
| JP | 2000513248 | A | 10/2000 |
| JP | 2001508641 | A | 7/2001 |
| JP | 2001508681 | A | 7/2001 |
| JP | 2001511030 | A | 8/2001 |
| JP | 2002525169 | A | 8/2002 |
| JP | 2002541915 | A | 12/2002 |
| JP | 2004510471 | A | 4/2004 |
| JP | 2005500101 | A | 1/2005 |
| JP | 2005512611 | A | 5/2005 |
| JP | 2007536989 | A | 12/2007 |
| JP | 2008535572 | A | 9/2008 |
| JP | 4335487 | B2 | 9/2009 |
| JP | 2010517623 | A | 5/2010 |
| JP | 2010528761 | A | 8/2010 |
| JP | 2010188189 | A | 9/2010 |
| JP | 2010536527 | A | 12/2010 |
| JP | 2012504031 | A | 2/2012 |
| JP | 2012152563 | A | 8/2012 |
| JP | 2013543399 | A | 12/2013 |
| JP | 2014513585 | A | 6/2014 |

(56) References Cited

FOREIGN PATENT DOCUMENTS

| | | | |
|---|---|---|---|
| JP | 2014517720 | A | 7/2014 |
| JP | 2016501104 | A | 1/2016 |
| JP | 2016518948 | A | 6/2016 |
| JP | 2017527397 | A | 9/2017 |
| JP | 6392778 | B2 | 9/2018 |
| RU | 2434604 | C1 | 11/2011 |
| WO | 96/02212 | A1 | 2/1996 |
| WO | 0018333 | A1 | 4/2000 |
| WO | 0062716 | A1 | 10/2000 |
| WO | 0128453 | A2 | 4/2001 |
| WO | 01/41679 | A1 | 6/2001 |
| WO | 0224118 | A1 | 3/2002 |
| WO | 0224119 | A1 | 3/2002 |
| WO | 0207795 | A3 | 5/2002 |
| WO | 0245933 | A2 | 6/2002 |
| WO | 0247468 | A1 | 6/2002 |
| WO | 02100301 | A1 | 12/2002 |
| WO | 03007795 | A2 | 1/2003 |
| WO | 03047468 | | 6/2003 |
| WO | 03090834 | A2 | 11/2003 |
| WO | 2005112827 | A2 | 12/2005 |
| WO | 2006108090 | A2 | 10/2006 |
| WO | 2007016251 | A3 | 4/2008 |
| WO | 2008052421 | A1 | 5/2008 |
| WO | 2008091589 | A1 | 7/2008 |
| WO | 2008097589 | | 8/2008 |
| WO | 2008097592 | A2 | 8/2008 |
| WO | 2008150529 | A1 | 12/2008 |
| WO | 2009029199 | A1 | 3/2009 |
| WO | 2009045332 | A2 | 4/2009 |
| WO | 2010037141 | A1 | 4/2010 |
| WO | 2010057262 | A1 | 5/2010 |
| WO | 2010086460 | A1 | 8/2010 |
| WO | 2011109450 | A2 | 9/2011 |
| WO | 2011109801 | A2 | 9/2011 |
| WO | 2011112706 | A2 | 9/2011 |
| WO | 2012004460 | A2 | 1/2012 |
| WO | 2012040643 | A2 | 3/2012 |
| WO | 2012047644 | A2 | 4/2012 |
| WO | 2012065080 | A2 | 5/2012 |
| WO | 2012082952 | A2 | 6/2012 |
| WO | 2012110767 | A2 | 8/2012 |
| WO | 2012116368 | A2 | 8/2012 |
| WO | 2012135603 | A2 | 10/2012 |
| WO | 2012167131 | A1 | 12/2012 |
| WO | 2013096854 | A2 | 6/2013 |
| WO | 2014018189 | A2 | 1/2014 |
| WO | 2014018432 | A2 | 1/2014 |
| WO | 2014099150 | A1 | 6/2014 |
| WO | 2014099163 | A1 | 6/2014 |
| WO | 2014099722 | A1 | 6/2014 |
| WO | 2014144937 | A2 | 9/2014 |
| WO | 2015045002 | A1 | 4/2015 |
| WO | 2015085138 | A1 | 6/2015 |
| WO | 2015171743 | A2 | 11/2015 |
| WO | 2015173794 | A1 | 11/2015 |
| WO | 2016028591 | A1 | 2/2016 |
| WO | 2016044223 | A1 | 3/2016 |
| WO | 2016100913 | A1 | 6/2016 |
| WO | 2016172349 | A1 | 10/2016 |
| WO | 2016186909 | A1 | 11/2016 |
| WO | 2019067219 | A1 | 4/2019 |
| WO | 2019067220 | A1 | 4/2019 |
| WO | 2019074607 | A1 | 4/2019 |
| WO | 2019089138 | A1 | 5/2019 |

OTHER PUBLICATIONS

Clough, Norman E. Introducing a New Family of GORE ePTFE Fibers (2007), pp. 1-10.

International Preliminary Report on Patentability received for PCT Patent Application No. PCT/US2018/053278, mailed on May 14, 2020, 8 pages.

International Search Report and Written Opinion from PCT/US2018/053278, dated Dec. 19, 2018, 12 pages.

Mano Thubrikar, “The Aortic Valve”, Chapter 1: Geometry of the Aortic Valve, CRC Press, Inc., Informa Healthcare, 2011, 40 pages.

Opposition from EP16196687.4, mailed on Dec. 12, 2019, 38 pages.

Opposition from EP17187595.8, filed Sep. 12, 2019, 50 pages.

* cited by examiner

TAPERED HEART VALVE COVERING

CROSS-REFERENCE TO RELATED APPLICATION

This application is a continuation of U.S. patent application Ser. No. 17/476,867, filed Sep. 16, 2021, which is a continuation of U.S. patent application Ser. No. 16/129,677, filed Sep. 12, 2018, which claims the benefit of U.S. Patent Application No. 62/579,754, filed Oct. 31, 2017, and U.S. Patent Application No. 62/667,181, filed May 4, 2018, the entire disclosures all of which are incorporated by reference for all purposes.

FIELD

The present disclosure relates generally to heart valve assembles, and more specifically to apparatuses, systems and methods that include a jacket for a heart valve.

BACKGROUND

Prosthetic heart valves have been developed that attempt to mimic the function and performance of a native valve. Prosthetic valves with flexible leaflets typically require some means for securing the leaflets to a support structure, such as a leaflet frame. Leaflet(s) may be secured to the frame, for example, by suturing or adhesive/thermal bonding. In addition, the prosthetic valve is typically attached to a human heart with sutures or some other mechanical attachment means (e.g., staples). For example, the prosthetic valve may be sewn to the heart using suture(s) that pass through a sewing cuff attached to the frame.

The heart valves, including the frames, may have imperfections or other aspects (e.g., resulting from the attachment of the leaflet to the frame) that may contribute to undesirable biological events. Accordingly, it would be desirable to resolve the imperfections or other aspects to facilitate performance of the heart valves.

SUMMARY

According to one example ("Example 1"), a prosthetic valve includes a heart valve having a frame; one or more leaflets attached to the frame; and a jacket surrounding the frame and configured to cover at least one of gaps, spaces, or interfaces in at least one of the frame and interfaces between the frame and the one or more leaflets attached to the frame to enhance the biocompatibility of the heart valve.

According to another example ("Example 2"), further to Example 1, the jacket is molded to at least one of the frame and the one or more leaflets.

According to another example ("Example 3"), further to Example 2, the one or more leaflets and the jacket are each formed of a first material.

According to another example ("Example 4"), further to Example 3, the first material comprises a fluoropolymer.

According to another example ("Example 5"), further to Example 1, the jacket includes a first portion and a second portion, and the first portion and the second portion are coupled together to join the jacket to the frame.

According to another example ("Example 6"), further to Example 5, the first portion includes a first connector, the second portion includes a second connector, and the first connector snaps together with the second connector to join the first portion of the jacket with the second portion of the jacket.

According to another example ("Example 7"), further to Example 5, the first portion and the second portion are secured together by at least one of swaging, an adhesive, a screw, and a rivet.

According to another example ("Example 8"), further to any one of Examples 1-7, further including a sewing cuff arranged with the frame, wherein the jacket is configured to cover an interface between the sewing cuff and the frame.

According to another example ("Example 9"), further to Example 8, the jacket is bonded to the sewing cuff.

According to another example ("Example 10"), further to any one of Examples 1-9, the jacket is configured to avoid thrombosis to enhance the biocompatibility of the frame.

According to another example ("Example 11"), further to any one of Examples 1-10, the jacket is configured to block tissue ingrowth into the one or more leaflets to enhance the biocompatibility of the frame.

According to another example ("Example 12"), further to any one of Examples 1-10, the jacket is configured to promote tissue ingrowth.

According to one example ("Example 13"), further to any one of Examples 1-12, the jacket includes an outflow edge and a transition between the one or more leaflets and the outflow edge includes a fillet.

According to one example ("Example 14"), further to Example 13, the fillet includes a nonlinear surface.

According to one example ("Example 15"), further to Example 13, the fillet extends radially inwardly.

According to one example ("Example 16"), further to any one of Examples 5-15, the first portion of the jacket defines an outflow side of the prosthetic valve, and wherein a flange extends radially outwardly from the first portion of the jacket.

According to one example ("Example 17"), further to any one of Examples 8-15, a flange extends radially outwardly from the jacket on an outflow side of the sewing cuff.

According to one example ("Example 18"), further to any one of Examples 16-17, the flange is longitudinally offset from the sewing cuff.

According to one example ("Example 19"), further to any one of Examples 16-18, the flange is configured to operate as a tissue ingrowth boundary to help obstruct tissue ingrowth into the one or more leaflets.

According to one example ("Example 20"), further to any one of Examples 16-19, the flange is positioned between the sewing cuff and an outflow side of the one or more leaflets.

According to one example ("Example 21"), further to any one of Examples 1-20, the jacket is formed of a rigid material.

According to one example ("Example 22"), further to any one of Example 22, the jacket is formed of a TFE-PMVE copolymer.

According to one example ("Example 23"), further to any one of Examples 1-20, a portion of the jacket is formed of a flexible polymer.

According to one example ("Example 24"), further to any one of Example 23, wherein the flexible polymer is silicone.

According to one example ("Example 25"), further to any one of Examples 23-24, another portion of the jacket is formed of a rigid material.

According to one example ("Example 26"), further to any one of Examples 1-25, the valve also includes a conduit and wherein the jacket is coupled to the conduit to form a valved conduit.

According to one example ("Example 27"), a prosthetic valve including: a frame; one or more leaflets attached to the frame to define at least one frame to leaflet interface; and a jacket that encapsulates the at least one frame-to-leaflet interface and is configured to isolate the interface from blood flow.

According to another example ("Example 28"), further to Example 27, the jacket is configured to create tissue ingrowth boundaries.

According to another example ("Example 29"), further to any one of Examples 27-28, the jacket is configured to alter the blood flow.

According to another example ("Example 30"), further to any one of Examples 27-29, the jacket includes a sewing cuff, and the jacket is bonded to at least one of the frame, the leaflets, and the sewing cuff.

According to another example ("Example 31"), further to any one of Examples 27-30, the jacket is overmolded over the frame.

According to another example ("Example 32"), further to any one of Examples 27-31, the jacket is configured to promote tissue ingrowth.

According to another example ("Example 33"), further to Example 32, the jacket is configured to restrict the tissue ingrowth to the frame without extending onto the one or more leaflets.

According to another example ("Example 34"), further to any one of Examples 32-33, the jacket includes a surface modification to promote tissue ingrowth.

According to another example ("Example 35"), further to any one of Examples 27-34, the jacket includes an outflow edge and a transition between the one or more leaflets and the outflow edge includes a fillet.

According to another example ("Example 36"), further to Example 35, the fillet includes a nonlinear surface.

According to another example ("Example 37"), further to Example 35, the fillet extends radially inwardly.

According to another example ("Example 38"), further to any one of Examples 30-37 24-31, a flange extends radially outwardly from the jacket on an outflow side of the sewing cuff.

According to another example ("Example 39"), further to Example 38, the flange is longitudinally offset from the sewing cuff.

According to another example ("Example 40"), further to any one of Examples 38-39, the flange is configured to operate as a tissue ingrowth boundary to help obstruct tissue ingrowth into the one or more leaflets.

According to another example ("Example 41"), further to any one of Examples 38-40, the flange is positioned between the sewing cuff and an outflow side of the one or more leaflets.

The foregoing Examples are just that, and should not be read to limit or otherwise narrow the scope of any of the inventive concepts otherwise provided by the instant disclosure.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1:
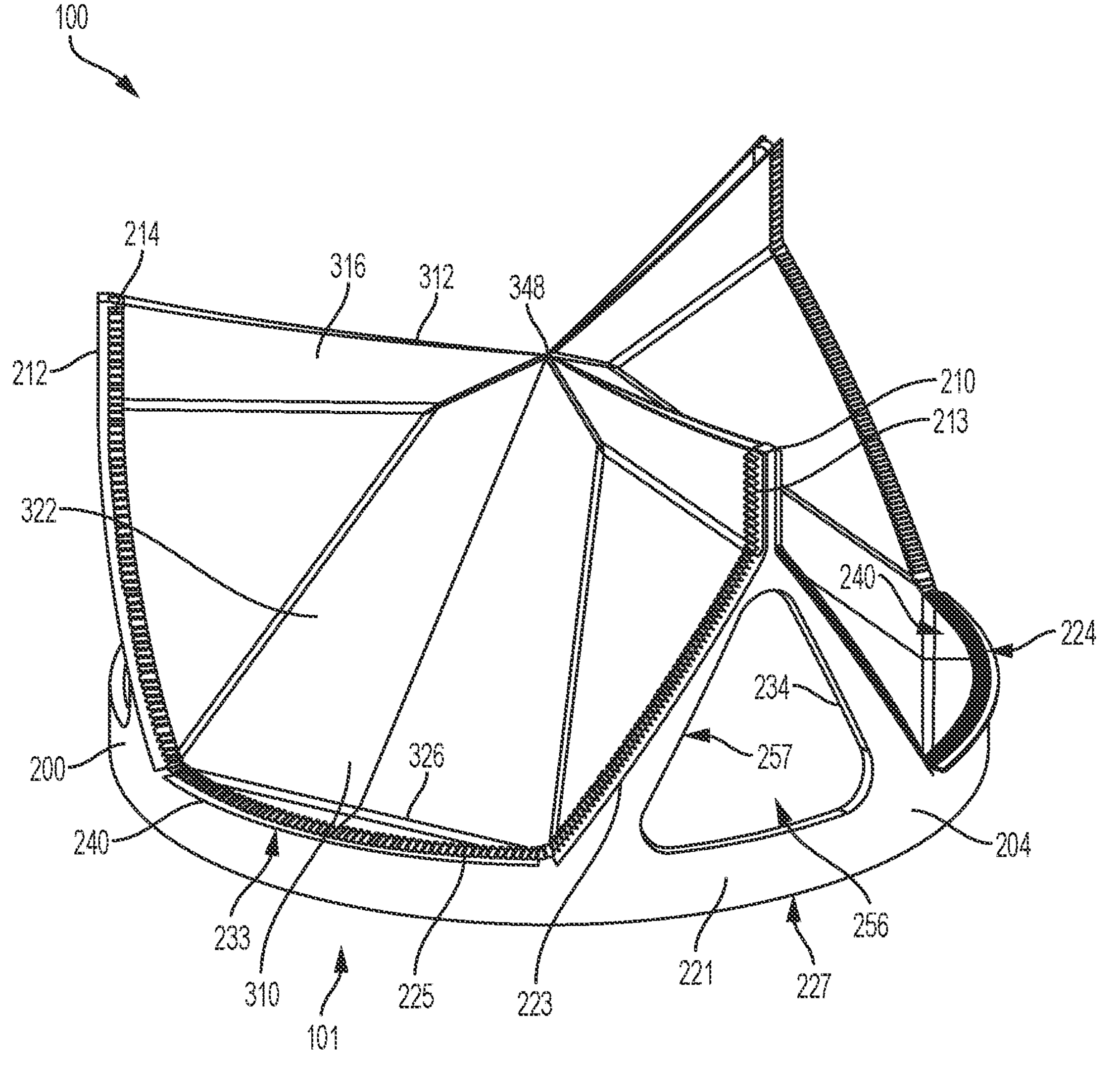
FIG. 1 is an illustration of an example prosthetic valve in accordance with an embodiment.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Embodiments herein include various apparatus, systems, and methods for a prosthetic valve suitable for surgical and transcatheter placement, such as, but not limited to, cardiac valve replacement. The prosthetic valve is operable as a one-way valve wherein the prosthetic valve defines a valve orifice into which leaflets open to permit flow and close so as to occlude the valve orifice and prevent flow in response to differential fluid pressure.

The prosthetic valve can include a leaflet frame defining an annular ring and having a leaflet contact surface configured to impart a shape to the leaflet that provides proper function of the valve and one or more leaflet retention surfaces to facilitate leaflet retention to the leaflet frame. The leaflets may be non-sewn, minimally sewn, mechanically coupled, bonded, or non-mechanically coupled to the leaflet frame. In addition, the valve may also include a sewing cuff, arranged about the leaflet frame, to provide structure that receives suture for coupling to the implant site. In some examples, the prosthetic valve is wholly synthetic. The prosthetic valve may include one or more drug coatings on one or more portions thereof or may be entirely free of drug coatings.

There may be interface points due to attachment of leaflets to the frame, attachment of the sewing cuff to the frame, and the frame itself. Each aspect may also include various other interface points or other cracks and crevices. The interface points (and cracks and crevices) may cause blood stasis, which can contribute to thrombus formation. Thus, embodiments herein include various apparatus, systems, and methods that include a jacket joined to the frame and configured to enhance the biocompatibility of the frame and lessen the opportunity for thrombus formation. In addition, the jackets discussed herein can contribute to manufacturability of the prosthetic valve, to which the jacket is coupled. The jacket can mask manufacturing imperfections and the jacket is also customizable based on patient and need.

FIG. 1 shows an example prosthetic valve 100 in accordance with an embodiment. The components of the prosthetic valve 100 that can be observed in FIG. 1 include a plurality of leaflets 310 and a leaflet frame 200 that includes a plurality of commissure posts 210 flanked on each side by leaflet window frame element(s) (e.g., two leaflet window sides 223 and a leaflet window base 225 therebetween) that define the leaflet window. Leaflet free edges 312 of the leaflets 310 come together at a coaptation region 316 in a Y-shaped pattern to close the prosthetic valve 100. The prosthetic valve 100 closes in this fashion when the pressure of the blood on the leaflet outflow side is greater than the pressure of the blood on the leaflet inflow side of the prosthetic valve 100. The leaflet free edges 312 of the leaflets 310 move apart to open the prosthetic valve 100 and to let blood flow through the prosthetic valve 100 from the leaflet inflow side when the pressure of the blood on the leaflet inflow side is greater than the pressure on the outflow side. The three leaflets 310 of the embodiment of FIG. 1 meet or nearly meet at a triple point 348.

Generally, the term "distal" is used in the disclosure to refer to the outflow end (distal end) or outflow direction of a prosthetic valve 100, and in turn the term "proximal" is used to refer to the inflow end of a prosthetic valve 100, or a direction opposite the direction of primary flow through the prosthetic valve 100.

The leaflet frame 200 is operable to mechanically couple and support the leaflets 310 by way of, at least in part, a plurality of leaflet frame projections 260 (FIG. 2) that are spaced-apart and project from one or more leaflet retention surfaces 233 of the leaflet frame 200. In various embodiments, the one or more leaflet retentions surfaces 233 are one or more leaflet frame edges, external edges or internal edges, such as a leaflet frame first edge 227, a leaflet frame second edge 224, and a leaflet frame internal edges 234. The leaflet frame projections 260 are each configured to extend through a leaflet aperture defined by the leaflet 310. In some embodiments, the leaflet frame projections 260 can have a tenon-like shape.

The leaflet frame 200 may include an annular shape and has a central longitudinal axis. The leaflet frame 200 comprises a plurality of commissure posts 210 that are spaced from one another. Between two commissure posts 210 is a leaflet window. The portion of the leaflet frame 200 disposed adjacent each commissure post 210 can be an opening, an open framework, or a continuous wall, which may be further defined in part by the leaflet window sides 223. The leaflet retention surface 233 in the embodiment shown in FIG. 1 is the leaflet frame second edge 224 (an example of a leaflet frame external edge), but it is understood that a leaflet retention surface 233 can include any leaflet frame surface including, but not limited to, a leaflet frame second edge 224, a leaflet frame first edge 227, and/or a leaflet frame internal edge 234, such as the side internal edge 257 defining triangular opening 256.

As shown in FIG. 1, each of the leaflet windows are defined by the leaflet frame second edge 224. In particular, the leaflet frame second edge 224 defines a leaflet frame concavity 240 corresponding to each leaflet window. The leaflet frame concavity 240 can be curved or angular. The shown embodiment has an angular leaflet frame concavity 240. A set of leaflet frame elements that, along with the commissure post 210, define each leaflet window are referred to as leaflet window frame elements. A set of leaflet window frame elements can flank each side of a commissure post 210. The set of leaflet window frame elements can include two leaflet window sides 223 and a leaflet window base 225 therebetween. The leaflet window base 225 and the leaflet window sides 223 are configured to couple to and support, along with the commissure posts 210, each leaflet 310 around the perimeter thereof except for the leaflet free edge 312. The commissure post 210 extends from an apex 232 in the outflow direction that is formed at the convergence between two leaflet window sides 223 of adjacent leaflet windows. The extent of leaflet attachment along the commissure post 210 can affect the leaflet free edge 312 so as to create a narrower or wider coaptation region 316 between the adjacent leaflet free edges 312 where the extent is less or more, respectively. It is also understood that the shape of the leaflet free edge 312 and dimensions of the leaflet belly region 322 influence wider or narrower coaptation.

The leaflet frame 200 defines an annular shape having a leaflet frame inner surface and a leaflet frame outer surface 204 opposite the leaflet frame inner surface. Further, the leaflet frame 200 has a leaflet frame first edge 227 and a leaflet frame second edge 224 opposite the leaflet frame first edge 227. As discussed further below, the leaflet frame 200 may include a cuff attachment flange 201 (FIGS. 9B,10B, 12, and 14) that couples adjacent to the leaflet frame first edge 227 so as to project laterally from the leaflet frame outer surface 204. The cuff attachment flange 201 may be made of any suitable material including those materials suitable for the leaflet frame 200 discussed herein. The cuff attachment flange 201 is configured to facilitate coupling of a sewing cuff 285 (discussed further below) to the leaflet frame 200. The cuff attachment flange 201 defines an annular ring that is operable to be slidingly received on the leaflet frame outer surface 204 so as to extend circumferentially around a perimeter of the leaflet frame 200 adjacent the leaflet frame first edge 227.

In some examples, the cuff attachment flange 201 defines a plurality of spaced apart apertures operable to receive suture therethrough so as to facilitate the coupling of the sewing cuff 285 thereon. In other examples, the cuff attachment flange 201 defines a plurality of inwardly projecting spaced apart teeth 205 defining notches 207 therebetween, such that the cuff attachment flange 201 is slidingly received on the leaflet frame outer surface 204, the inwardly projecting spaced apart teeth 205 cooperates with the leaflet frame outer surface 204 such that the notches 207 in combination with the leaflet frame outer surface 204 define a plurality of apertures operable to receive suture therethrough so as to facilitate coupling of the sewing cuff 285 thereon.

Figure 12:
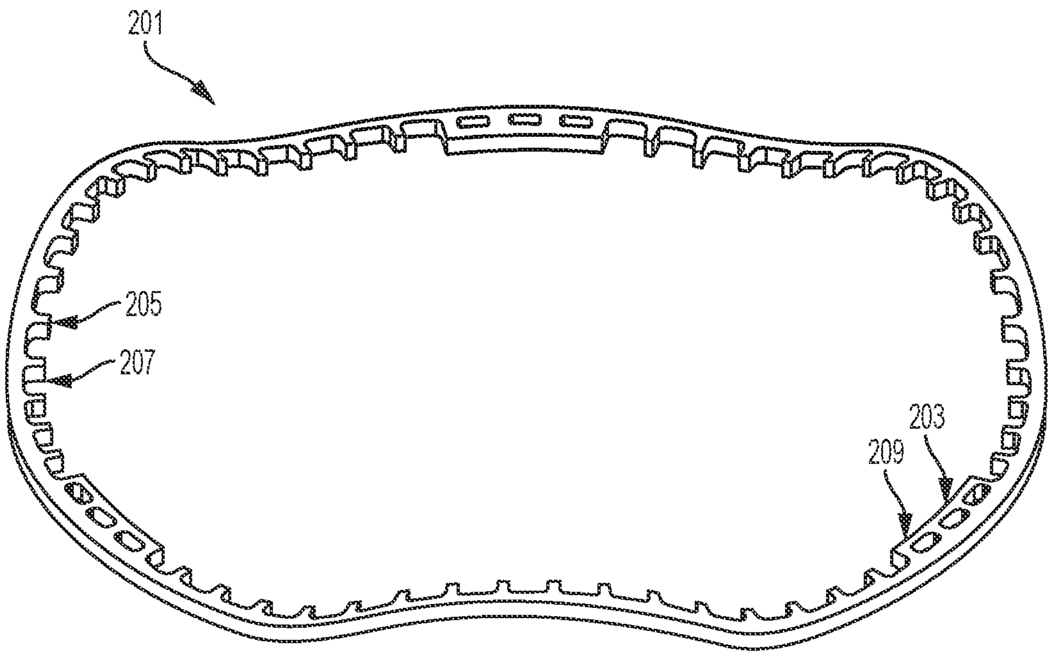
FIG. 12 is a first view of an illustration of an example cuff attachment flange, in accordance with an embodiment.
Figure 13:
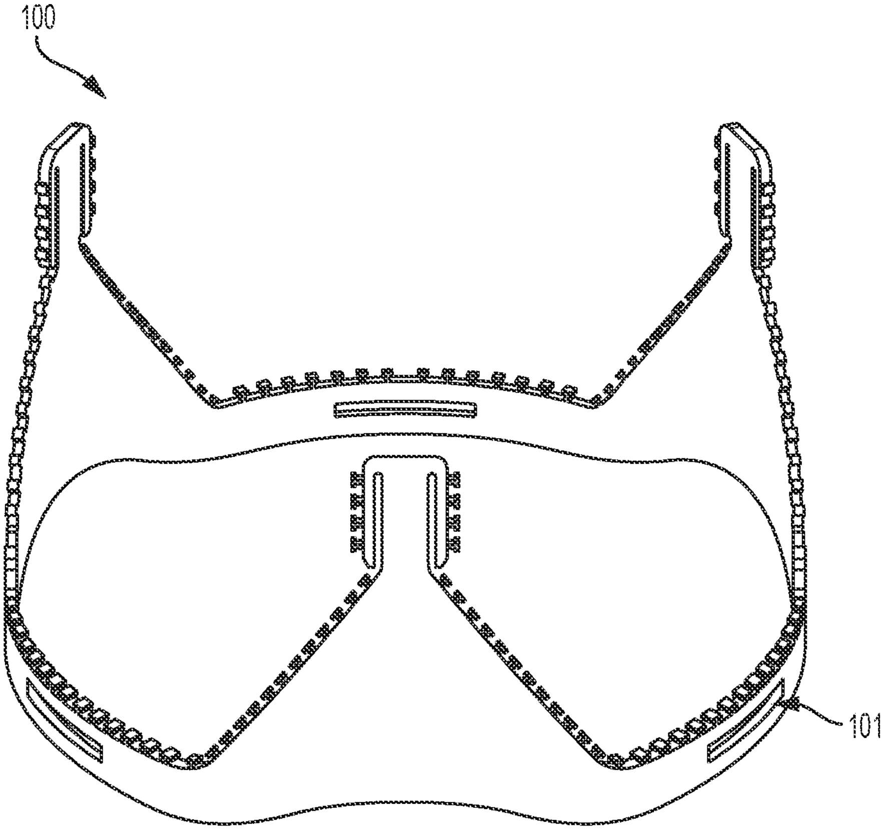
FIG. 13 is a view of an illustration of an example leaflet frame including a keyslot, in accordance with an embodiment.

In another example, the cuff attachment flange 201 includes one or more inwardly projecting keys 209 operable to be received into a corresponding keyway 101 on the leaflet frame 200 (see FIG. 13). As shown in FIG. 12, the key 209 is a flange that is operable to be received in the keyway 101 which, is shown as a slot in FIG. 13. In accordance with an example, the cuff attachment flange 201 is slidingly received onto the leaflet frame 200 at the leaflet frame first edge 227 with each key 209 being received within a corresponding keyway 101. The cooperation between the key 209 and the keyway 101 may be such that the cuff attachment flange 201 may be "snap fit" onto the leaflet frame 200 and fixed thereto. In another example, one or more of the keys 209 is welded to the leaflet frame 200 adjacent the keyway 101 so as to couple the cuff attachment flange 201 to the leaflet frame 200.

Also shown in FIG. 12, it is shown that each key 209 includes a plurality of apertures 203 which, after the key 209 is received into the keyway 101, presents the apertures 203 adjacent the leaflet frame outer surface 204 so as to receive suture therethrough so as to facilitate coupling of the sewing cuff 285 thereon. The cuff attachment flange 201 may be made according to known methods, including laser cutting, molding, stamping, or other known processes.

In some examples, the cuff attachment flange 201, after being slidingly received on the leaflet frame 200, may be welded to the leaflet frame 200, fixing the cuff attachment flange 201 to the leaflet frame 200.

In some examples, the cuff attachment flange 201 may be integral with the leaflet frame 200.

Two ends of the sewing cuff 285 are received and coupled to either side of the cuff attachment flange 201 by passing suture through the two ends of the sewing cuff and through the apertures formed in the cuff attachment flange 201 or defined between the cuff attachment flange 201 and the leaflet frame outer surface 204, as mentioned above.

Figure 9A:
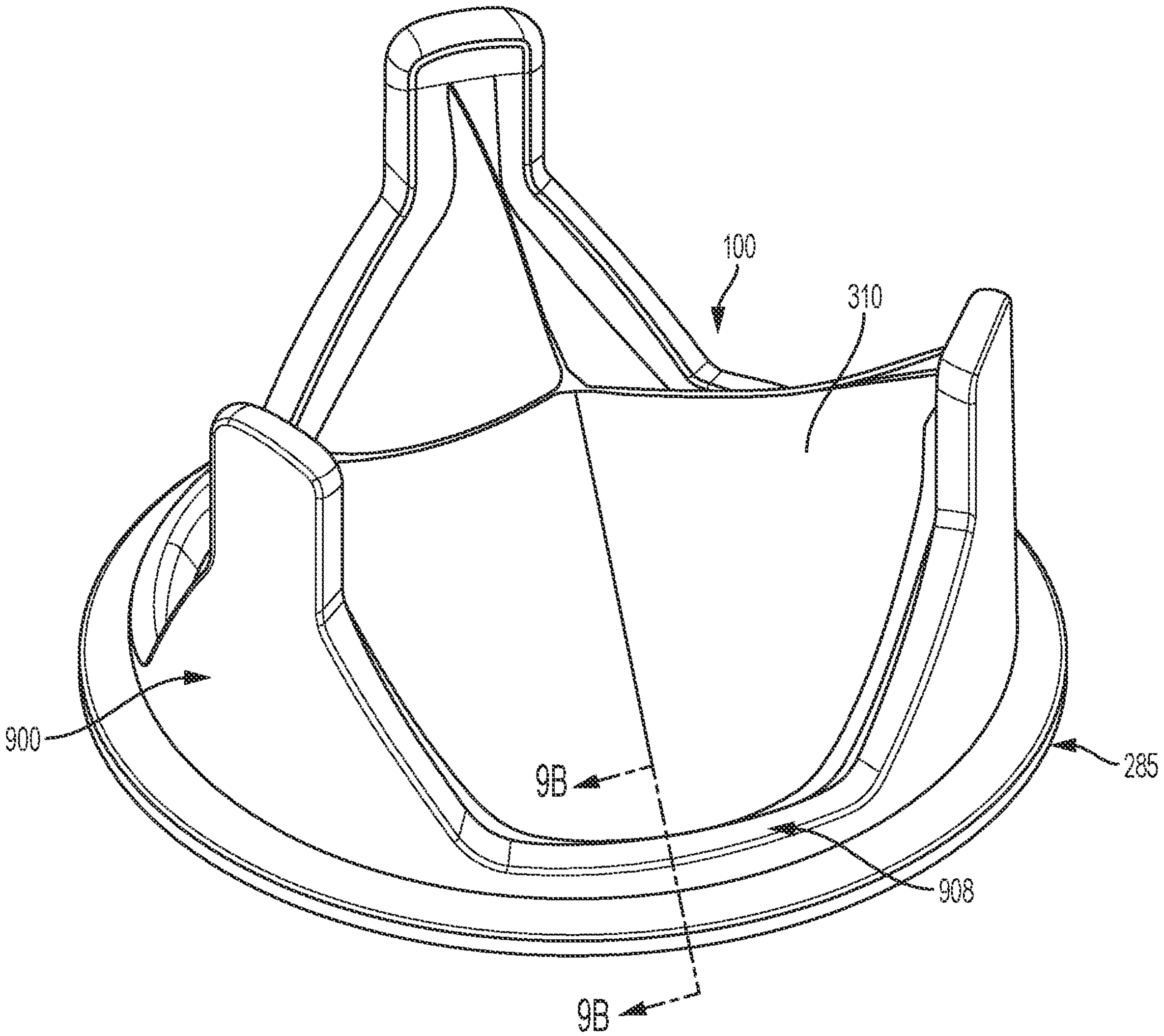
FIG. 9A is a first view of an illustration of an example jacket coupled to a prosthetic valve, in accordance with an embodiment.
Figure 9B:
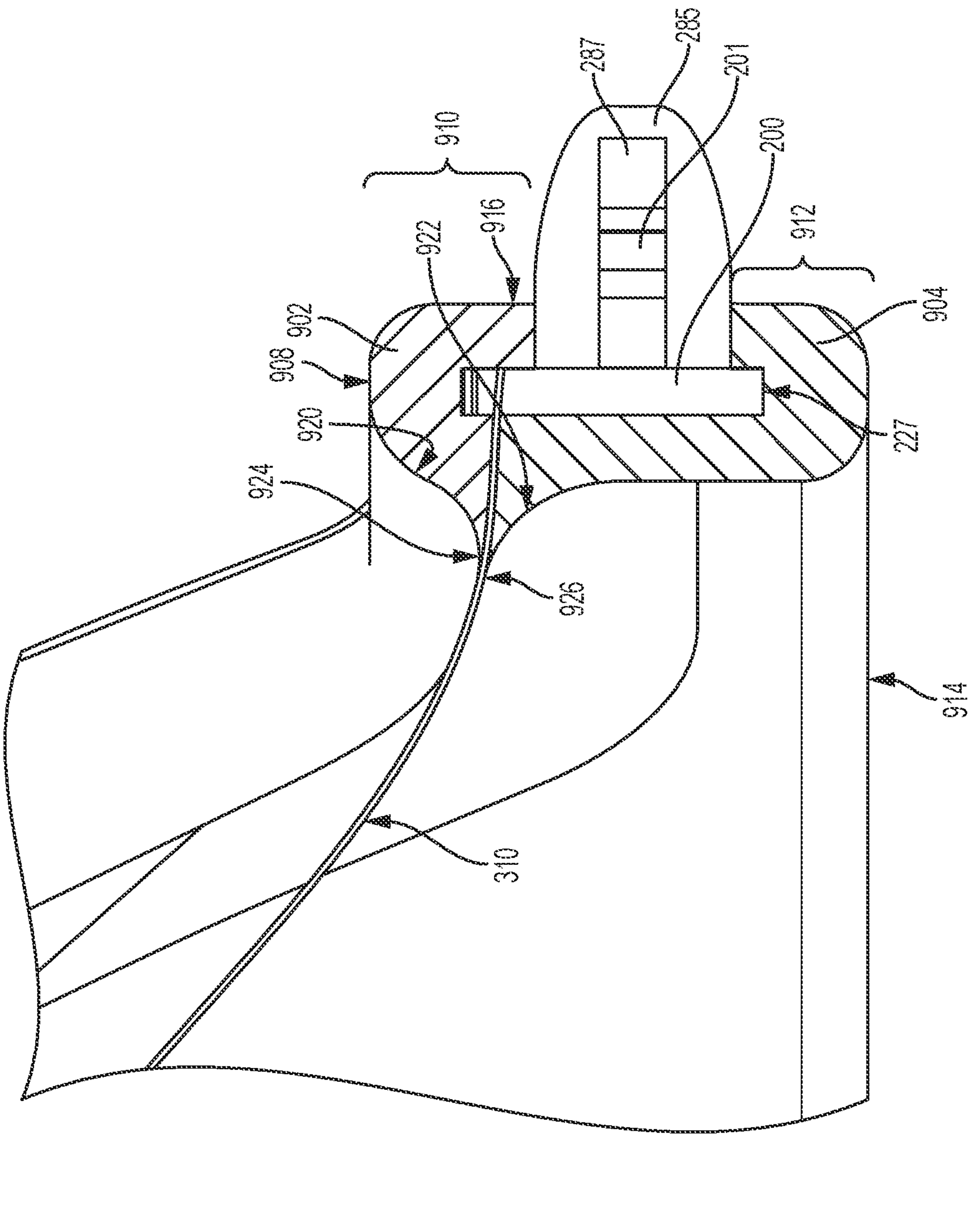
FIG. 9B is a cross section view of the example jacket shown in FIG. 9A taken along line 9B-9B of FIG. 9A.
Figure 10A:
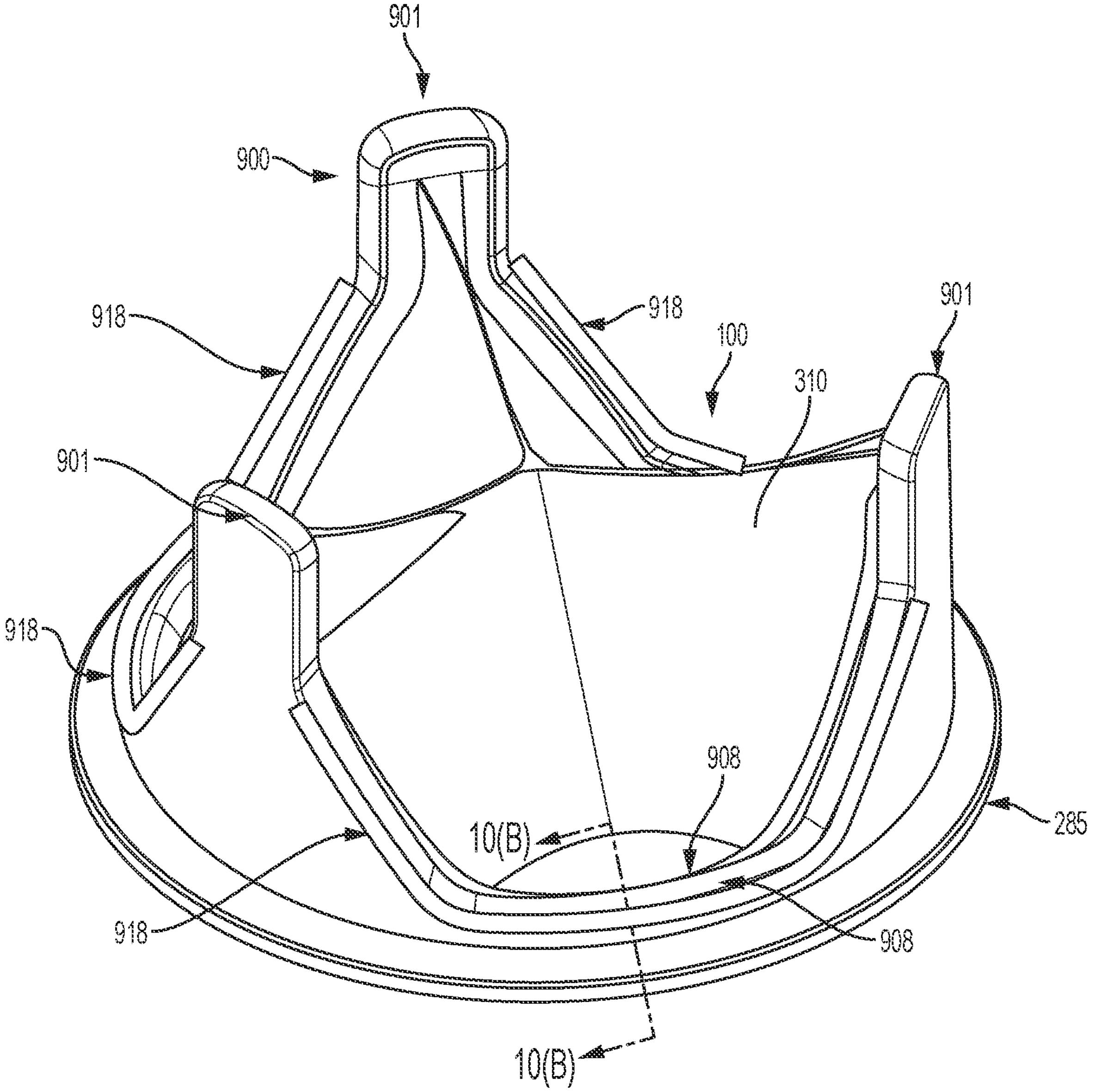
FIG. 10A is a first view of an illustration of an example jacket coupled to a prosthetic valve, in accordance with an embodiment.
Figure 10B:
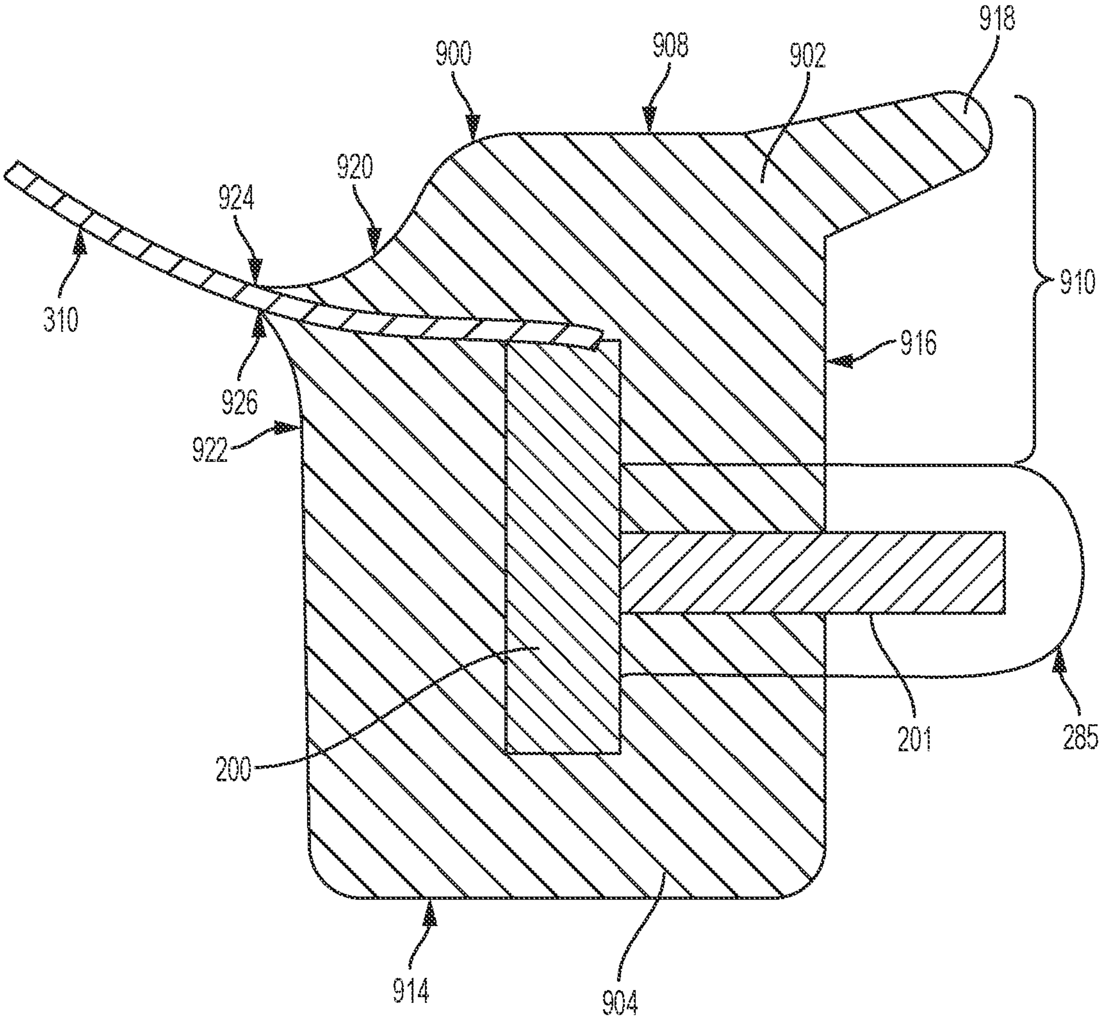
FIG. 10B is a cross section view of the example jacket shown in FIG. 10A taken along line 10B-10B of FIG. 10A.

In some examples, the leaflet frame first edge 227 and the cuff attachment flange 201 define a planar circumference, as shown in FIGS. 9B and 10B. In other examples, the leaflet frame first edge 227 and the cuff attachment flange 201 define a corresponding non-planar circumference (also referred to as a coronet shape). That is, the leaflet frame first edge 227 and the cuff attachment flange 201 define a plurality of scallops, or out of plane curves, that are operable to present the sewing cuff 285, which will take a complementary shape when received onto and coupled to the cuff attachment flange 201, to a native valve annulus that has a corresponding non-planar circumference (coronet shape). Further, in an example, the sewing cuff insert 287 also has a complementary circumference so as to further shape the sewing cuff 285.

In some examples, the sewing ring insert is composed of medical grade silicone. The sewing ring insert may be pre-formed, such as into an annular shape or a shape otherwise corresponding to one or more of the leaflet frame 200, the cuff attachment flange 201 and the sewing cuff 285, or may be injected into the sewing cuff 285 in a non-solid form. In various examples, the sewing insert provides internal support to the sewing ring. In some examples, the sewing insert helps seal needle and suture penetrations through the sewing cuff 285 made during implantation.

Similarly, each commissure post 210 has a post outer side 212 and a post inner side 214 opposite the post outer side 212. Further, each commissure post 210 has two post lateral sides 213 that are opposite each other and extending between the post inner side 214 and the post outer side 212 such that all sides, namely, the post outer side 212, the two post lateral sides 213, and the post inner side 214, define a perimeter of each commissure post 210.

In accordance with an embodiment, the leaflet frame 200 is annular about a central longitudinal axis of the prosthetic valve 100 as shown in FIG. 1. The leaflet frame 200 defines three leaflet windows. In the embodiment shown, a leaflet window base 225 is flanked on each side by two leaflet window sides 223 that together define three sides of an arced isosceles trapezoid, wherein the leaflet frame second edge 224 at the leaflet window base 225 is substantially flat. The leaflet attachment region is coupled to the leaflet window base 225, each of the two leaflet window sides 223, and the commissure posts 210. The commissure posts 210 can be equally spaced from one another around the leaflet frame 200. The portion of the leaflet frame 200 that is disposed under each commissure post 210 and between adjacent leaflet windows is a framed triangular opening 256 defined by leaflet frame internal edges 234 of neighboring leaflet window sides 223 and the leaflet frame base. While the triangular opening 256 is shown as open, it can be capped or sealed in various embodiments.

Figure 14:
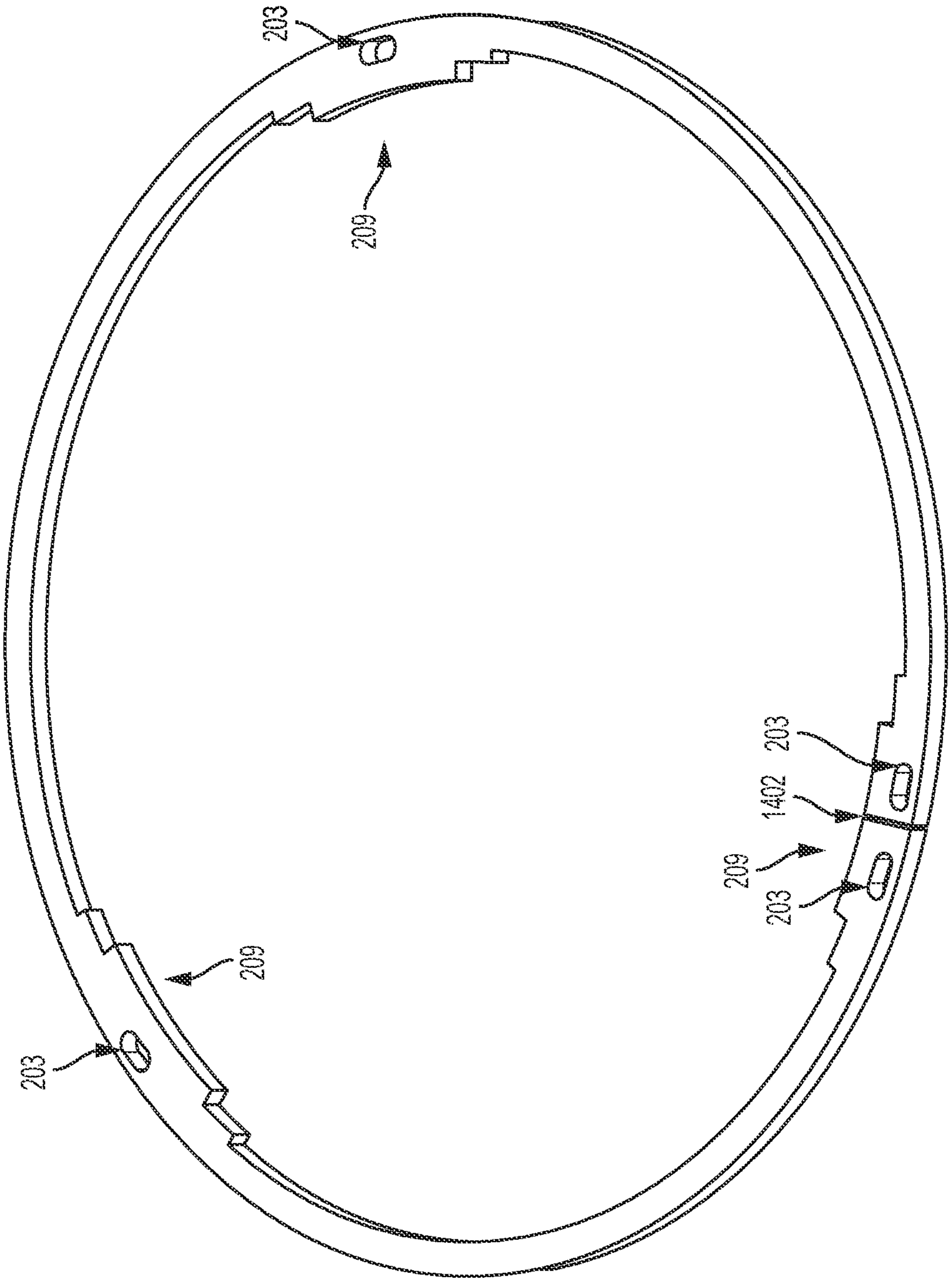
FIG. 14 is a first view of an illustration of another example cuff attachment flange, in accordance with an embodiment.

FIG. 14 is a first view of an illustration of another example cuff attachment flange 201, in accordance with an embodiment. As discussed above, the leaflet frame 200 may include a cuff attachment flange 201. The cuff attachment flange 201 may be made of any suitable material including those materials suitable for the leaflet frame 200 discussed herein. The cuff attachment flange 201 is configured to facilitate coupling of a sewing cuff 285 to the leaflet frame 200. The cuff attachment flange 201 defines an annular ring that is operable to be received on the leaflet frame outer surface 204 so as to extend circumferentially around a perimeter of the leaflet frame 200.

The cuff attachment flange 201 may include a split-portion 1402 that facilitates placement of the cuff attachment flange 201 about the perimeter of the leaflet frame 200. The split-portion 1402 may allow for separation of the cuff attachment flange 201 to place the cuff attachment flange 201 about the perimeter of the leaflet frame 200.

In some examples, the cuff attachment flange 201 defines a plurality of spaced apart apertures operable to receive suture therethrough so as to facilitate the coupling of the sewing cuff 285 thereon. In another example, the cuff attachment flange 201 includes one or more inwardly projecting keys 209 operable to be received into a corresponding keyway 101 on the leaflet frame 200 (see FIG. 13). As shown in FIG. 14, the key 209 is a flange that is operable to be received in the keyway 101 which, is shown as a slot in FIG. 13. In accordance with an example, the cuff attachment flange 201 may separate at the split-portion 1402 and arrange each key 209 received within a corresponding keyway 101. The cooperation between the key 209 and the keyway 101 may be such that the cuff attachment flange 201 may be "snap fit" onto the leaflet frame 200 and fixed thereto.

Also shown in FIG. 14, it is shown that each key 209 includes a plurality of apertures 203 which, after the key 209 is received into the keyway 101, presents the apertures 203 adjacent the leaflet frame outer surface 204 so as to receive suture therethrough so as to facilitate coupling of the sewing cuff 285 thereon. The cuff attachment flange 201 may be made according to known methods, including laser cutting, molding, stamping, or other known processes.

Figure 2:
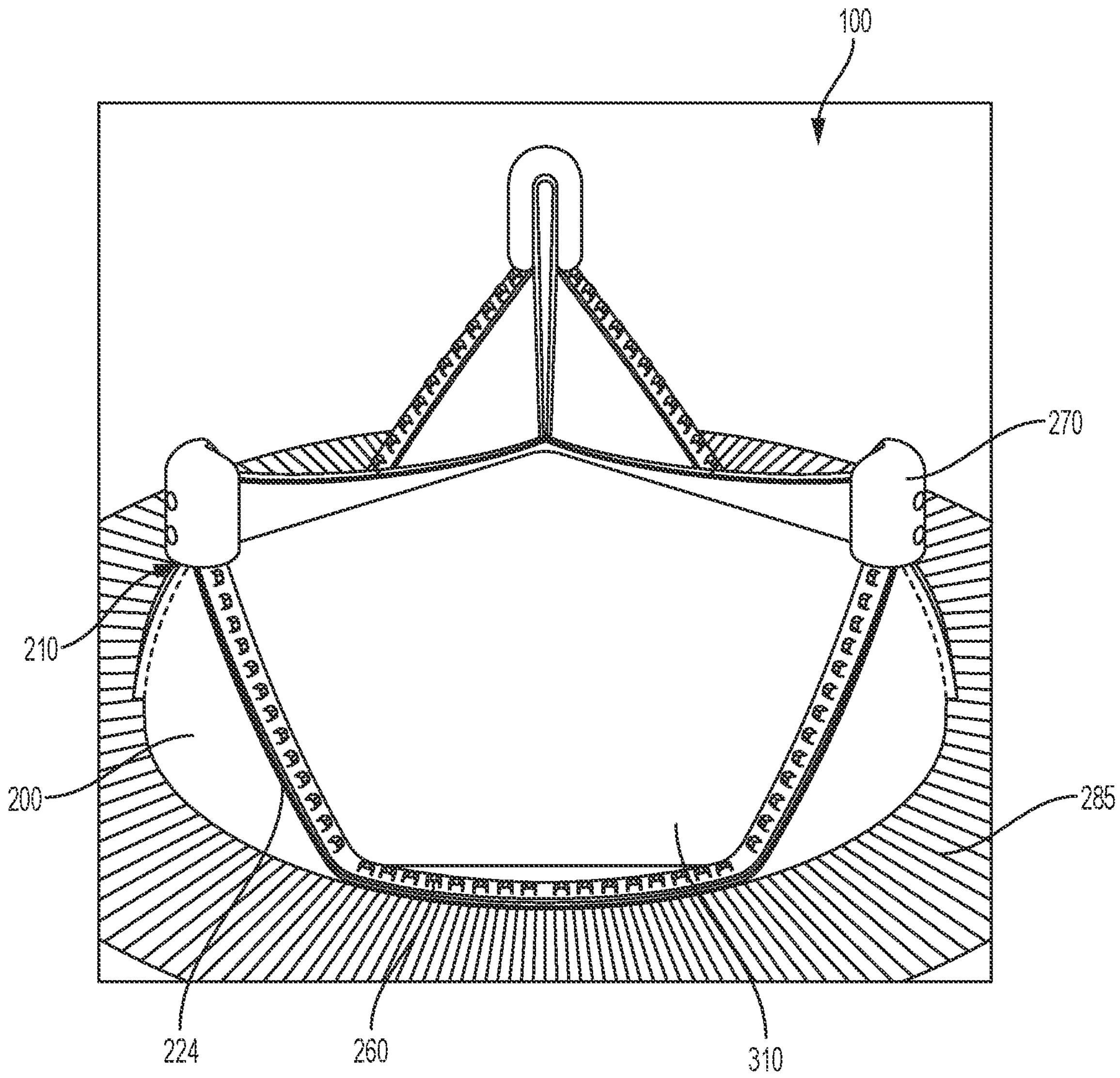
FIG. 2 is an illustration of an example prosthetic valve that includes a sewing cuff in accordance with an embodiment.

FIG. 2 shows an example prosthetic valve 100 with a sewing cuff 285, in accordance with an embodiment. The sewing cuff 285 is arranged about a leaflet frame 200 in accordance with an embodiment. In some examples, the sewing cuff 285 may be arranged about the cuff attachment flange 201 extending radially outwardly from the leaflet frame outer surface 204 of the leaflet frame 200 (FIGS. 9B and 10B). The sewing cuff 285 is operable to provide structure that receives suture for coupling to the implant site. The sewing cuff 285 may comprise any suitable material, such as, but not limited to, PTFE, ePTFE, double velour polyester, and silicone. The sewing cuff 285 materials may be in woven or non-woven forms. For instance, the sewing cuff may be comprised of an ePTFE fabric. The sewing cuff 285 may be located circumferentially around a perimeter of the leaflet frame base of the leaflet frame 200, such as the leaflet frame first edge 227. The sewing cuff 285 may comprise a filler material, such as, but not limited to, a silicone ring. In some examples, the sewing ring permits or promotes tissue ingrowth to help minimize paravalvular leakage. In some examples, the sewing ring additionally or alternatively helps provide anatomical fixation of the prosthetic valve.

Figure 3A:
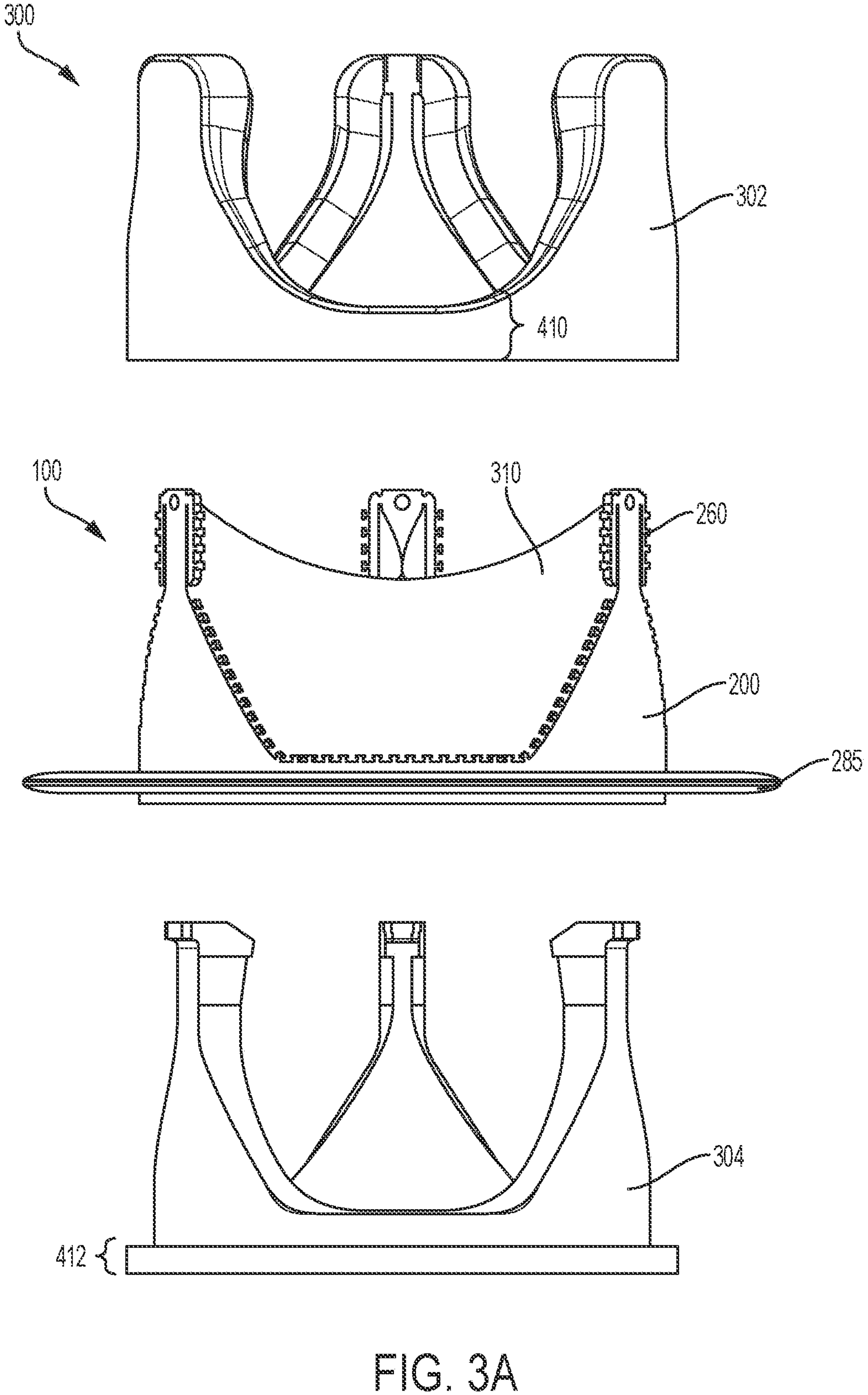
FIG. 3A is a first view of an exploded illustration of an example jacket with a prosthetic valve, in accordance with an embodiment.

FIG. 3A is a first view of an exploded illustration of an example jacket 300 with a prosthetic valve 100, in accordance with an embodiment. The leaflet frame 200 includes one or more leaflets 310 attached to the leaflet frame 200. As discussed in detail with reference to FIG. 1, the leaflets 310 are attached to the leaflet frame 200 by the plurality of leaflet frame projections 260. The mechanical coupling of the leaflets 310 is accomplished by the various aspects of the leaflet frame 200. As shown in FIG. 3A, the leaflet frame 200 includes a number of uneven, rough, or not smooth surfaces. A jacket 300 may be joined to the frame in order to enhance the biocompatibility of the leaflet frame 200 and the prosthetic valve 100. More specifically, the jacket 300 is configured to cover gaps, spaces, interfaces or other structural aspects that are present in the leaflet frame 200 and/or interfaces between the leaflet frame 200 and the one or more leaflets 310 attached to the leaflet frame 200 to enhance the biocompatibility of the leaflet frame 200. In some examples, the jacket 300 additionally helps maintain mechanical attachment of the leaflets 310 to the leaflet frame 200, including the leaflet frame projections 260. In some examples, the jacket 300 operates as a strain relief for the leaflet 310. For instance, in some examples, the jacket 300 minimizes the strain of the leaflets 310 at the leaflet frame projections 260, which helps minimize failures of the leaflets 310 at the leaflet frame projections 260.

As discussed further below, the jacket 300 may be configured to include one or more features or geometries that provide for smooth transitions between the jacket 300 and the leaflet 310. For instance, in some examples, the jacket 300 may include one or more fillets at or proximate a transition between the jacket 300 and the leaflet 310. Thus, in some examples, the fillets provide for a blended interface between the jacket 300 and the leaflets 310. These types of smooth transitions help minimize gaps and crevices, and thus help minimize stagnate blood regions and/or thrombus formation.

The uneven, rough, or not smooth surfaces in the leaflet frame 200 may be present in the leaflet frame 200 itself and/or may be present in the interfaces between aspects of the prosthetic valve 100. The leaflets 310 are attached to the frame, and the leaflet frame 200 may also include a sewing cuff 285. Micro or macroscopic interfaces are present between the leaflet frame 200 and the leaflets 310 and the leaflet frame 200 and the sewing cuff 285. The interfaces, cracks, crevices, and other structural aspects may contribute to thrombus formation when the prosthetic valve 100 is implanted. These structural aspects, for example, can contribute to stagnate blood regions. Stagnate blood regions negatively affect biocompatibility as the stasis can contribute to thrombus formation. Thus, the jacket 300 enhances the biocompatibility of the leaflet frame 200 by covering, wrapping, or hiding the interfaces, cracks, crevices, other structural aspects, and can also optimize blood flow.

The jacket 300 includes a first portion 302 (an outflow jacket portion) and a second portion 304 (an inflow jacket portion). As shown in FIG. 3A, the first portion 302 of the jacket 300 includes an outflow jacket height 410 and the second portion 304 of the jacket 300 includes an inflow jacket height 412.

Figure 3B:
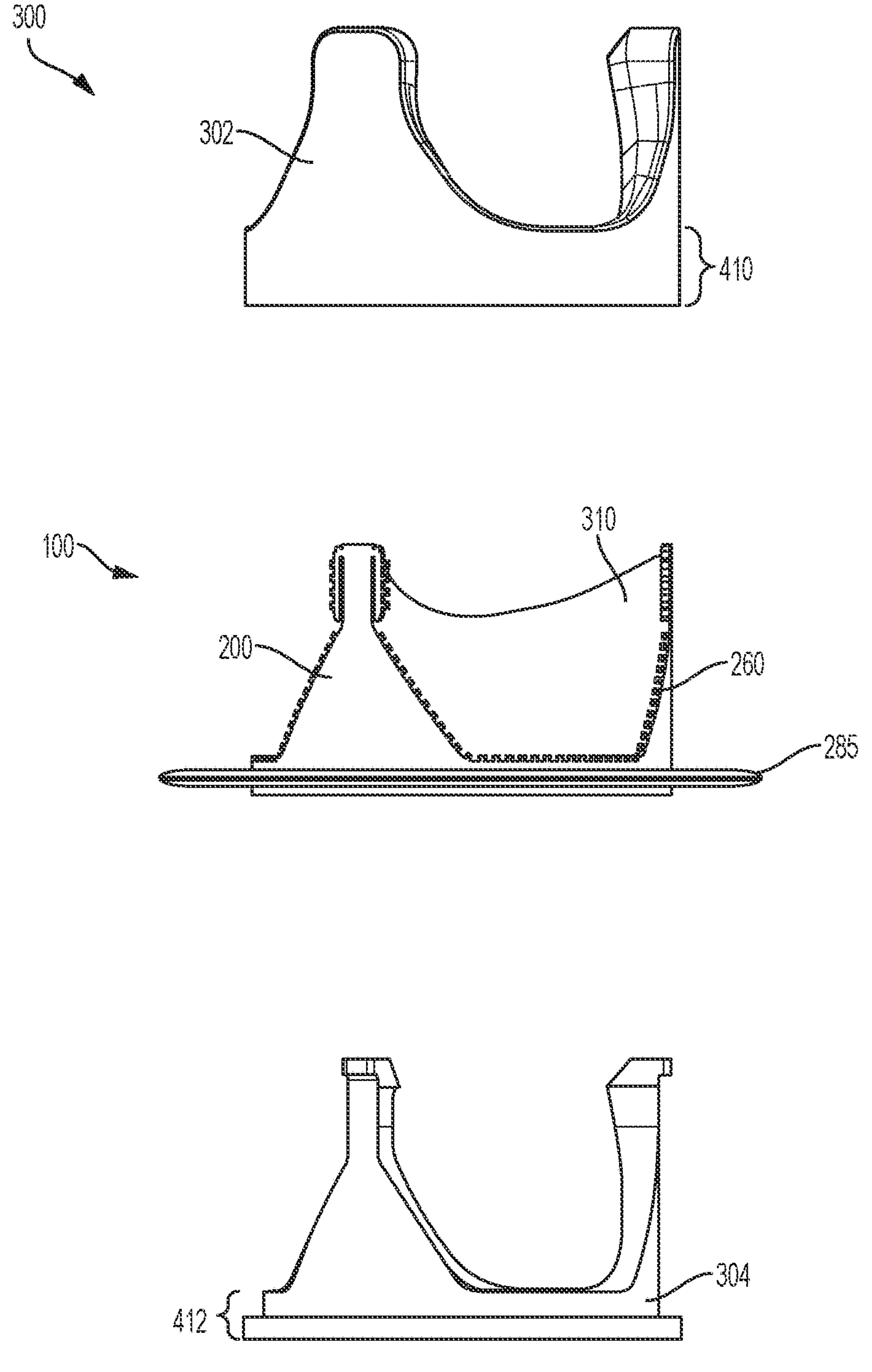
FIG. 3B is a second view of an exploded illustration of the jacket and prosthetic valve shown in FIG. 3A.
Figure 3C:
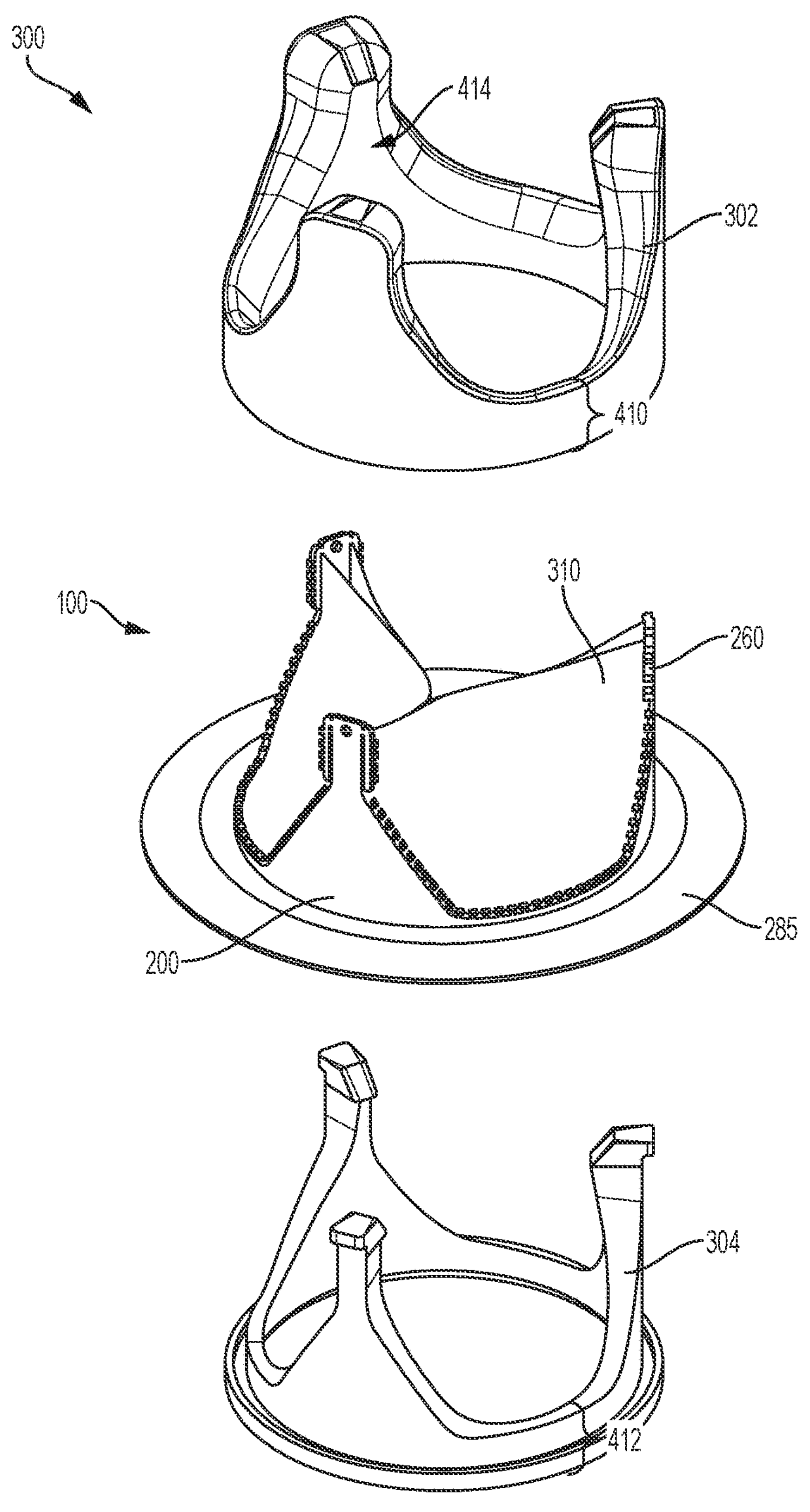
FIG. 3C is a third view of an exploded illustration of the jacket and prosthetic valve shown in FIGS. 3A-B.

FIG. 3B is a second view of an exploded illustration of the jacket 300 and prosthetic valve 100 shown in FIG. 3A and FIG. 3C is a third view of an exploded illustration of the jacket 300 and prosthetic valve 100 shown in FIGS. 3A-B. The first portion 302 and the second portion 304 are configured to couple together to form the jacket 300 around the frame. The first portion 302 and the second portion 304 together around the frame is shown in further detail in FIGS. 4A-C. In certain instances, the first portion 302 and the second portion 304 are secured together by at least one of swaging, a snap fit, a click fit, one or more staples, tape, adhesives, one or more screws, one or more rivets, insert molding or overmolding.

Each of the outflow jacket height 410 and/or the inflow jacket height 412 may be altered based on the specific need of the jacket 300. The outflow jacket height 410 and the inflow jacket height 412 may be determined by measuring the lowest point in the jacket 300 at which the leaflet 310 attaches. The jacket 300 can facilitate tissue growth (e.g., tissue ingrowth or tissue overgrowth) relative to the prosthetic valve 100. Tissue overgrowth, in this context, refers to tissue growing over the leaflet frame 200 and contacting the leaflet 310, which causes a thrombus response. Thus, the outflow jacket height 410 and/or the inflow jacket height 412 is tailored to avoid ingrowth of tissue onto the leaflets 310. In certain instances, the outflow jacket height 410 and/or the inflow jacket height 412 are determined relative to the sewing cuff 285. The outflow jacket height 410 and/or the inflow jacket height 412 may be altered, without changing the leaflet frame 200, in response to patient valve size, position, and/or desired flow characteristics.

Figure 4A:
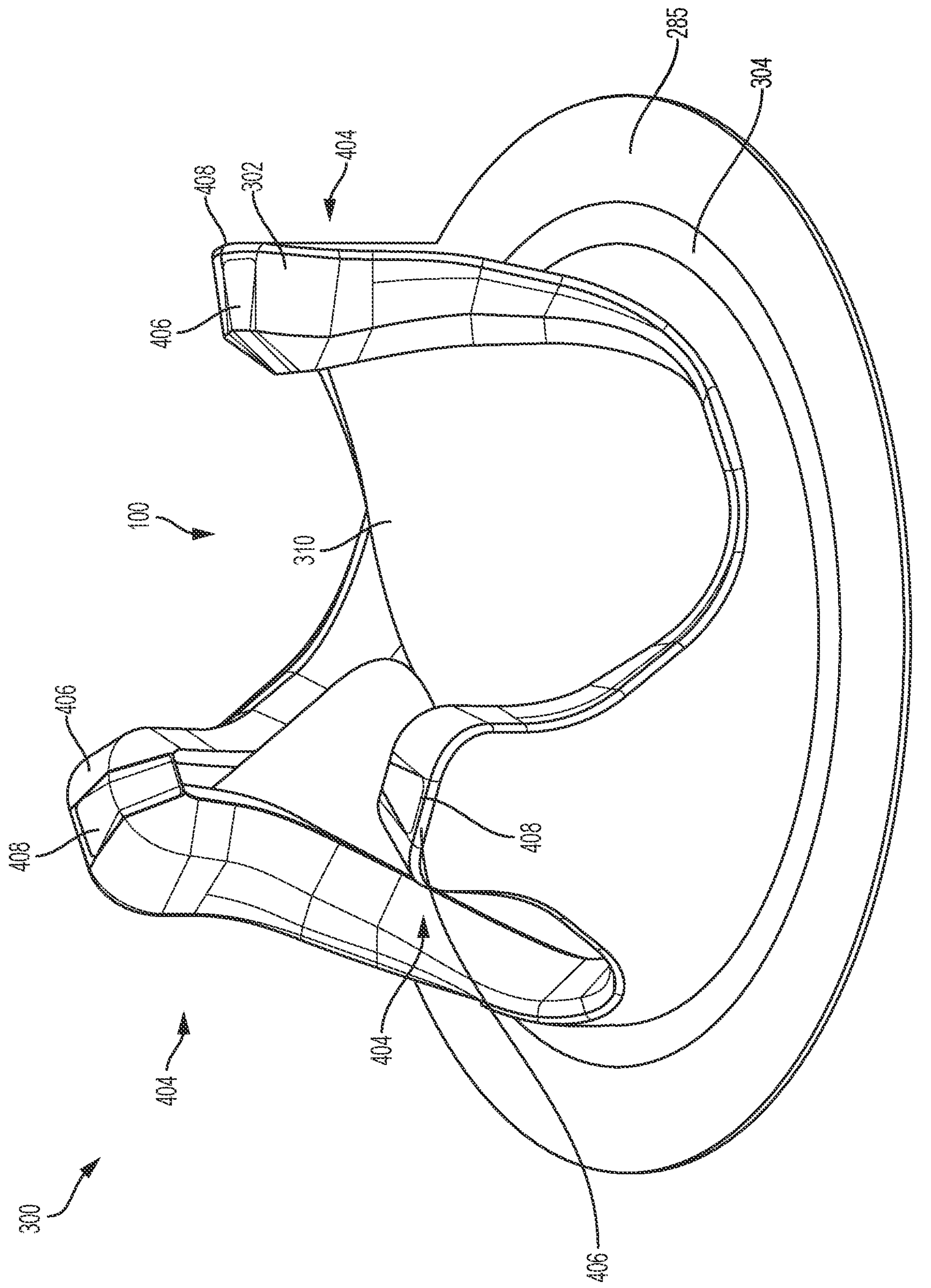
FIG. 4A is a first view of an illustration of an example jacket coupled to a prosthetic valve, in accordance with an embodiment.

FIG. 4A is a first view of an illustration of an example jacket 300 coupled to a prosthetic valve 100, in accordance with an embodiment. The jacket 300 shown in FIGS. 4A-C includes a first portion 302 and a second portion 304. The first portion 302 and the second portion 304 are shown secured together. The first portion 302 and the second portion 304 are secured about a frame (not shown) of the prosthetic valve 100. In certain instances, the prosthetic valve 100 may include a sewing cuff (not shown) arranged with the frame as shown in FIG. 2. The jacket 300 is configured to be an interface between the sewing cuff and the frame. In addition, the jacket 300 includes tips 404 (also described as post cover portions) when the first portion 302 and the second portion 304 are joined together. The tips 404, or post cover portions, may be atraumatic, and may be equal to a number of commissure posts 210 in the prosthetic valve 100.

Figure 4B:
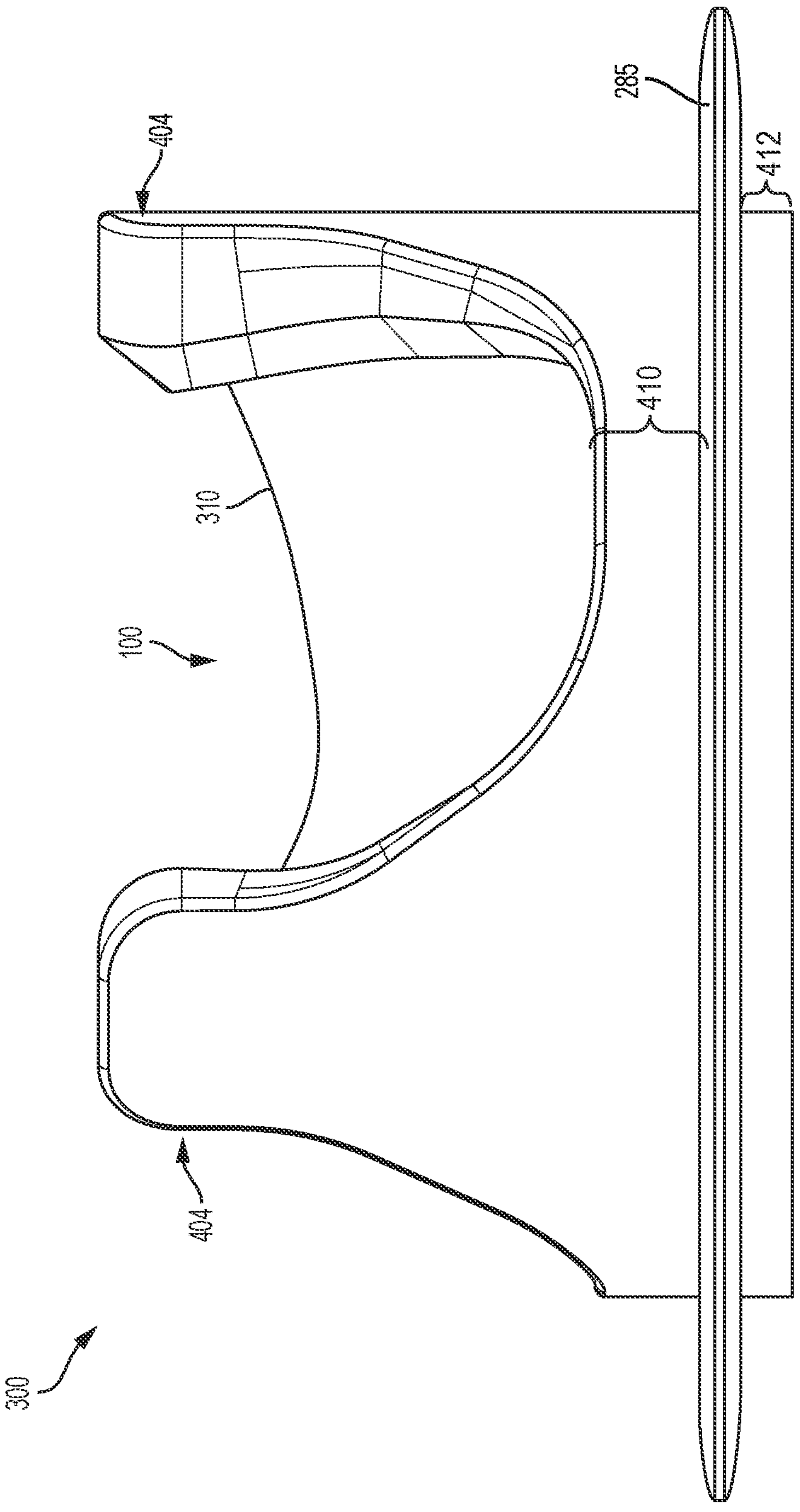
FIG. 4B is a second view of an illustration of the jacket and prosthetic valve shown in FIG. 4A.
Figure 4C:
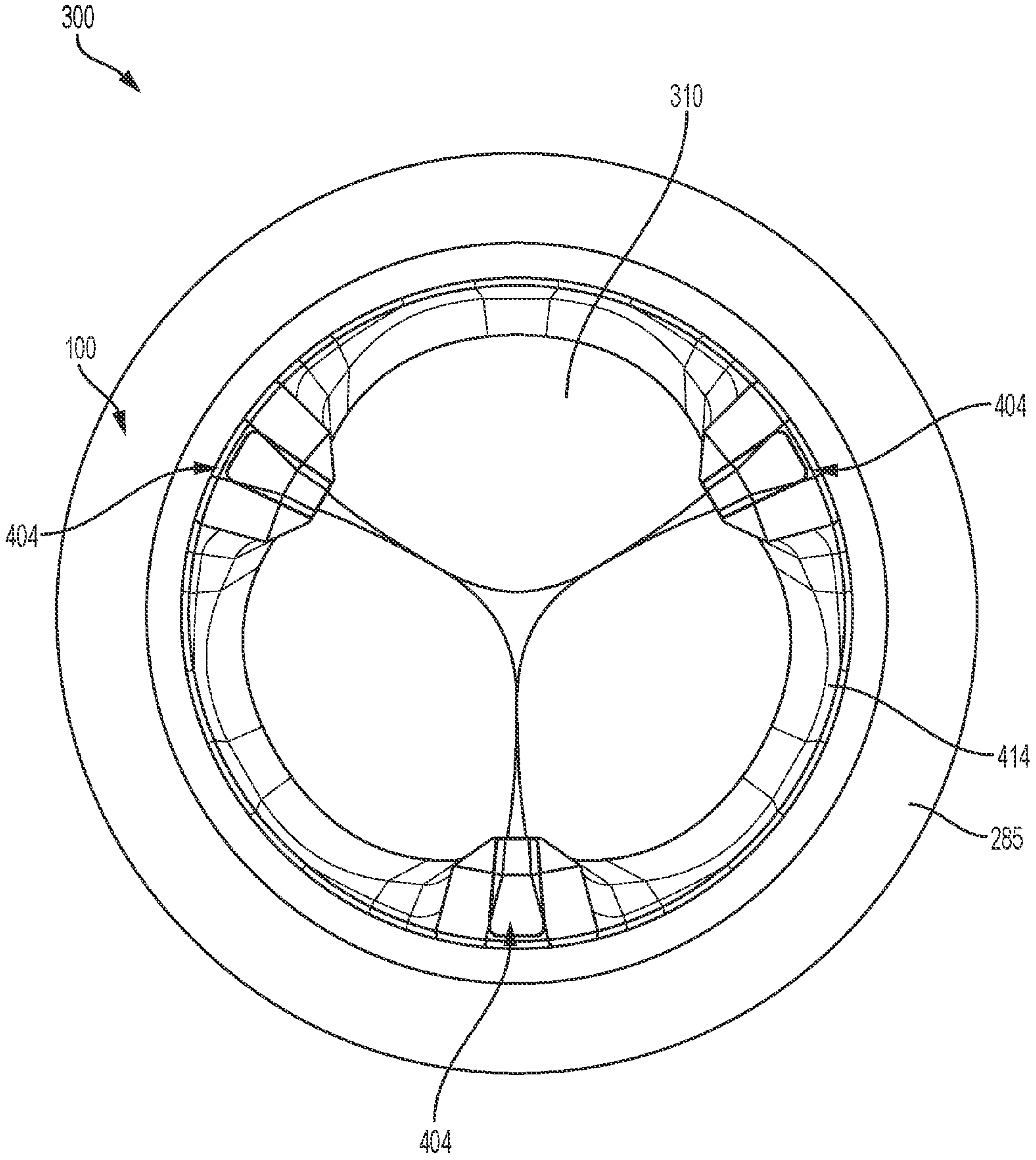
FIG. 4C is a third view of an illustration of the jacket and prosthetic valve shown in FIGS. 4A-B.

As shown in FIGS. 4A-C, the first portion 302 includes first interfaces 406 and the second portion 304 includes second interfaces 408. The first interfaces 406 are configured to join with the second interfaces 408 to couple the first portion 302 to the second portion 304. The first interfaces 406 and the second interfaces 408 couple together to form the tips 404 of the jacket 300. In addition, the first interfaces 406 and the second interfaces 408 can snap together to join the first portion 302 to the second portion 304 and form the jacket 300.

The jacket 300 may be formed of at least one of Polyether ether ketone (PEEK), expanded Polytetrafluoroethylene (ePTFE), Fluorinated ethylene propylene (FEP), copolymers of tetrafluoroethylene (TFE) and perfluoromethyl vinyl ether (PMVE) (TFE-PMVE copolymer), urethanes, polyimides, thermoplastics, thermosets, 3D printable metals and polymers (stainless steel, titanium, etc.) nylon, or any other biocompatible material suitable for long term blood contact that is dimensionally stable, and does not leech contaminates.

The jacket 300 is coupled to or formed about the leaflet frame 200, in various instances, such that the jacket 300 does not interfere with the leaflets 310 or assist in mechanical fixation of the leaflets 310 to the leaflet frame 200. The jacket 300 is configured to cover interfaces, cracks, crevices, and other structural aspects of the prosthetic valve 100 that may contribute to thrombus formation when the prosthetic valve 100 is implanted. And in some instances, as discussed further herein, the jacket 300 is configured to include one or more fillets, which help facilitate smooth transitions between the jacket 300 and the leaflet 310. Thus, the jacket 300 covers various aspects of the prosthetic valve and includes features and/or geometries, the combination of which operate to help avoid thrombosis (e.g., by reducing cracks, gaps, crevices, and stagnate blood regions) and help enhance the biocompatibility of the leaflet frame 200 and the prosthetic valve 100.

FIG. 4B is a second view of an illustration of the jacket 300 and prosthetic valve 100 shown in FIG. 4A. As shown in FIG. 4B, the first portion 302 of the jacket 300 includes an outflow jacket height 410 and the second portion 304 of the jacket 300 includes an inflow jacket height 412. The jacket 300 can facilitate tissue growth relative to the prosthetic valve 100. For example, tissue overgrowth over the leaflet frame 200 can be promoted by the jacket 300. In some examples, the jacket 300 promotes tissue overgrowth to the leaflet 310. The outflow jacket height 410 and/or the inflow jacket height 412 are optionally tailored to avoid ingrowth of tissue onto the leaflets 310, but to promote tissue ingrowth onto the jacket 300. Thus, the jacket 300 can be configured to create tissue ingrowth boundaries (e.g., ingrowth stops prior to reaching the leaflets 310). As discussed in greater detail below, in some instances, minimizing the outflow jacket height 410 helps minimize stagnate blood regions on the outflow side of the leaflets 310, such as between the leaflets 310 and the outflow jacket portion, which helps minimize thrombus formation. However, minimizing the outflow jacket height 410 may increase the potential for surrounding tissue to proliferate radially inwardly across the outflow jacket portion toward the leaflets 310. That is, decreasing the height of the outflow jacket portion reduces the ability of the outflow jacket portion to operate as a boundary to tissue ingrowth, as tissue may proliferate across the outflow jacket portion, as those of skill should appreciate. Thus, in some examples, as explained in greater detail below, the jacket 300 may include an additional feature that is distinct from the outflow jacket height 410 and that operates to prevent or minimize a potential for tissue to proliferate radially inwardly across the outflow jacket portion. For example, the jacket 300 may include one or more flange features that project at least partially radially outwardly from the outflow jacket portion (FIGS. 10A and 10B). The one or more flange features operate as a boundary to tissue ingrowth and proliferation.

In certain instances, the jacket 300 includes a surface having a property predetermined to permit (or even promote) tissue ingrowth, or having a property predetermined to prevent or minimize tissue ingrowth. For instance, in some examples, the surface of the jacket 300 may have a texture, such as a relatively rough texture, that is predetermined to permit or promote tissue ingrowth. Conversely, the surface of the jacket 300 may have a relatively smooth texture that prevents or minimizes tissue ingrowth. In some examples, the surface of the jacket 300 may be modified to achieve the desired surface texture. In some examples, the jacket 300 could be formed of a porous PEEK material (injection moldable and/or machined) or a porous PEKK material (3D printable). Accordingly, the jacket 300 can have a predetermined pore size and density that permits or promotes tissue ingrowth where desired. The jacket 300 can have non-tissue ingrowth regions. In certain instances, at least the pores on the surface of the jacket 300 can be imbibed, coated, or infused to prevent or minimize tissue ingrowth on portions of or all of the jacket 300. For example, the pores on the jacket 300 may be imbibed with a soluble TFE-PMVE copolymer, and the jacket 300 may be solvent welded to a soluble TFE-PMVE copolymer portion or subcomponent on the leaflets 310 to prevent or minimize tissue ingrowth onto or across the leaflets 310 and the jacket 300. In some examples, one or more layers of material, such as the material of which the jacket is formed, may be bonded (e.g., pre-bonded) to one or more portions of the leaflets 310 independent of the jacket being formed about the leaflet frame 200 and/or coupled with one or more portions of the leaflets 310. In some examples, the one or more layers of material may include any of the suitable materials described herein, including any of the materials suitable for forming the jacket discussed herein. In some examples, when forming the jacket about the leaflet frame 200 and/or one or more portions of the leaflet 310, the jacket may be bonded with the one or more layers of material pre-bonded to the leaflets 310, which may provide for a better or more consistent bond between the jacket and the leaflets 310, as those of skill should appreciate.

The jacket 300 can also be advantageous in various respects in that the outflow jacket height 410 and/or the inflow jacket height 412 may be altered, without changing the leaflet frame 200, in response to patient valve size, position, and/or desired flow characteristics. In addition, the jacket 300 encapsulates an interface present between the leaflet frame 200 and the leaflet(s) 310 is configured to isolate the interface from blood flow.

FIG. 4C is a third view of an illustration of the jacket 300 and prosthetic valve 100 shown in FIGS. 4A-B. An interior rim 414 of the jacket 300 is configurable to modify flow characteristics. The interior rim 414, also described as the luminal side of the jacket 300, is configured to alter flow through the prosthetic valve 100 (e.g., in order to prevent regions of stasis behind the leaflets 310 and improve washout throughout the cardiac cycle). In this regard, the jacket 300 and the interior rim 414 may be configured with smooth transitions without 90 degree or perpendicular corners, undercuts, or other features that would not otherwise be seen on any surface that is designed to prevent flow disturbances.

In some examples, as discussed further below, the jacket may be configured to include one or more fillets, which help facilitate smooth transitions between the jacket and the leaflets 310. Thus, in some examples, the jacket may include a fillet on the outflow portion of the jacket and/or on the inflow portion of the jacket. In some examples, the fillet of the jacket 300 extends radially inwardly of the interior rim 414 of the jacket as described further below and defines, at least in part, a transition between the jacket and the leaflet 310. In some non-limiting examples, the fillet may extend between one and three millimeters (1-3 mm) inwardly from the interior rim 414 (e.g., which may also be understood to be consistent with a distance from an interior surface of the wall of the outflow and/or inflow portions of the jacket). Thus, the fillet may alternatively extend inwardly from an inside diameter of the jacket more than three millimeters (3 mm), such as four, five, or even six millimeters, provided that the fillet does not extend so far inwardly that the outflow tract area of the prosthetic valve 100 (e.g., the flow area for fluid passing through the prosthetic valve 100) is occluded or otherwise reduced or constricted to an undesirable area (e.g., not suitable for permitting a desired fluid flow rate through the prosthetic valve 100).

Moreover, it is to be appreciated that the fillet may extend radially inwardly by different amounts at different angular positions. For instance, the fillet may extend inwardly by a first amount (e.g., 3 mm) at a first angular position (e.g., such as at the same angular positions as one or more of the commissure posts 210) and may extend inwardly by a second amount (e.g., 1 mm or 1.25 mm) at a second angular position (e.g., such as at the same angular positions as one or more of the leaflet belly regions 322, equidistant between adjacent commissure posts 210). Thus, in some examples the fillet may be configured such that the amount by which the fillet extends radially inwardly varies about an interior circumference of the fillet (e.g., to produce a scalloped interior circumferential edge of the fillet).

The fillets on the outflow portion of the jacket and the inflow portion of the jacket may be the same or may differ. For instance, in some examples, the outflow and inflow fillets may extend inwardly by different amounts, or may extend inwardly by different amounts at different angular positions. In some examples, the outflow and inflow fillets may have different cross-sectional profiles a given angular positions (e.g., the outflow fillet may have more cross sectional area than the inflow fillet in at a given angular position). This may be attributable to the relative curvatures of the fillets, or, one fillet may be curved while the other fillet is non-curved.

Figure 5A:
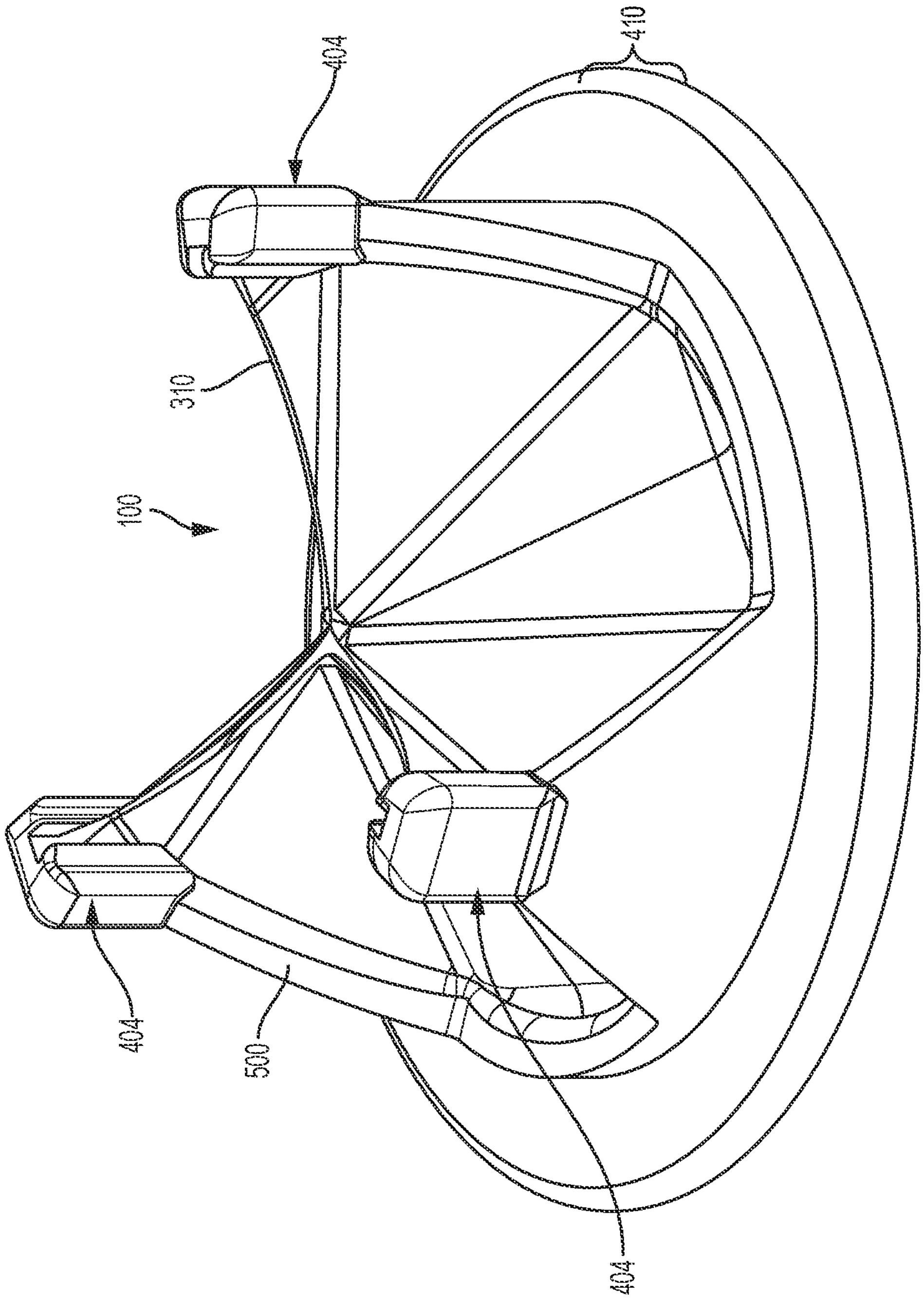
FIG. 5A is an illustration of another example jacket coupled to a prosthetic valve, in accordance with an embodiment.

FIG. 5A is an illustration of another example jacket 500 coupled to a prosthetic valve 100, in accordance with an embodiment. The jacket 500 is molded to the frame (shown in FIG. 5B). The jacket 500 may be molded to the frame in order to enhance the biocompatibility of the frame and the prosthetic valve 100. More specifically, the jacket 500 is configured to cover gaps, spaces, interfaces or other structural aspects that are present in the frame and/or interfaces between the frame and the one or more leaflets 310 attached to the frame to enhance the biocompatibility of the frame. The jacket 500 includes tips 404 that may be atraumatic, and may be equal to a number of leaflets 310 in the prosthetic valve 100.

The uneven, rough, or not smooth surfaces in the frame (e.g., as shown in FIGS. 1-2) may be present in the frame itself and/or may be present in the interfaces between aspects of the prosthetic valve 100. The interfaces, cracks, crevices, and other structural aspects may contribute to thrombus formation when the prosthetic valve 100 is implanted. These structural aspects, for example, can contribute to stagnate blood regions. Stagnate blood regions are negative factors relative to biocompatibility as stagnate blood regions can contribute to thrombus formation. Thus, the jacket 500 enhances the biocompatibility of the frame by covering, wrapping, or hiding the interfaces, cracks, crevices, and other structural aspects.

Figure 5B:
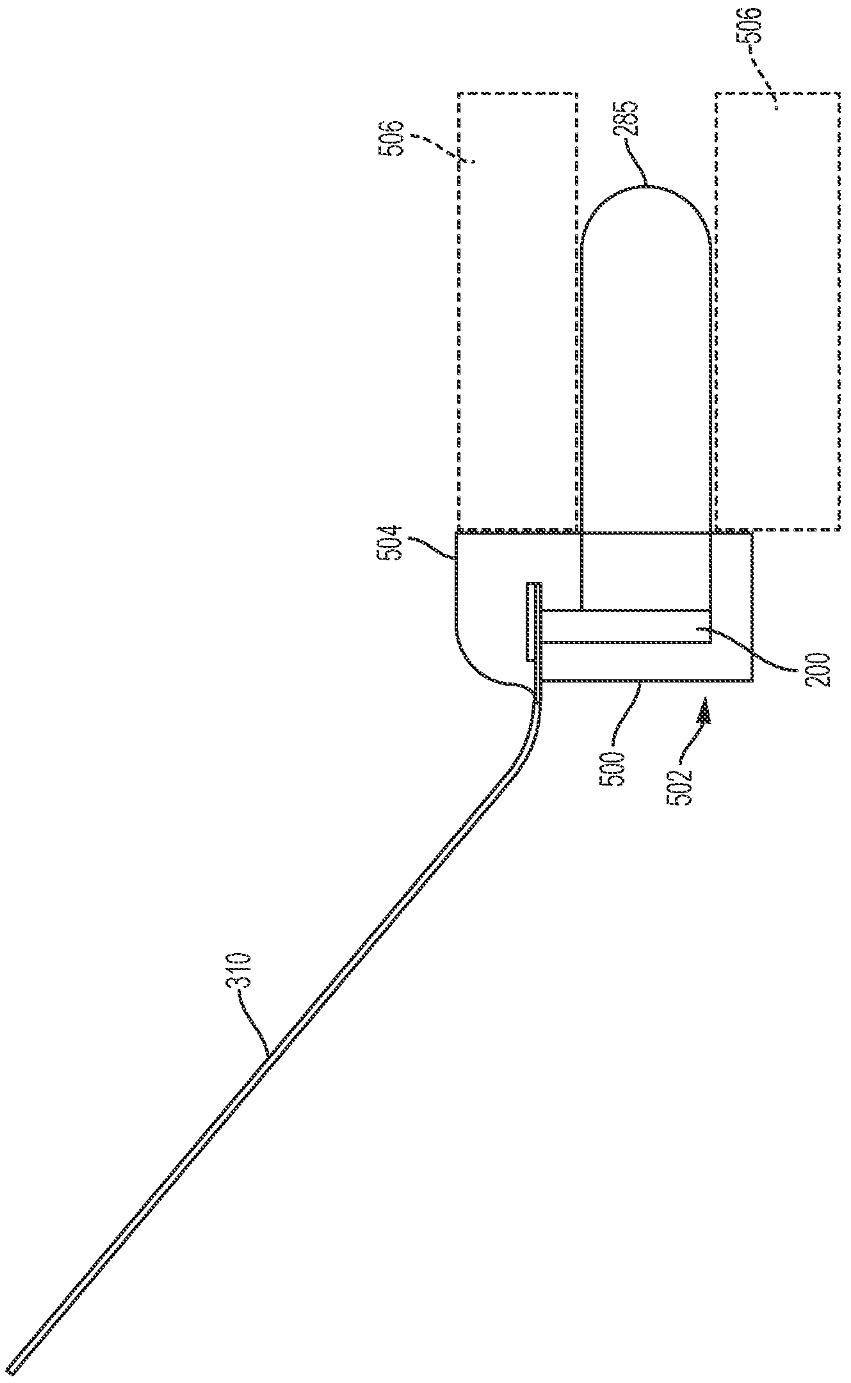
FIG. 5B shows a close-up view of the jacket and prosthetic valve shown in FIG. 5A.

FIG. 5B shows a close-up view of the jacket 500 and prosthetic valve 100 shown in FIG. 5A. In certain instances, the prosthetic valve 100 also includes a sewing cuff 285 arranged about the leaflet frame 200. Micro or macroscopic interfaces are present between the leaflet frame 200 and the leaflets 310 and also between the leaflet frame 200 and the sewing cuff 285. As previously mentioned, the jacket 500 is optionally molded about the leaflet frame 200 to enhance the biocompatibility of the leaflet frame 200 by covering, wrapping, or hiding the interfaces, cracks, crevices, and other structural aspects.

The jacket 500 can include an inflow portion 502 or an outflow portion 504 due to the jacket 500 being molded or overmolded. When implanted, the jacket 500 can separate the leaflet 310 from tissue 506. The inflow portion 502 or the outflow portion 504 include an outflow jacket height 410, as shown in FIG. 5A, to separate the tissue 506 from the leaflet 310. In this manner, tissue ingrowth onto the leaflets 310 is lessened or blocked, as mentioned above. As a result and in certain instances, the jacket 500 is configured to block tissue ingrowth into and onto the one or more leaflets 310 to enhance the biocompatibility of the frame. The inflow or outflow jacket height 410 is tailored to avoid ingrowth of tissue onto the leaflets 310, but can promote tissue ingrowth onto the jacket 500. Thus, the jacket 500 is configured to create tissue ingrowth boundaries (e.g., ingrowth stops prior to reaching the leaflets 310).

As discussed in detail with reference to FIGS. 4A-C, the jacket 500 can also be customizable. An inflow portion of the jacket 500 is configured to prevent regions of stasis behind the leaflets 310 (e.g., on an outflow side of the leaflets) and improve washout throughout the cardiac cycle. In this regard, the jacket 500 has smooth transitions without 90 degree or perpendicular corners, undercuts, or features that wouldn't otherwise be seen on any surface that is designed to prevent flow disturbances.

In certain instances, the leaflets 310 may be formed from a different material or the same material as the jacket 500. The leaflets 310 and the jacket 500 each may be formed of a fluoropolymer.

Figure 6:
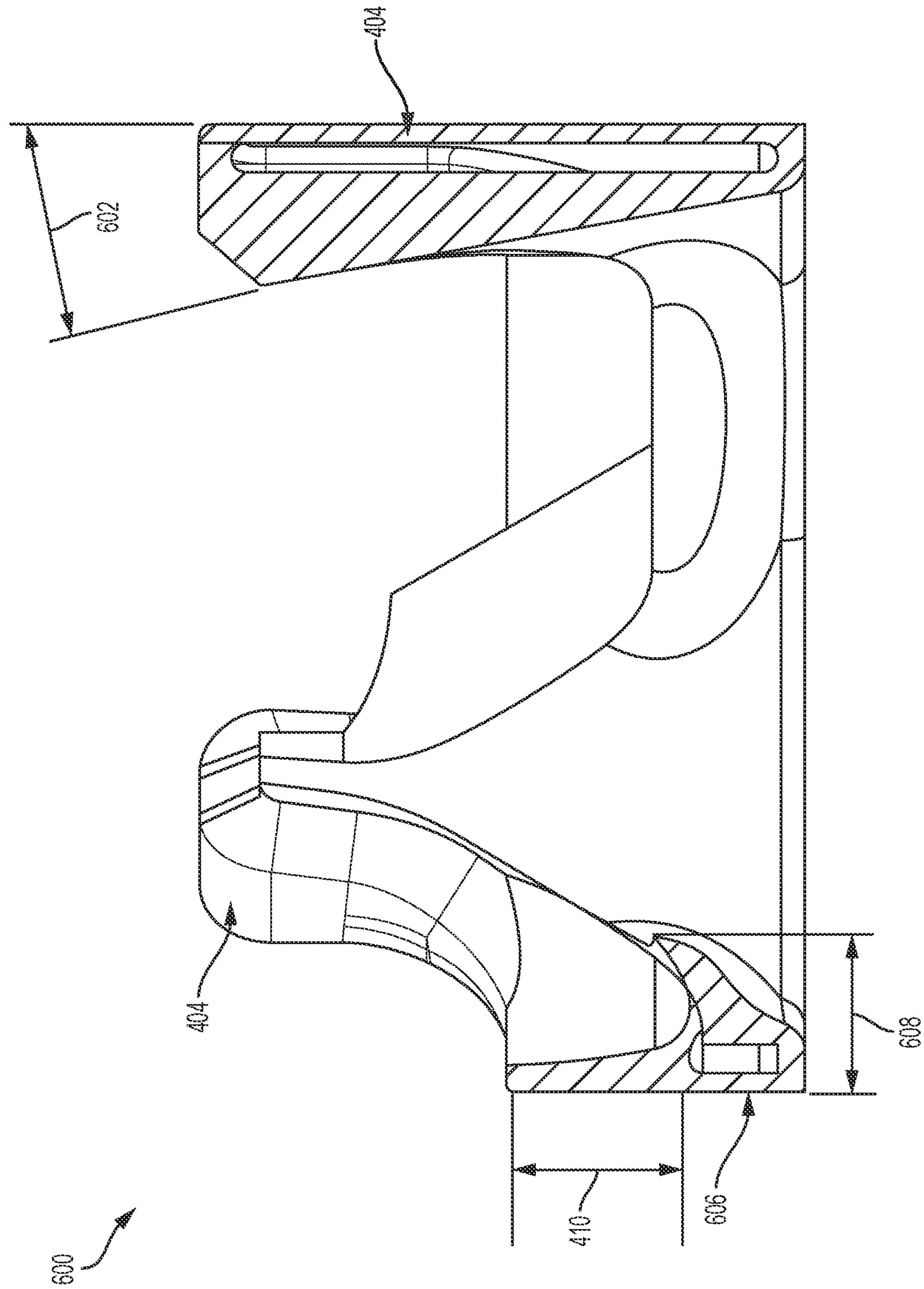
FIG. 6 is an illustration of an example jacket in accordance with an embodiment.

FIG. 6 is an illustration of an example jacket 600 in accordance with an embodiment. The jacket 600 shown in FIG. 6 may be attached or coupled to a prosthetic valve (not shown), as mentioned above. For instance, the jacket 600 may be overmolded to the frame, such as via an injection molding process or via a heat and/or pressure molding process. The jacket 600 includes tips 404 that include are tapered at an angle 602. The tapered tips 404 are configured to restrict an outflow circumference of the prosthetic valve when the leaflets (not shown) are opened. When opened, the leaflets extend from and contact the tapered tips 404 and form approximately a circumference for the blood flow (e.g., between 5% and 25% smaller than if the tips 404 were not present) parallel to the blood flow direction. The tapered tips 404 are configured to create a flow state that promotes washing behind the leaflets, and thus reduced thrombosis formation risk, for example. For example, the tapered tips 404 can promote blood mixing behind the leaflets and lessens dead space. In addition, the tapered tips 404 help promote closure of the leaflets. The tapered tips 404 help promote leaflets configurations do not open further than necessary, and therefore, the blood flow loss that may occur as a result of the narrowed opening by such a nozzle effect is lessened.

As discussed in further detail above, the jacket 600 also includes an outflow jacket height 410 to separate the tissue from the leaflets. In this manner, tissue ingrowth onto the leaflets is lessened or blocked. As a result and in certain instances, the jacket 600 is configured to block tissue ingrowth into the one or more leaflets to enhance the biocompatibility of the frame. The inflow or outflow jacket height 410 is tailored to help avoid ingrowth of tissue onto the leaflets, but can promote tissue ingrowth onto the jacket 600. Thus, the jacket 600 is configured to create tissue ingrowth boundaries (e.g., ingrowth stops prior to reaching the leaflets).

Figure 7B:
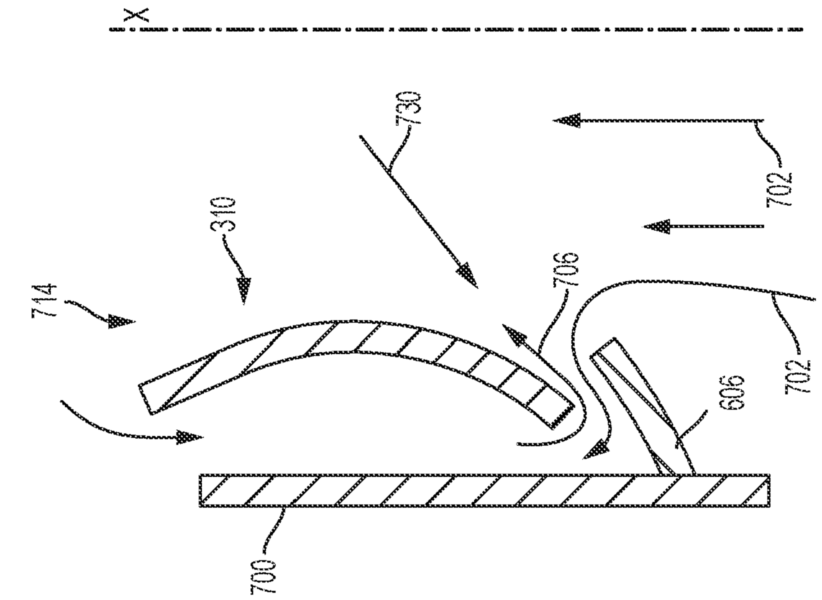
FIG. 7B is a schematic cross-sectional illustration of the jacket and prosthetic valve, shown in FIG. 7A, in an open position.

The jacket 600 can include a shelf 606 arranged on an inflow portion of the jacket 600. The shelf 606, as discussed in further detail with reference to FIGS. 7A-B, is configured to recirculating blood flow behind the leaflets to prevent blood stagnating.

The device shown in FIG. 6 is provided as an example of the various features of the jackets, and, although the combination of those illustrated features is clearly within the scope of the disclosure, that example and its illustration is not meant to suggest the inventive concepts provided herein are limited from fewer features, additional features, or alternative features to one or more of those features shown in FIG. 6. For example, in various embodiments, the tapered tips 404 and/or the shelf 606 of the jacket 600 shown in FIG. 6 may be components of the jackets depicted in FIGS. 3-5.

Figure 7A:
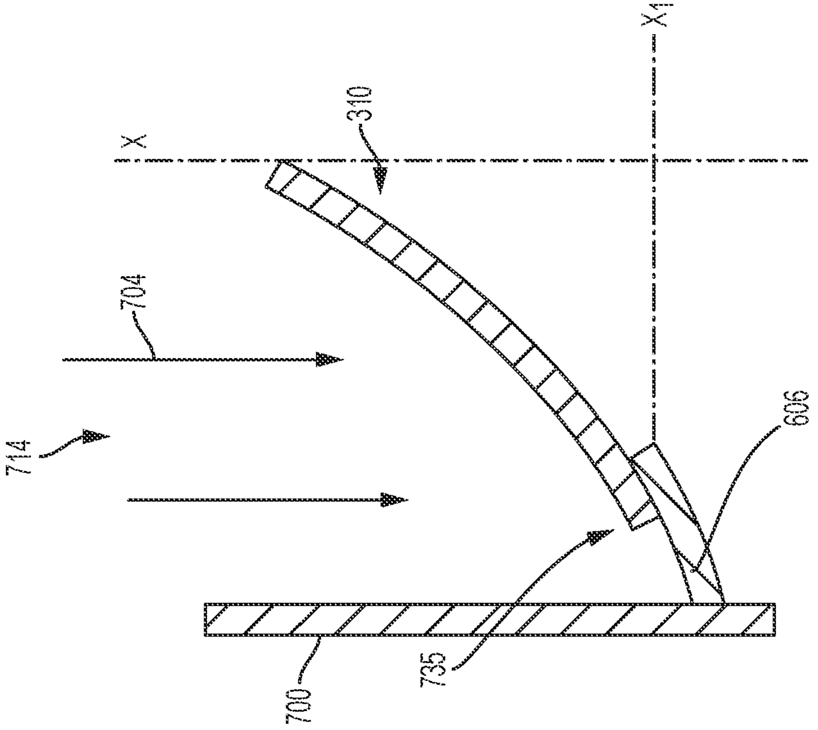
FIG. 7A is a schematic cross-sectional illustration of a jacket having a shelf and a prosthetic valve in a closed position, in accordance with an embodiment.

FIG. 7A is a schematic cross-sectional illustration of a jacket 700 having a shelf 606 and a leaflet 310 of a prosthetic valve (e.g., similar to the prosthetic valve 100) in a closed position, in accordance with an embodiment. FIG. 7B is a schematic cross-sectional illustration of the jacket 700 and leaflet 310, shown in FIG. 7A, in an open position. The jacket 700 covers or encapsulates a frame to which the leaflet 310 is attached. The jacket 700 is annular, that is, it defines a cylinder having a lumen 714 having an axis X and a plurality of tips (e.g., as shown in FIG. 6) extending parallel to the axis X that are spaced from one another.

In the closed position shown in FIG. 7A, the leaflet 310 has a leaflet overlap region 735 with the shelf 606 preventing fluid flow through the lumen 714 in the retrograde direction 704. During forward flow 702 in the forward direction when the leaflet 310 is not in the closed position (when the inflow pressure is greater than the outflow pressure), the leaflet 310 moves away from the shelf 606 to define a gap 730 therebetween.

The gap 730 formed between the leaflet 310 and the shelf 606 when the leaflet 310 is not in the closed position allows fluid adjacent the leaflet 310 to pass through the gap 730 during forward flow 402 in the forward direction through the lumen 714. That is, the recirculating flow behind the leaflet 710 may pass through the gap 730 preventing the recirculating flow from slowing down or stagnating behind the leaflet 310. Further, the gap 730 also allows forward flow 402 to pass through the gap 730 from the first inflow side 713 and the second inflow side 722 further disrupting and displacing the recirculating flow behind the leaflet 310 to downstream of the leaflet 310. Thus, blood behind the leaflet 310 is less likely to clot or form thrombus.

Figure 8A:
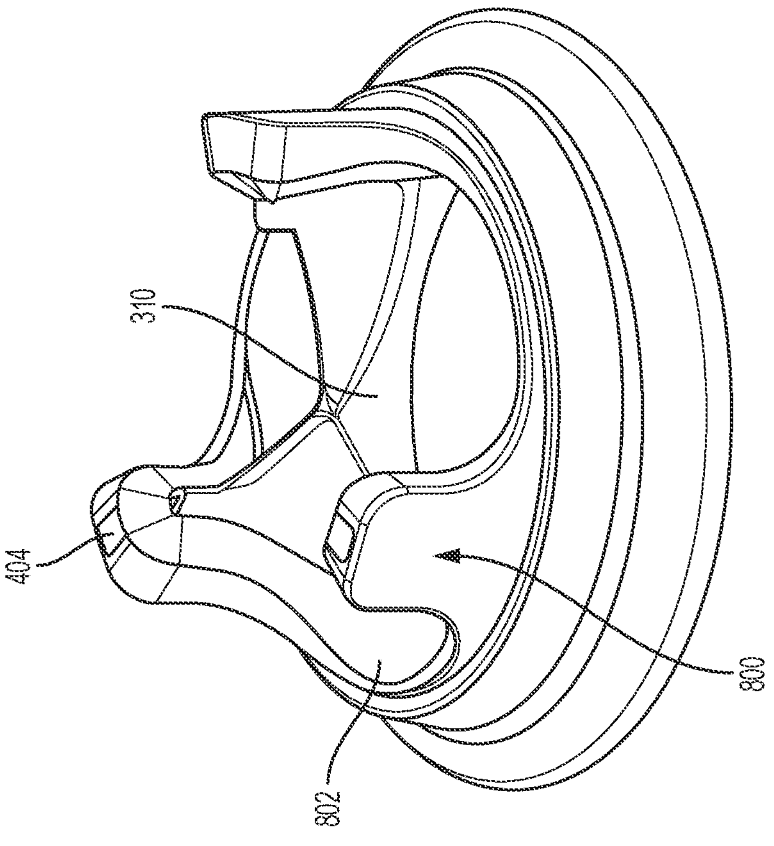
FIGS. 8A and 8B are first and second views of a jacket, in accordance with an embodiment.
Figure 8B:
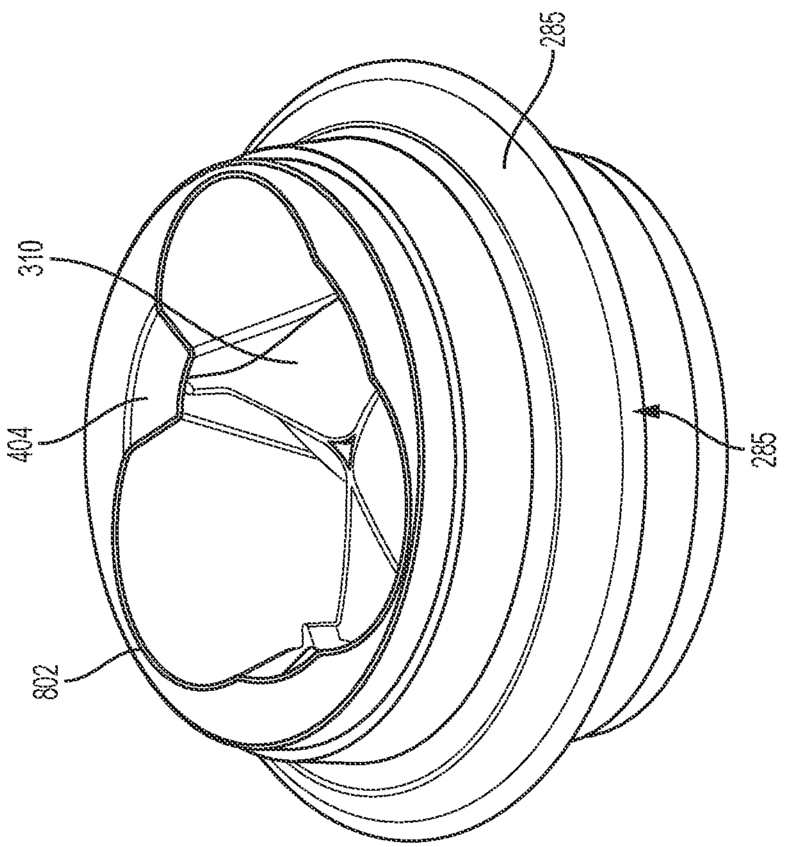

FIGS. 8A and 8B show first and second views of a jacket 800, in accordance with some embodiments. FIGS. 8A and 8B show the jacket 800 and prosthetic valve combination with the jacket 800 completely covering or encapsulating a leaflet frame. The sewing cuff 285 is shown exposed. The sewing cuff 285 can have any shape and can be located along any portion of the height of the jacket 800.

As shown in FIGS. 8A and 8B, the jacket 800 defines a wall 802 (also described as a radial cover) between the plurality of tips 404 (also described as post cover portions). As shown in FIG. 8A, the wall 802 has a relatively low height (e.g., lower than the coaptation region of the leaflets 310). FIG. 8B has a relatively higher wall that extends distally beyond the leaflets 310 (e.g., to a height of the plurality of tips 404, or post cover portions). In some examples, the height of the wall 802 can be selected to mitigate tissue ingrowth (e.g., blocking ingrowth to the leaflets 310), to protect the leaflets 310 from other anatomical impingement (e.g., tissue around the native valve orifice) into the area of the leaflets 310, and/or to modify a flow profile out of the leaflets 310, or to achieve other performance features as desired, such as regions of stasis (also referred to as stagnant blood regions) on the outflow side of the leaflets as mentioned above. In one non-limiting example, the wall 802 may extend between four (4) and five (5) millimeters above the leaflet frame 200.

FIGS. 9A and 9B show a jacket 900. FIG. 9B is a cross sectioned view taken along line 9B-9B of FIG. 9A. As shown, the jacket 900 includes a first portion 902 (an outflow jacket portion) having an outflow jacket height 910 that is minimized to help minimize stagnate blood regions on the outflow side of the leaflets 310 between the leaflets 310 and the first portion 902. The outflow jacket height 910 may be defined between the sewing cuff 285 and the portion of the jacket 900 extending adjacent the leaflet window base 225 of the leaflet frame 200 (also described as an outflow edge 908), as shown. That is, as mentioned above, the outflow jacket height 910 may be determined relative to the sewing cuff 285 (e.g., based on an offset between the outflow edge 908 relative to the sewing cuff 285). The outflow jacket height 910 may also be determined relative to the outflow side of the leaflets 310. The outflow edge 908 extends generally parallel to a jacket inflow edge 914 (which extends generally parallel to the leaflet frame first edge 227). In various examples, the jacket 900 further includes a second portion 904 (an inflow jacket portion) as shown.

In some examples, the jacket 900 further includes smooth transitions between the jacket 900 and the leaflet 310, which helps minimize cracks, gaps, and crevices. For instance, as shown in FIG. 9B, the jacket 900 includes an outflow fillet 920 and an inflow fillet 922. The outflow fillet 920 defines a transition between the outflow edge 908 of the first portion 902 of the jacket 900, and is thus situated between the outflow edge 908 of the first portion 902 of the jacket 900 and a transition region 924 defined where the jacket 900 terminates into the outflow side of the leaflet 310. By comparison, the inflow fillet 922 defines a transition between the jacket inflow edge 914 of the second portion 904 of the jacket 900, and is thus situated between the jacket inflow edge 914 of the second portion 904 of the jacket 900 and a transition region 926 defined where the jacket 900 terminates into the inflow side of the leaflet 310. The fillets may include a linear or nonlinear profile (e.g., a surface of the fillet may be linear or nonlinear). Fillets or similar geometries such as these help provide for a smooth transition between the leaflets 310 and the jacket 90, such as the outflow edge 908 of the jacket 900. These types of smooth transitions help minimize gaps, crevices, and stagnate blood regions and thus thrombus formation, as mentioned above.

In some examples, a jacket inflow edge 914 defines a leading edge of the inflow side of the jacket 900, in situ. As similarly discussed above with respect to the jacket 900, the jacket 900 further includes an inflow jacket height 912 (generally defined between the sewing cuff 285 and the jacket inflow edge 914, as shown). Likewise, the outflow jacket height 910 and/or the inflow jacket height 912 may be increased or decreased (also referred to herein as being altered) to accommodate particulars of patient valve size, position, and/or desired flow characteristics, without requiring a change in the profile of the leaflet frame 200. Thus, a given leaflet frame 200 can be utilized in association with a first jacket having a first outflow jacket height and/or a first inflow jacket height, while the same leaflet frame 200 can be utilized in association with a second jacket having a second, different outflow jacket height (larger or smaller than the first outflow jacket height) and/or a second inflow jacket height (larger or smaller than the first inflow jacket height).

Moreover, consistent with the disclosure above, the jacket 900 can facilitate tissue growth relative to the prosthetic valve 100, which helps promote biointegration. The jacket 900 may be configured to permit tissue ingrowth across or along one or more regions thereof (e.g., such as along an outer surface 916 and/or sewing cuff 285), while discouraging, prohibiting, or minimizing the potential for ingrowth along one or more other regions thereof (e.g., such as along an outflow edge 908 and/or fillet portion). In some examples, the outflow jacket height 910 and/or the inflow jacket height 912 remain tailored to avoid, minimize, or prevent tissue from proliferating onto the leaflets 310. In some examples, avoiding, minimizing, or preventing ingrowth of tissue onto the leaflets is accomplished by providing a jacket 900 having an inflow jacket height 912 of sufficient height to operate as a barrier that helps resist a proliferation of tissue across the outflow edge 908 and radially inwardly toward the leaflets 310.

In addition to or as an alternative to controlling tissue ingrowth via outflow jacket height, the jacket 900 may be configured to include one or more projections or flange elements 918 that extend from the jacket 900 and operate as tissue proliferation barriers. These flanges or projections are configured to help obstruct, minimize, or prevent tissue from proliferating across one or more portions of the jacket 900, including from proliferating onto and growing into the leaflets 310. As shown in FIG. 10B, a flange element 918 extends from the first portion 902 of the jacket 900 and projects at least partially radially outwardly therefrom. The configuration of flange element 918 helps prevent, obstruct, or minimize a potential for tissue to proliferate across the outflow edge 908 of the jacket 900. The flange element 918 thus operates as a boundary against tissue ingrowth. As shown, the flange element 918 projects or extends radially outwardly from the jacket 900 between the outflow side of the leaflets 310 and the outer surface 916 of the jacket 900. The configuration shown in FIGS. 10A and 10B is thus configured to provide for tissue ingrowth and attachment in one or more of the sewing cuff 285 and the outer surface 916 of the jacket 900, while still minimizing a potential for tissue to proliferate radially inwardly across the outflow edge 908 and onto the leaflets 310, despite the relatively low outflow jacket height 910.

It is to be appreciated that these flanges or projections can be incorporated into the jacket 900 and can operate to obstruct, minimize, or prevent tissue ingrowth without also requiring an increase in the outflow jacket height 910. For example, a first jacket including a first jacket portion (an outflow jacket portion) having a first height, and not including a flange element may be configured to promote tissue ingrowth and proliferation radially inwardly across the jacket. By comparison, a second jacket including a second jacket portion (an outflow jacket portion) having the first height and including a flange element may be configured to obstruct tissue ingrowth and proliferation radially inwardly across the flange element and thus across the jacket.

Accordingly, it is thus to be appreciated that the jacket 900 may be configured to minimize an outflow jacket height (e.g., to minimize a formation of stagnate blood regions) while still minimizing a potential for tissue to proliferate across the jacket toward leaflets of the prosthetic valve (e.g., which helps permit tissue ingrowth in designated regions of the jacket without permitting tissue to proliferate across the jacket and onto the leaflets).

The jacket 900 may include a continuous flange element or may include a plurality of discrete flange elements 918. For example, as shown in FIG. 10A, the jacket 900 includes a plurality of discrete flange elements 918, each of which is separated from an adjacently situated discrete flange element 918 by a tip 901 (or commissure post cover) of the jacket 900. That is, the jacket 900 may be configured such that one or more of the plurality of discrete flange elements 918 extend along those portions of the jacket 900 between tips 901. Thus, it is to be appreciated that each discrete flange element 918 generally extends along or adjacent to (or follows a path corresponding to) one or more of the leaflet window base 225 and the leaflet window sides 223 of the leaflet frame 200.

Alternatively, the flange element 918 of the jacket 900 may extend continuously about the jacket 900. That is, the jacket 900 may be configured such that the flange element 918 is not interrupted by the tips 901 of the jacket 900. Instead, in some examples, the flange element 918 may extend along an outflow edge of the jacket 900 including along the tips 901 of the jacket 900, such that the flange element 918 forms a continuous element having no beginning and no end or termination point. Thus, it is to be appreciated that, in such examples, the flange element 918 generally extends along or adjacent to (or follows a path corresponding to) the leaflet window bases 225, the leaflet window sides 223, and the commissure posts 210 and post lateral sides 213 of the leaflet frame 200.

Figure 15:
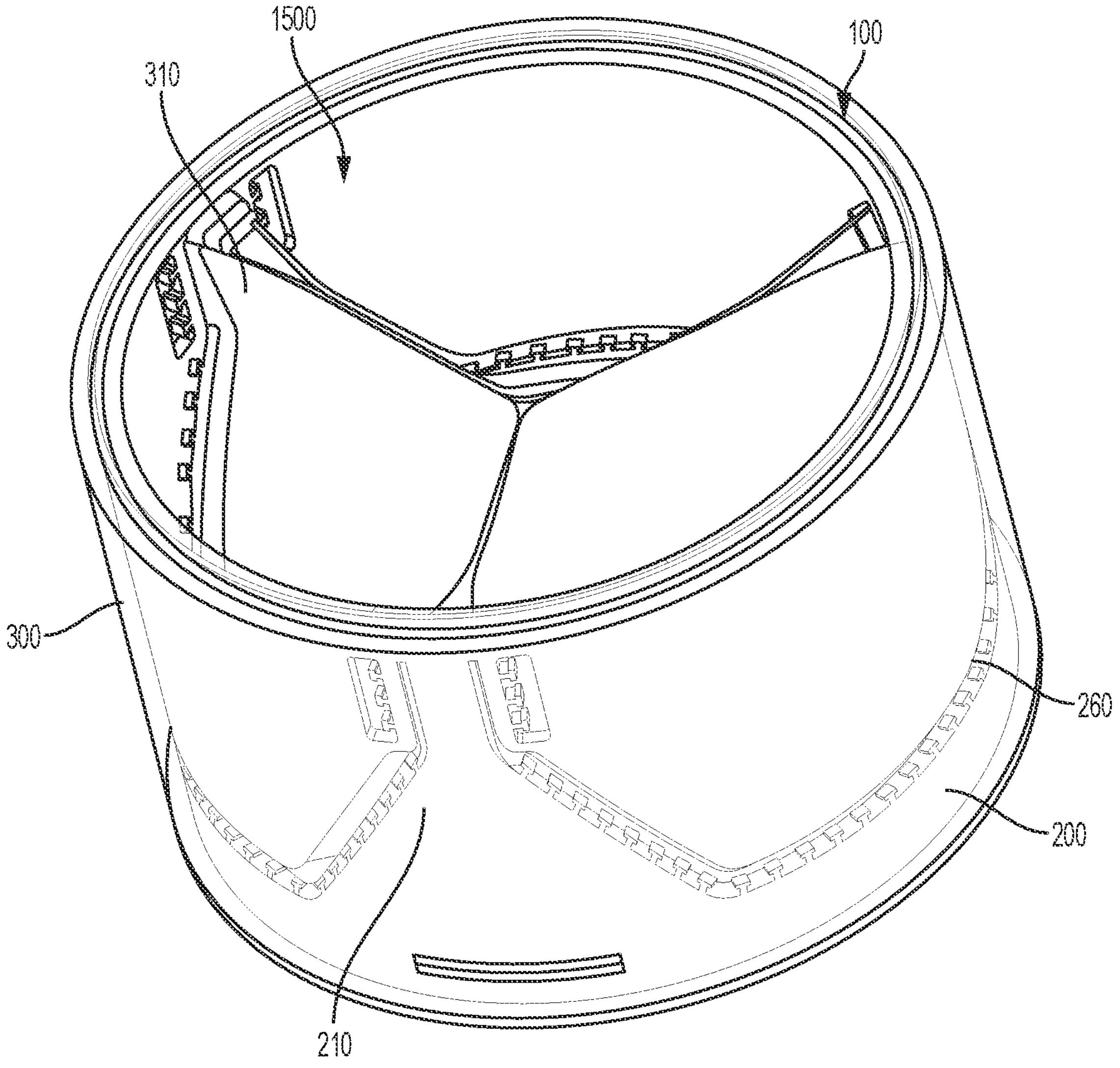
FIG. 15 is a perspective view of an illustration of an example jacket coupled to a prosthetic valve, in accordance with an embodiment.

FIG. 15 is a perspective view of an illustration of an example jacket 300 coupled to a prosthetic valve 100, in accordance with an embodiment. The components of the prosthetic valve 100 (e.g., shown in greater detail in FIG. 1) include a plurality of leaflets 310 and a leaflet frame 200 that includes a plurality of commissure posts 210 flanked on each side by leaflet window frame element(s). The leaflet frame 200 is operable to mechanically couple and support the leaflets 310 by way of, at least in part, a plurality of leaflet frame projections 260.

The jacket 300 may be joined to the leaflet frame 200 in order to enhance the biocompatibility of the leaflet frame 200 and the prosthetic valve 100. More specifically, the jacket 300 is configured to cover gaps, spaces, interfaces or other structural aspects that are present in the leaflet frame 200 and/or interfaces between the leaflet frame 200 and the one or more leaflets 310 attached to the leaflet frame 200 to enhance the biocompatibility of the leaflet frame 200 as discussed in further detail above (e.g., with reference to FIGS. 3A-B). In some examples, the jacket 300 additionally helps maintain mechanical attachment of the leaflets 310 to the leaflet frame 200, including the leaflet frame projections 260. In addition, the jacket 300 may be configured to include smooth transitions for the prosthetic valve 100 to help minimize gaps and crevices, and thus help minimize stagnate blood regions and/or thrombus formation. In addition and as shown, the jacket 300 may extend to cover (outflow side) ends of the commissure posts 210. The jacket 300 being formed and configured in this manner may help minimize stagnate blood regions and/or thrombus formation by filling a gap 1500 behind the outflow side of the leaflets 310 and the leaflet frame 200.

Figure 16:
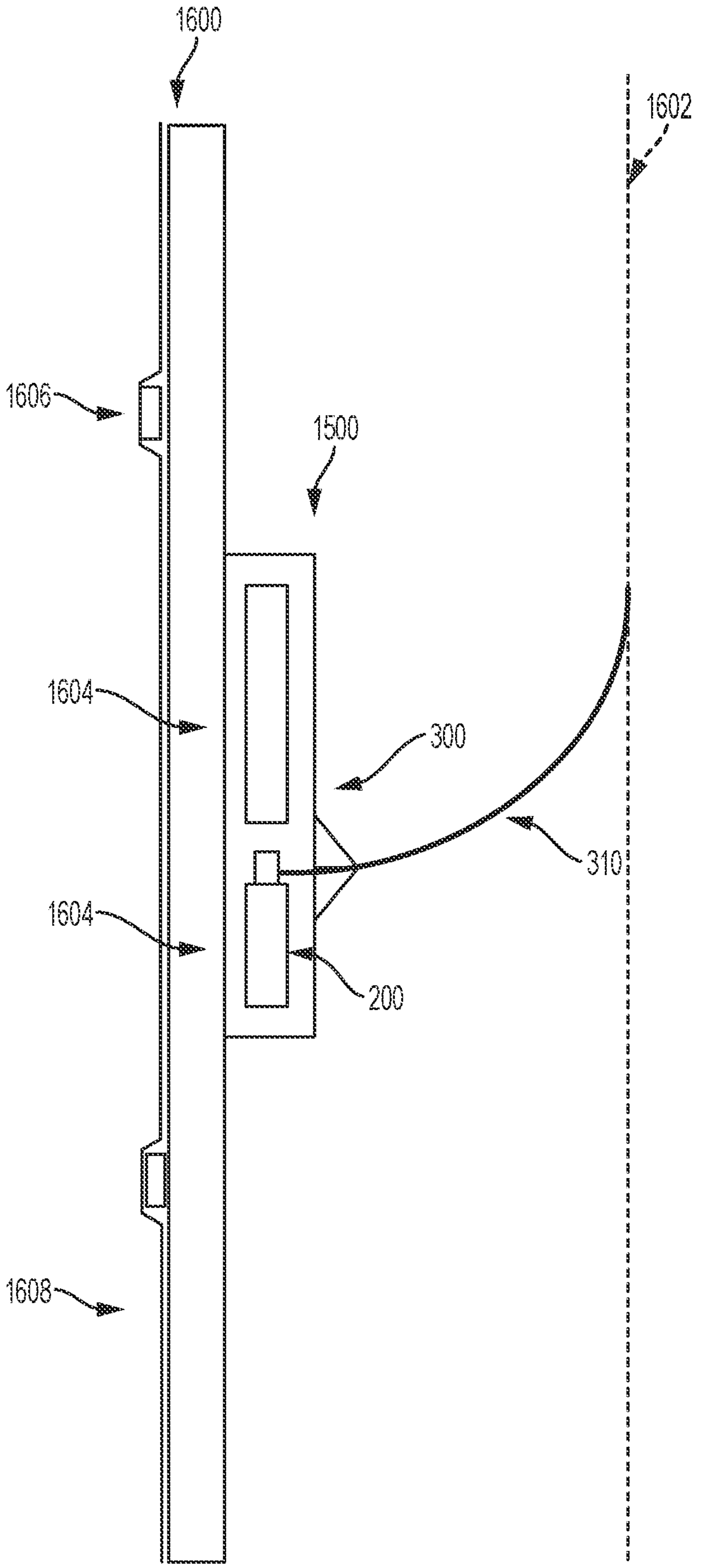
FIG. 16 is a cross-sectional illustration of the jacket and the prosthetic valve shown in FIG. 15 as arranged in a conduit, in accordance with an embodiment.

In certain instances, the prosthetic valve 100 (with the jacket 300) may be directly implanted into a patient and in other instances, the prosthetic valve 100 may be arranged within a conduit as shown in FIG. 16.

FIG. 16 is a cross-sectional illustration of the jacket 300 and the prosthetic valve 100 shown in FIG. 15 as arranged in a conduit 1600, in accordance with an embodiment. The prosthetic valve 100 is arranged within the conduit 1600 such that the leaflets 310 extend into the conduit 1600 and toward the center 1602 of the conduit 1600. The prosthetic valve 100 may be coupled or adhered to an interior surface of the conduit 1600. At the portion of the conduit 1600 to which the prosthetic valve 100 is coupled or adhered, the conduit 1600 may be densified as compared to the other portions of the conduit 1600 to include a densified portion 1604.

The densified portion 1604 of the conduit 1600 is densified and/or rigidified such that the conduit 1600 retains its shape during handling and use. Densification refers to a process of selectively making the material more dense at selected locations, such as by heating and/or pressure. In certain embodiments, the conduit 1600 is formed from expanded Polytetrafluoroethylene (ePTFE). For ePTFE material that may be relatively porous, the densification process will reduce porosity and make the area more rigid.

In certain instances, an exterior surface of the conduit 1600 may be wrapped with a flexible film 1608 that may enhance longitudinal tensile strength of the conduit 1600 by adding column strength to the conduit 1600.

In certain instances, the conduit 1600 may include one or more radiopaque markers 1606 to assist in visualizing a location of the prosthetic valve 100 within the conduit 1600 post-procedure under fluoroscopic visualization. The one or more radiopaque markers 1606 can be arranged adjacent to the prosthetic valve 100 on the exterior surface of the conduit 1600.

The prosthetic valve 100 having a wall height extending adjacent or up to ends of commissure posts 210, as shown in FIG. 15, may help minimize stagnate blood regions and/or thrombus formation by extending the gap 1500 behind the outflow side of the leaflets 310 and the leaflet frame 200 within the conduit 1600.

Figure 17:
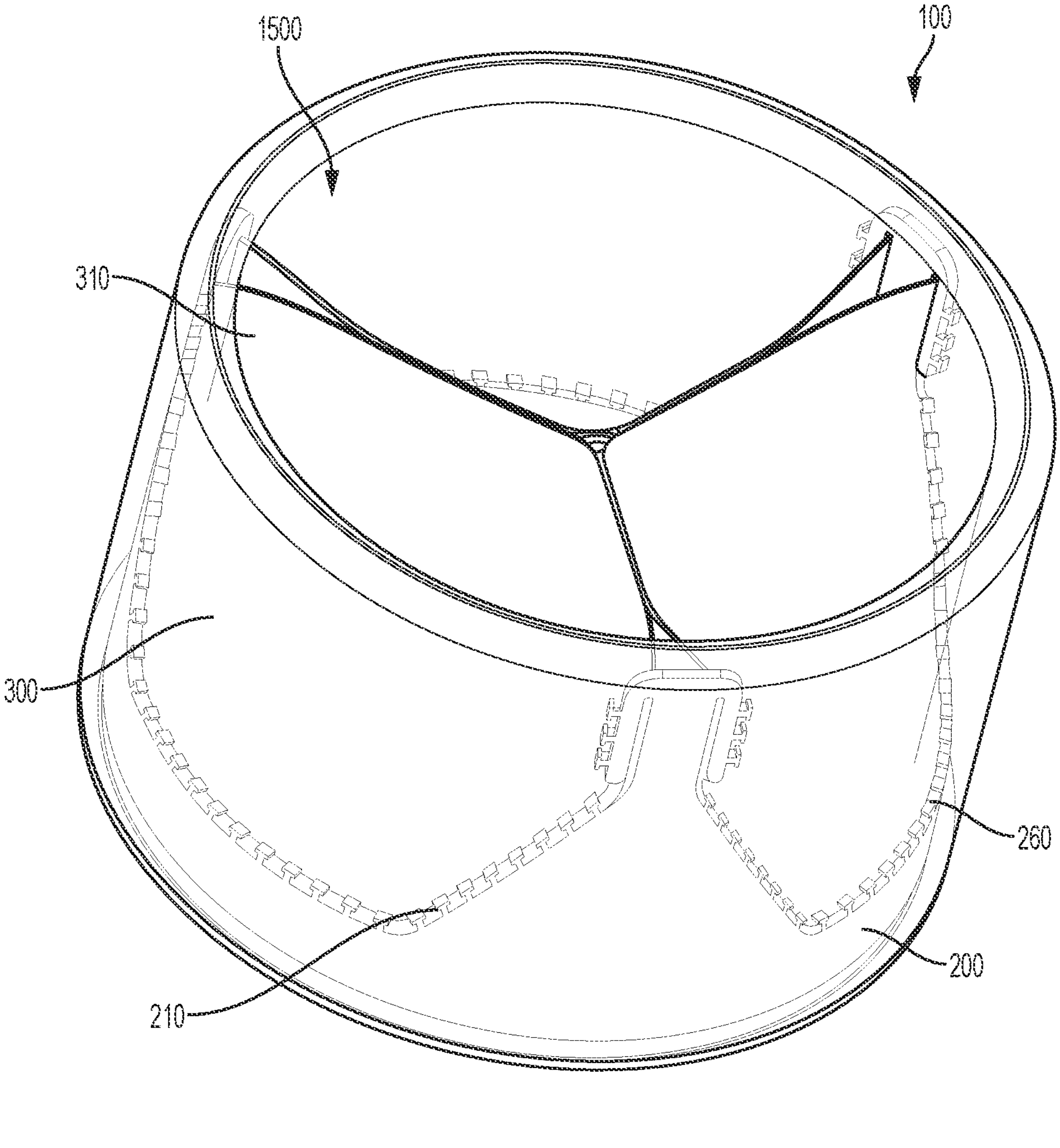
FIG. 17 is a perspective view of an illustration of another example jacket coupled to a prosthetic valve, in accordance with an embodiment.

FIG. 17 is a perspective view of an illustration of another example jacket coupled to a prosthetic valve, in accordance with an embodiment. The components of the prosthetic valve 100 (e.g., shown in greater detail in FIG. 1) include a plurality of leaflets 310 and a leaflet frame 200 that includes a plurality of commissure posts 210 flanked on each side by leaflet window frame element(s). The leaflet frame 200 is operable to mechanically couple and support the leaflets 310 by way of, at least in part, a plurality of leaflet frame projections 260.

The jacket 300 may be joined to the leaflet frame 200 in order to enhance the biocompatibility of the leaflet frame 200 and the prosthetic valve 100. More specifically, the jacket 300 is configured to cover gaps, spaces, interfaces or other structural aspects that are present in the leaflet frame 200 and/or interfaces between the leaflet frame 200 and the one or more leaflets 310 attached to the leaflet frame 200 to enhance the biocompatibility of the leaflet frame 200 as discussed in further detail above (e.g., with reference to FIGS. 3A-B). In some examples, the jacket 300 additionally helps maintain mechanical attachment of the leaflets 310 to the leaflet frame 200, including the leaflet frame projections 260. In addition, the jacket 300 may be configured to include smooth transition for the prosthetic valve 100 help minimize gaps and crevices, and thus help minimize stagnate blood regions and/or thrombus formation.

The components of the prosthetic valve 100 (e.g., shown in greater detail in FIG. 1) include a plurality of leaflets 310 and a leaflet frame 200 that includes a plurality of commissure posts 210 flanked on each side by leaflet window frame element(s). The leaflet frame 200 is operable to mechanically couple and support the leaflets 310 by way of, at least in part, a plurality of leaflet frame projections 260.

The jacket 300 may be joined to the leaflet frame 200 in order to enhance the biocompatibility of the leaflet frame 200 and the prosthetic valve 100. More specifically, the jacket 300 is configured to cover gaps, spaces, interfaces or other structural aspects that are present in the leaflet frame 200 and/or interfaces between the leaflet frame 200 and the one or more leaflets 310 attached to the leaflet frame 200 to enhance the biocompatibility of the leaflet frame 200 as discussed in further detail above (e.g., with reference to FIGS. 3A-B). In addition, the jacket 300 may be configured to include smooth transition for the prosthetic valve 100 help minimize gaps and crevices, and thus help minimize stagnate blood regions and/or thrombus formation. In addition and as shown, the jacket 300 may extend to cover (outflow side) ends of the commissure posts 210. The jacket 300 being formed and configured in this manner may help minimize stagnate blood regions and/or thrombus formation by filling a gap 1500 behind the outflow side of the leaflets 310 and the leaflet frame 200.

In certain instances, the jacket 300 may include an inflow and an outflow portion that couple together about the leaflet frame 200 (e.g., as described above with reference to FIGS. 3A-B). In other instances, the jacket 300 may be a single piece directly coupled or overmolded to the leaflet frame 200. In addition, portions of the jacket 300 may also be coupled or overmolded to portions of the leaflets 310.

In certain instances, the jacket 300 may be formed of a rigid polymer. In certain instances, the jacket 300 may be formed of a fluoropolymer (e.g., a TFE-PMVE copolymer). In these instances, the TFE-PMVE copolymer jacket 300 may bond to the synthetic leaflets 310.

Figure 18:
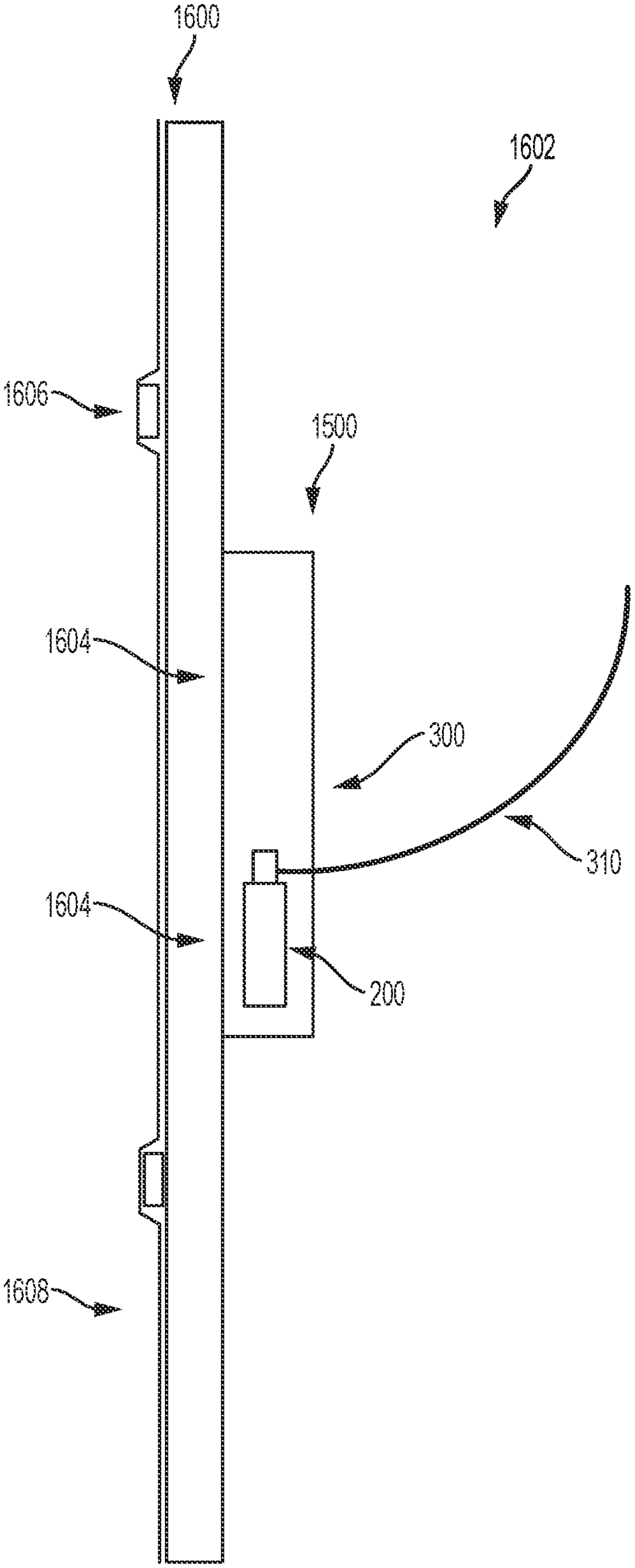
FIG. 18 is a cross-sectional illustration of the jacket and the prosthetic valve shown in FIG. 17 as arranged in a conduit, in accordance with an embodiment.

In certain instances, the prosthetic valve 100 (with the jacket 300) may be directly implanted into a patient and in other instances, the prosthetic valve 100 may be arranged within a conduit as shown in FIG. 18.

FIG. 18 is a cross-sectional illustration of the jacket and the prosthetic valve shown in FIG. 17 as arranged in a conduit, in accordance with an embodiment. The prosthetic valve 100 is arranged within the conduit 1600 such that the leaflets 310 extend into the conduit 1600 and toward the center 1602 of the conduit 1600. The prosthetic valve 100 may be coupled or adhered to an interior surface of the conduit 1600. At the portion of the conduit 1600 to which the prosthetic valve 100 is coupled or adhered, the conduit 1600 may be a densified portion 1604 as compared to the other portions of the conduit 1600 as discussed in detail above. In addition, the conduit 1600 may include one or more radiopaque markers 1606 to assist in visualizing a location of the prosthetic valve 100 within the conduit 1600 post-procedure under fluoroscopic visualization. In addition, the exterior surface of the conduit 1600 may be wrapped with a flexible film 1608 that may enhance longitudinal tensile strength of the conduit 1600 by adding column strength to the conduit 1600.

The prosthetic valve 100 having a wall height extending adjacent or up to ends of commissure posts 210, as shown in FIG. 17, may help minimize stagnate blood regions and/or thrombus formation by extending the gap 1500 behind the outflow side of the leaflets 310 and the leaflet frame 200 within the conduit 1600.

Figure 19:
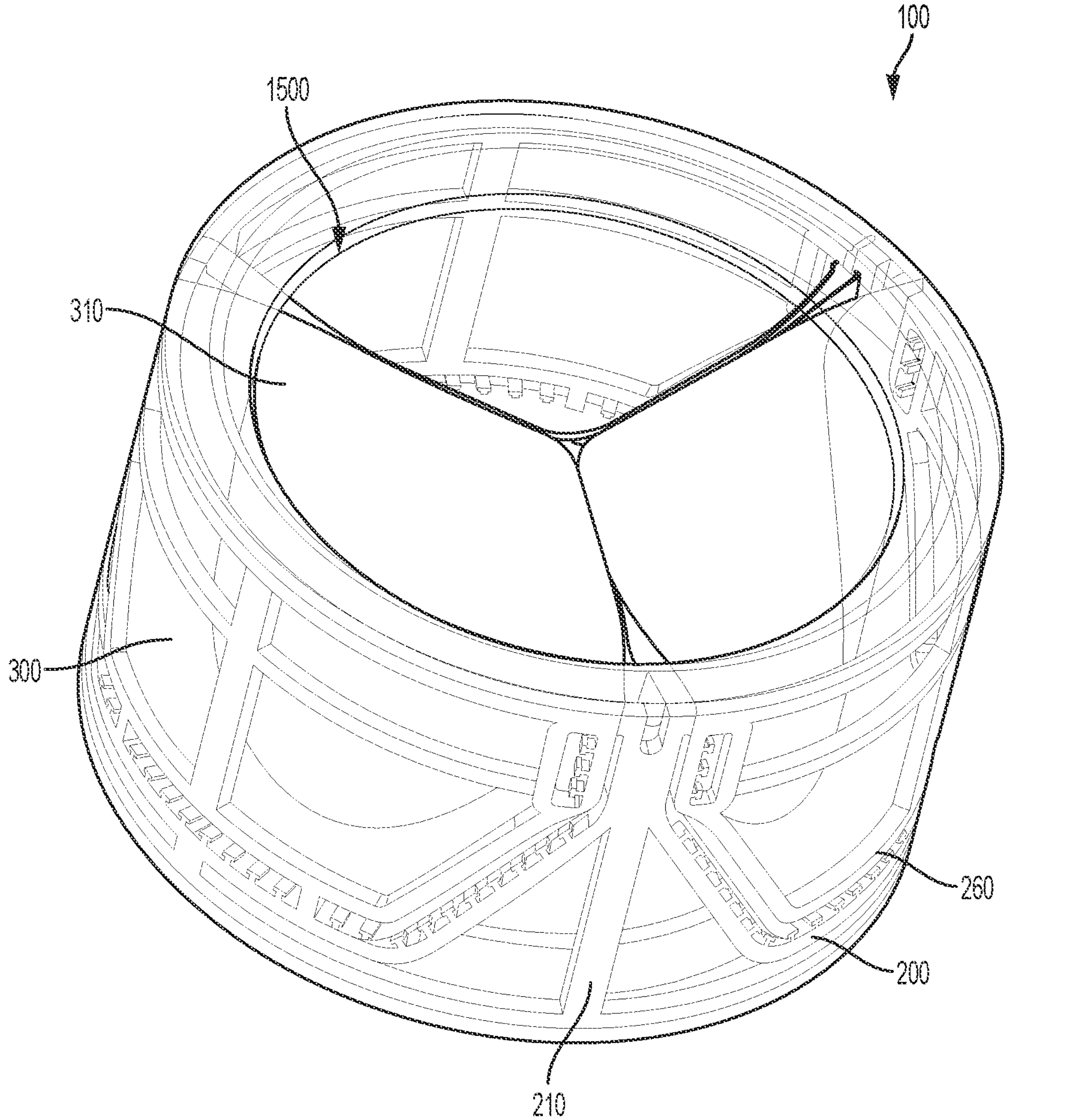
FIG. 19 is a perspective view of an illustration of another example jacket coupled to a prosthetic valve, in accordance with an embodiment.

FIG. 19 is a perspective view of an illustration of another example jacket coupled to a prosthetic valve, in accordance with an embodiment. The components of the prosthetic valve 100 (e.g., shown in greater detail in FIG. 1) include a plurality of leaflets 310 and a leaflet frame 200 that includes a plurality of commissure posts 210 flanked on each side by leaflet window frame element(s). The leaflet frame 200 is operable to mechanically couple and support the leaflets 310 by way of, at least in part, a plurality of leaflet frame projections 260.

The jacket 300 may be joined to the leaflet frame 200 in order to enhance the biocompatibility of the leaflet frame 200 and the prosthetic valve 100. More specifically, the jacket 300 is configured to cover gaps, spaces, interfaces or other structural aspects that are present in the leaflet frame 200 and/or interfaces between the leaflet frame 200 and the one or more leaflets 310 attached to the leaflet frame 200 to enhance the biocompatibility of the leaflet frame 200 as discussed in further detail above (e.g., with reference to FIGS. 3A-B). In certain instances, the jacket 300 may be joined to the leaflet if the leaflet frame 200 is overmolded.

In certain instances, it may be beneficial for the jacket 300 to be formed of a flexible component such as silicone. The jacket 300 may minimize a seam and create a seal with compressive force in gaps between the leaflets 310 and the frame 200 as explained in further detail below with reference to FIGS. 21A-B. In certain instances, portions of the jacket 300 may be formed of different materials. As noted above (e.g., with reference to FIGS. 3A-B), the jacket 300 may include a first portion 302 (an outflow jacket portion) and a second portion 304 (an inflow jacket portion). The inflow portion of the jacket 300, for example, may be formed of a different material than the outflow portion of the jacket 300. In certain instances, the outflow jacket may be formed of more flexible material (e.g., silicone) than the inflow jacket (e.g., a thermoplastic polymer or a rigid material overmolded with silicone).

In certain instances, the prosthetic valve 100 (with the jacket 300) may be directly implanted into a patient and in other instances, the prosthetic valve 100 may be arranged within a conduit as shown in FIG. 18.

Figure 20:
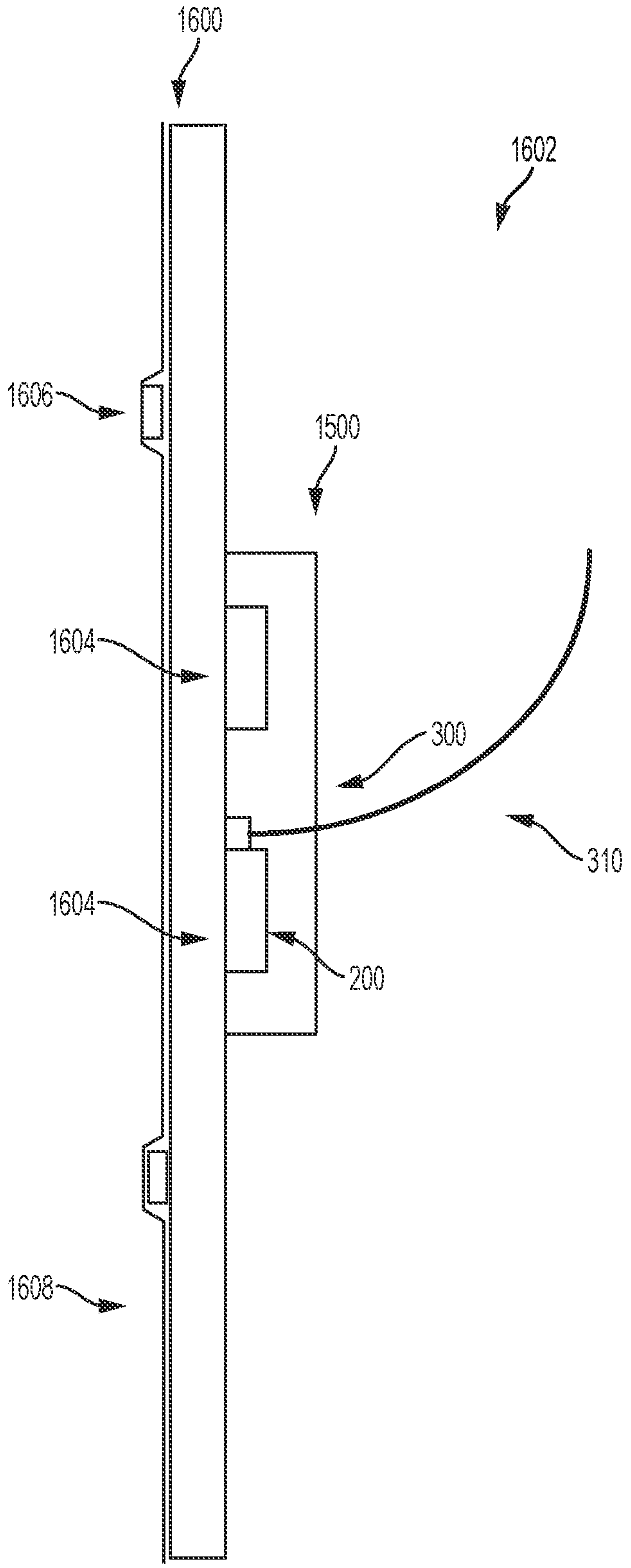
FIG. 20 is a cross-sectional illustration of the jacket and the prosthetic valve shown in FIG. 19 as arranged in a conduit, in accordance with an embodiment.

FIG. 20 is a cross-sectional illustration of the jacket and the prosthetic valve shown in FIG. 19 as arranged in a conduit, in accordance with an embodiment. The prosthetic valve 100 is arranged within the conduit 1600 such that the leaflets 310 extend into the conduit 1600 and toward the center 1602 of the conduit 1600. The prosthetic valve 100 may be coupled or adhered to an interior surface of the conduit 1600. At the portion of the conduit 1600 to which the prosthetic valve 100 is coupled or adhered, the conduit 1600 may be a densified portion 1604 as compared to the other portions of the conduit 160 and the exterior surface of the conduit 1600 may be wrapped with a flexible film 1608 that may enhance longitudinal tensile strength of the conduit 1600 by adding column strength to the conduit 1600.

In certain instances, the conduit 1600 may include one or more radiopaque markers 1606 to assist in visualizing a location of the prosthetic valve 100 within the conduit 1600 post-procedure under fluoroscopic visualization. The one or more radiopaque markers 1606 can be arranged adjacent to the prosthetic valve 100 on the exterior surface of the conduit 1600.

The prosthetic valve 100 having a wall height extending adjacent or up to ends of commissure posts 210, as shown in FIG. 19, may help minimize stagnate blood regions and/or thrombus formation by extending the gap 1500 behind the outflow side of the leaflets 310 and the leaflet frame 200 within the conduit 1600.

Figure 21B:
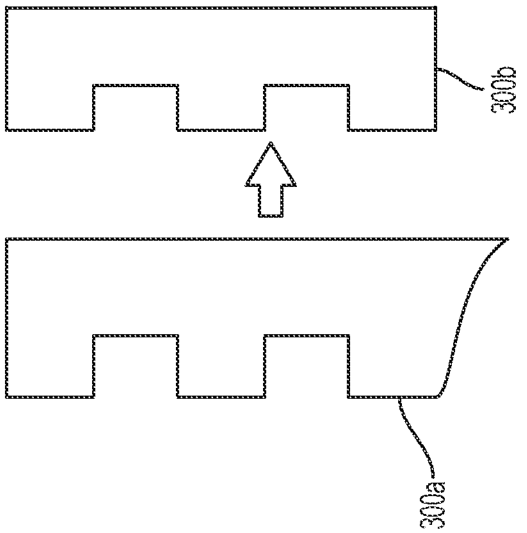
FIG. 21A-B are illustrations of a leaflet arranged within the jacket shown in FIGS. 19-20, in accordance with an embodiment.
Figure 21A:
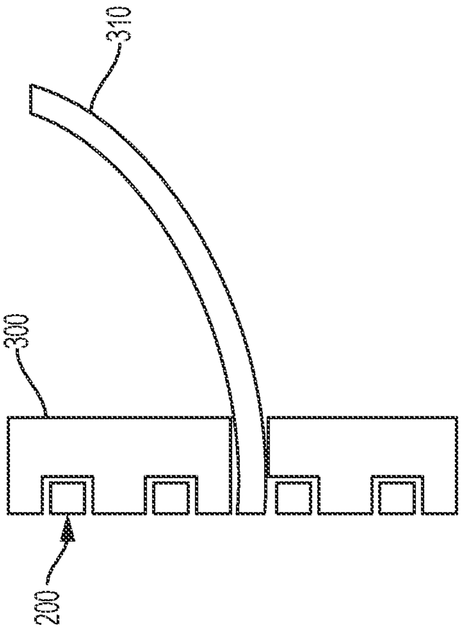

FIG. 21A-B are illustrations of a leaflet 310 arranged within the jacket shown 300 in FIGS. 19-20, in accordance with an embodiment. As shown in FIG. 21B, the jacket 300 is flexible and compressible. The as formed jacket 300*a* may compress longitudinally when arranged with the frame 200 and take the shape of the compressed jacket 300*b*. As shown in FIG. 21A, the jacket 300 may minimize a seam and create a seal with compressive force in gaps between the leaflets 310 and the frame 200.

The prosthetic valves 100 disclosed herein may include a sewing cuff 285 along with a jacket 300 or the prosthetic valves 100 may be placed within a conduit as shown in FIGS. 16, 18, and 20. In addition, the prosthetic valves 100 (and the prosthetic valves 100 arranged within a conduit) may be implanted in the patient outside of the heart such as within blood vessels (e.g., replacement or repair of venous valves) or new valves within blood vessels.

As discussed herein, the leaflets 310 can be made of a polymer or biological tissue. More particularly, the leaflets 310 can also be made from a sheet of polymer material or biological tissue. Pre-shaped polymer leaflets can also be made by starting from a cylinder of polymer material that has been cut into a shape.

The leaflets 310 can comprise any biocompatible material sufficiently compliant and flexible, such as a biocompatible polymer and biological tissue. In various embodiments, the leaflets 310 can comprise a material that is synthetic or of animal origin. The leaflets 310 can comprise a membrane that is combined with an elastomer or an elastomeric material or a non-elastomeric material to form a composite material. The leaflet 310 can comprise, according to an embodiment, a composite material comprising an expanded fluoropolymer membrane that comprises a plurality of spaces within a matrix of fibrils, and an elastomeric material, which the jacket 900 can be formed of. It should be appreciated that multiple types of fluoropolymer membranes and multiple types of elastomeric materials can be combined to form a composite material while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In various examples, any of the leaflets described herein (e.g., leaflets 310) may be formed of a biocompatible, synthetic material (e.g., including ePTFE and ePTFE composites, or other materials as desired). Other biocompatible polymers which can be suitable for use in synthetic leaflets include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

In other examples, such leaflet construct is formed of a natural material, such as repurposed tissue, including bovine tissue, porcine tissue, or the like.

As used herein, the term "elastomer" refers to a polymer or a mixture of polymers that has the ability to be stretched to at least 1.3 times its original length and to retract rapidly to approximately its original length when released. The term "elastomeric material" refers to a polymer or a mixture of polymers that displays stretch and recovery properties similar to an elastomer, although not necessarily to the same degree of stretch and/or recovery. The term "non-elastomeric material" refers to a polymer or a mixture of polymers that displays stretch and recovery properties not similar to either an elastomer or elastomeric material, that is, considered not an elastomer or elastomeric material.

In accordance with an embodiment, the composite material includes an expanded fluoropolymer material made from porous ePTFE membrane, for instance as generally described in U.S. Pat. No. 7,306,729 to Bacino.

The expanded fluoropolymer membrane, used to form some of the composites described, can comprise PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

In accordance with embodiments herein, the leaflet comprises a composite material having at least one porous synthetic polymer membrane layer having a plurality of pores and/or spaces and an elastomer and/or an elastomeric material and/or a non-elastomeric material filling the pores and/or spaces of the at least one synthetic polymer membrane layer. In accordance with other examples, the leaflet further comprises a layer of an elastomer and/or an elastomeric material and/or a non-elastomeric material on the composite material. In accordance with examples, the composite material comprises porous synthetic polymer membrane by weight in a range of about 10% to 90%.

An example of a porous synthetic polymer membrane includes expanded fluoropolymer membrane having a node and fibril structure defining the pores and/or spaces. In some examples, the expanded fluoropolymer membrane is expanded polytetrafluoroethylene (ePTFE) membrane. Another example of porous synthetic polymer membrane includes microporous polyethylene membrane.

The elastomer and/or an elastomeric material and/or a non-elastomeric material may be combined with the expanded fluoropolymer membrane such that the elastomer and/or the elastomeric material and/or the non-elastomeric material occupies substantially all of the void space or pores within the expanded fluoropolymer membrane.

Examples of an elastomer and/or an elastomeric material and/or a non-elastomeric material include, but are not limited to, copolymers of tetrafluoroethylene and perfluoromethyl vinyl ether (TFE/PMVE copolymer), (per)fluoroalkylvinylethers (PAVE), urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing. In some examples, the TFE/PMVE copolymer is an elastomer comprising essentially of between 60 and 20 weight percent tetrafluoroethylene and respectively between 40 and 80 weight percent perfluoromethyl vinyl ether. In some examples, the TFE/PMVE copolymer is an elastomeric material comprising essentially of between 67 and 61 weight percent tetrafluoroethylene and respectively between 33 and 39 weight percent perfluoromethyl vinyl ether. In some examples, the TFE/PMVE copolymer is a non-elastomeric material comprising essentially of between 73 and 68 weight percent tetrafluoroethylene and respectively between 27 and 32 weight percent perfluoromethyl vinyl ether. The TFE and PMVE components of the TFE-PMVE copolymer are presented in wt %. For reference, the wt % of PMVE of 40, 33-39, and 27-32 corresponds to a mol % of 29, 23-28, and 18-22, respectively.

In some examples, the TFE-PMVE copolymer exhibits elastomer, elastomeric, and/or non-elastomeric properties.

In some examples, the composite material further comprises a layer or coating of TFE-PMVE copolymer comprising from about 73 to about 68 weight percent tetrafluoroethylene and respectively from about 27 to about 32 weight percent perfluoromethyl vinyl ether.

In some examples, the leaflet is an expanded polytetrafluoroethylene (ePTFE) membrane having been imbibed with TFE-PMVE copolymer comprising from about 60 to about 20 weight percent tetrafluoroethylene and respectively from about 40 to about 80 weight percent perfluoromethyl vinyl ether, the leaflet further including a coating of TFE-PMVE copolymer comprising from about 73 to about 68 weight percent tetrafluoroethylene and respectively about 27 to about 32 weight percent perfluoromethyl vinyl ether on the blood-contacting surfaces.

As mentioned above, a prosthetic valve may include a valve frame, one or more leaflets, and a jacket. In some examples, the jacket is disposed about one or more portions of the valve frame and/or the leaflets. In some examples, the jacket is coupled to the valve frame. As mentioned above, coupling the jacket with the valve frame may include one or more snap fit interfaces, welds, or other means of attachment. In some such examples, the jacket includes a plurality of distinct portions that are coupled together (either permanently or semi-permanently). In these examples, it will be appreciated that, although the jacket is disposed about the valve frame and a portion of one or more of the leaflets, the jacket and the valve frame, or at least one or more portions thereof, remain unbonded.

In some examples, coupling the jacket with the valve frame includes molding (e.g., insert molding or overmolding) the jacket over the valve frame (such as through one or more heat and/or pressure molding processes). In such examples, it is to be appreciated that the jacket may be molded and remain unbonded to one or more of the valve frame and the leaflets, or alternatively may be molded such that the jacket is bonded with one or more of the valve frame and the leaflets. Bonding the jacket with one or more of the valve frame and the leaflets help minimize cracks, crevices, and other structural aspects of the various interfaces existing between the jacket, and the valve frame and leaflets. And, as mentioned above, minimizing cracks, crevices, and other structural aspects help minimize a potential for thrombus formation. In some examples, creating or forming a bond between the jacket and the leaflets helps minimize a potential for the infiltration of blood components into any space underneath or inside the jackets. In some examples, creating or forming a bond between the jacket and the leaflets helps maintain attachment between the leaflets and the leaflet frame 200. In some examples, as mentioned above, creating or forming a bond between the jacket and the leaflets helps provide a beneficial strain relief for the leaflets in the flexing environment.

As mentioned above, the jackets described herein may be formed of (and thus may be molded from) one or more of a variety of materials including, but not limited to, silicone, Polyether ether ketone (PEEK), expanded Polytetrafluoroethylene (ePTFE), Fluorinated ethylene propylene (FEP), copolymers of tetrafluoroethylene (TFE) and perfluoromethyl vinyl ether (PMVE) (TFE-PMVE copolymer), urethanes, polyimides, thermoplastics, thermosets, 3D printable metals and polymers (stainless steel, titanium, etc.) nylon, or any other biocompatible material suitable for long term blood contact that is dimensionally stable, and does not leech contaminates.

In some examples, as mentioned above, the jacket material may be bonded with one or more of the leaflet material and the valve frame material. In some examples, prior to molding the jacket over the valve frame and the leaflets, one or more fluoropolymer adhesives/materials (e.g., FEP, low-melt FEP, copolymers of tetrafluoroethylene (TFE) and perfluoromethyl vinyl ether (PMVE) (TFE-PMVE copolymer), urethanes, thermoplastics, thermosets) may be pre-bonded to one or more portions of each leaflet (avoids cracks and crevices) and/or one or more portions of the valve frame. In such examples, the jacket material is bonded with the prebonded adhesives/materials on the leaflet and/or the valve frame.

In some examples, the jacket material is integrated into the sewing cuff during the molding process to provide for an integrated sewing cuff. For instance, the sewing cuff may be provided in combination with the valve frame and the leaflets (e.g., as shown in FIGS. 3A-3C) to form a valve assembly (e.g., as shown in part of the exploded views of FIGS. 3A-3C), and the jacket material may be applied thereto through one or more heat and/or pressure processes, as described further below.

A method of making a prosthetic valve, in accordance various embodiments, comprises forming (such as by cutting a metal tube, casting, molding, printing, or the like) a leaflet frame defining leaflet frame windows and one or more leaflet retention surfaces, having commissure posts therebetween, and a plurality of projections spaced apart from each other extending from one or more leaflet retention surfaces. Each leaflet frame projection is configured to couple to a leaflet. The leaflet frame projections can have a projection base portion and a projection head portion, where the projection base portion meets the leaflet retention surface at one side and the projection head portion on the opposite side. Some embodiments of the leaflet frame can further define one or more slots that extend through one or more frame elements that define the leaflet frame windows. Each slot is dimensioned to receive at least a single thickness of the leaflet, e.g., the leaflet attachment region. The slot can be a base receiving slot or a side receiving slot. In addition, each commissure post defines a post slot dimensioned to receive a double thickness of the leaflet. In further embodiments, the frames can comprise one or more attachment slots or other frame openings that defines an internal edge from which leaflet frame projections can extend.

The same or different method can comprise obtaining a sheet or tube of material comprising one or more layers of expanded PTFE composite and cutting a leaflet from the sheet or tube, where one or more apertures are formed in the leaflet attachment region of the leaflet. The apertures can be cut to dimensions suitable for coupling to a leaflet frame projection on a leaflet frame. In particular, the aperture can have a size and shape that is substantially the same as a transverse, cross-sectional size and shape of the projection base portion of the leaflet frame projection. The method can further comprise coupling a leaflet reinforcement to the leaflet and further, cutting the leaflet apertures into both the leaflet and the leaflet reinforcement simultaneously.

In some examples, the method of making a prosthetic valve further includes coupling the leaflet to the leaflet frame (also referred to herein as a valve frame) to form a valve assembly. In some examples, the method may further include associating a sewing cuff with the valve assembly to form a valve assembly including a sewing cuff. In some examples, the sewing cuff may be coupled with the valve assembly, such as via one or more sutures, or other means as discussed above. In some instances, the sewing cuff may be frictionally retained on the leaflet frame, or disposed about a flange extending from the valve frame (e.g., as shown in FIGS. 9A-10B), and then secured to the valve assembly during the overmolding process, for example.

Figure 11A:
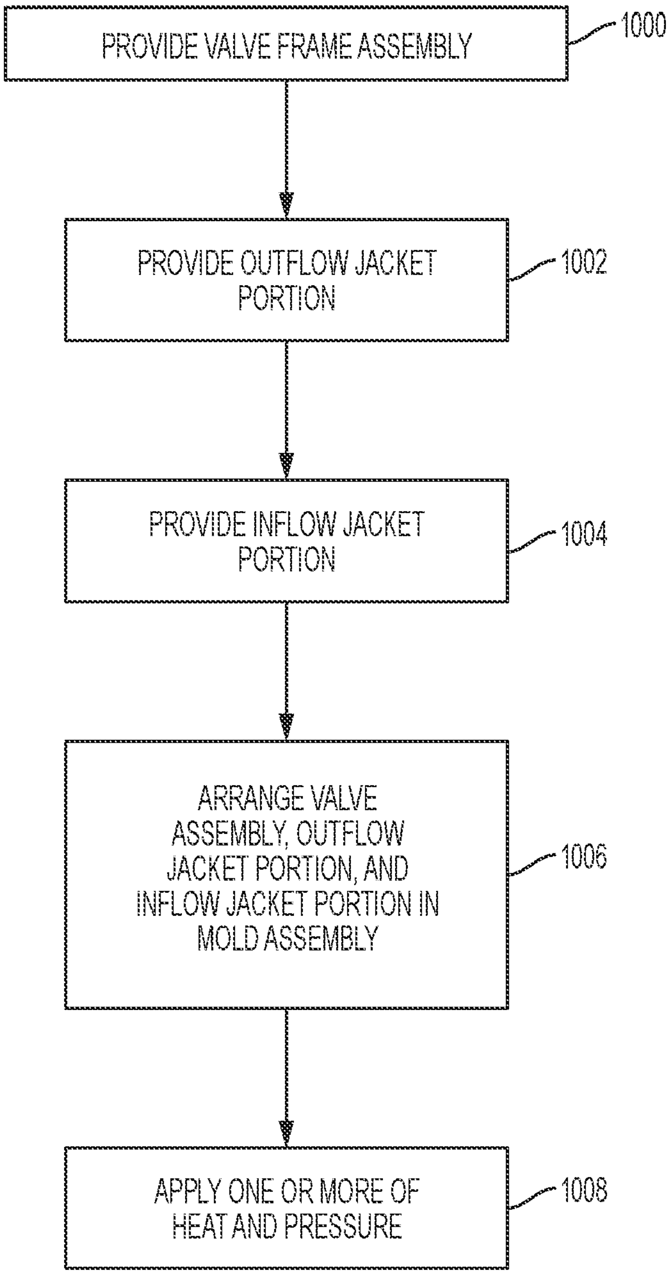
FIG. 11A is a flow chart of an example process for making a prosthetic valve, in accordance with an embodiment.
Figure 11B:
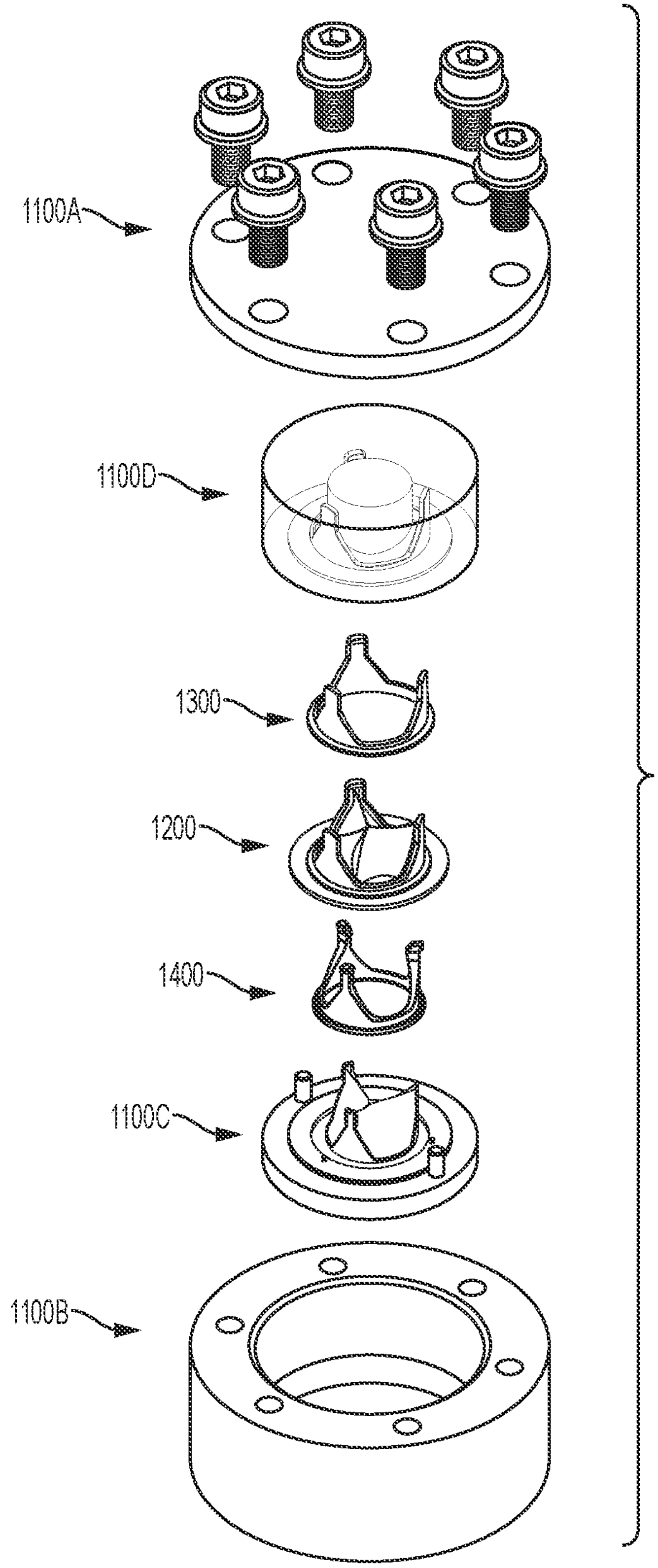
FIG. 11B is an exploded view of a mold assembly, in accordance with an embodiment.

Referring now to FIGS. 11A and 11B, an example molding process for forming a jacket about a valve assembly is shown and described. In some examples, the method includes providing a valve frame assembly, as shown in step 1000 of FIG. 11A. As mentioned above, in some examples, providing the valve frame assembly may include providing one or more of a valve frame, one or more leaflets, and a sewing cuff. As show in FIG. 11B, a valve frame assembly 1200 includes a valve frame, a plurality of leaflets, and a sewing cuff.

In some examples, the method further includes providing an outflow jacket portion (also referred to herein as a first portion of a jacket), as shown in step 1002 of FIG. 11A. The outflow jacket portion may include a polymeric material and may be pre-formed, such as to generally conform to or compliment a shape of the valve frame assembly. For example, as shown in FIG. 11B, an outflow jacket portion 1300 generally compliments a shaped of the valve frame assembly 1200. In some examples, the outflow jacket portion may be pre-formed and configured to change shape slightly during the molding process to adopt the desired final shape, based at least in part on a geometry of a molding assembly, as discussed further below and as those of skill in the art should appreciate.

In some examples, the method further includes providing an inflow jacket portion (also referred to herein as a second portion of a jacket), as shown in step 1004 of FIG. 11A. The inflow jacket portion may include a polymeric material and may be pre-formed, such as to generally conform to or compliment a shape of the valve frame assembly. For example, as shown in FIG. 11B, an inflow jacket portion 1400 generally compliments a shape of the valve frame assembly 1200. In some examples, the outflow jacket portion may be pre-formed and configured to change shape slightly during the molding process to adopt the desired final shape, based at least in part on a geometry of a molding assembly, as discussed further below and as those of skill in the art should appreciate.

In some examples, the method further includes arranging the valve frame assembly relative to the outflow and inflow jacket portions within a mold assembly, as shown in step 1006 of FIG. 11A. For example, arranging the valve frame assembly 1200 relative to the outflow and inflow jacket portions 1300 and 1400 may include situating the valve frame assembly 1200 between the outflow and inflow jacket portions 1300 and 1400, as shown in FIG. 11B. It is to be appreciated that the valve frame assembly 1200 and the outflow and inflow jacket portions 1300 and 1400 may be independently arranged within molding assembly (e.g., sequentially placed within a molding assembly), or the valve frame assembly 1200 and the inflow and outflow jacket portions 1300 may be arranged into an assembly, and the assembly may then be placed within the molding assembly.

The mold assembly may include a housing and one or more forming elements. For instance, as shown in FIG. 11B, the molding assembly includes a first housing element 1100A, a second housing element 1100B, a first forming element 1100C, and a second forming element 1100D. The first and second housing elements 1100A and 1100B are generally configured to withstand one or more of heat and pressure during the molding process, and thus may generally comprise any suitable size and shape conducive for accommodating the valve frame assembly 1200, the outflow and inflow jacket portions 1300 and 1400, and the first and second forming elements 1100C and 1100D. The first forming element 1100C is shown as including a geometry complementary of the valve frame assembly 1200 and the inflow jacket portion 1400. For example, as shown in FIG. 11B, the first forming element 1100C includes features (e.g., surfaces) configured to provide support to the leaflets of the valve frame assembly 1200 during the molding process. The first forming element 1100C may be formed of silicone. Other non-limiting examples for the forming element include Polyether ether ketone (PEEK), thermoplastics, thermosets, Stainless Steel, Inconel. These materials may thus be soft or rigid materials. More rigid materials provide that the jacket shape can be held constant, while allowing the second forming element 1100D to expand to provide molding/bonding pressure. Various other features of the first forming element 1100C are configured to accommodate and provide support for the valve frame assembly 1200 and the inflow jacket portion 1400, as will be apparent to those of skill in the art when referring to FIG. 11B.

Additionally, in some examples, the first forming element 1100C also includes a geometry that is complimentary of the desired size and shape of the inflow side of the formed prosthetic valve (e.g., the size and shape of the inflow side of the formed prosthetic valve after completion of the molding process). For instance, in some examples, the first forming element 1100C may include one or more features, profiles, or geometries corresponding with the desired final profile of the prosthetic valve not otherwise present in or defined by the preformed inflow jacket portion 1400. For example, the first forming element 1100C may include one or more fillets that are not present in or defined by the preformed inflow jacket portion 1400 (e.g., the preformed inflow jacket portion 1400 does not include any fillets). Thus, it is to be appreciated that, during the molding process, the first forming element 1100C operates to control or define a change in shape of the inflow jacket portion 1400 (e.g., during the molding process, the preformed inflow jacket portion 1400 changes shape slightly to define one or more fillets, the shape and size of which are controlled or defined by the first forming element 1100C).

The second forming element 1100D is shown as including a geometry complementary of the valve frame assembly 1200 and the outflow jacket portion 1300. For example, as shown in FIG. 11B, the second forming element 1100D includes features (e.g., surfaces) configured to provide support to the leaflets of the valve frame assembly 1200 during the molding process. The second forming element 1100D may be formed of silicone. Similar to first forming element 1100C, second forming element 1100D can be compliant or rigid, and may include the same materials discussed above with respect to first forming element 1100C. Silicone, for example, expands during heating thereby providing molding/bonding pressure during the manufacturing process. Various other features of the second forming element 1100D are configured to accommodate and provide support for the valve frame assembly 1200 and the outflow jacket portion 1300, as will be apparent to those of skill in the art when referring to FIG. 11B.

Additionally, in some examples, the second forming element 1100D also includes a geometry that is complimentary of the desired size and shape of the outflow side of the formed prosthetic valve (e.g., the size and shape of the outflow side of the formed prosthetic valve after completion of the molding process). For instance, in some examples, the second forming element 1100D may include one or more features, profiles, or geometries corresponding with the desired final profile of the prosthetic valve not otherwise present in or defined by the preformed outflow jacket portion 1300. For example, the second forming element 1100D may include one or more fillets that are not present in or defined by the preformed outflow jacket portion 1300 (e.g., the preformed outflow jacket portion 1300 does not include any fillets). Thus, it is to be appreciated that, during the molding process, the second forming element 1100D operates to control or define a change in shape of the outflow jacket portion 1300 (e.g., during the molding process, the preformed outflow jacket portion 1300 changes shape slightly to define one or more fillets, the shape and size of which are controlled or defined by the second forming element 1100D).

In some examples, the method further includes applying one or more of heat and pressure to the molding assembly, as shown in step 1108 of FIG. 11A Though the method of making a prosthetic valve discussed above includes providing preformed outflow and inflow jacket portions 1300 and 1400 in combination with the valve frame assembly 1200, it is to be appreciated that the valve frame assembly (e.g., valve frame assembly 1200 may be provided within a mold assembly without preformed outflow and/or inflow jacket portions, and the jacket material may be injected into the mold assembly under one or more of heat and pressure to form the prosthetic valve (e.g., an injection molding process).

The inventive concepts of this application have been described above both generically and with regard to specific embodiments. It will be apparent to those skilled in the art that various modifications and variations can be made in the embodiments without departing from the scope of the disclosure. Thus, it is intended that the embodiments cover the modifications and variations of the inventive concepts provided they come within the scope of the appended claims and their equivalents.

What is claimed is:

1. A covering for a prosthetic valve, the covering comprising:

a first portion configured to couple to an outflow side of the prosthetic valve, the first portion being annular in shape and having a first edge alternating between one or more first tips and one or more first valleys; and a second portion configured to couple to an inflow side of the prosthetic valve, the second portion being annular in shape and having a second edge alternating between one or more second tips and one or more second valleys, wherein the one or more second tips are configured to couple to the one or more first tips to at least partially cover posts of the prosthetic valve, wherein the one or more second tips have a tapered form, wherein the one or more second tips form free ends, and wherein the one or more second tips increase in width towards the free ends.

2. The covering of claim 1, wherein the one or more first tips and the one or more second tips are configured to be coupled together by at least one of a swaging, a snap fit, a click fit, one or more staples, tape, adhesives, one or more screws, one or more rivets, insert molding, or overmolding.

3. The covering of claim 1, wherein the first portion comprises three first tips.

4. The covering of claim 1, wherein the one or more first tips are atraumatic.

5. The covering of claim 1, wherein the one or more first tips include first interfaces and the one or more second tips include second interfaces, the first and second interfaces being configured to join the first and second portions together.

6. The covering of claim 5, wherein the first interfaces and the second interfaces are operable to snap together to join the first portion to the second portion.

7. The covering of claim 1, wherein the first portion includes a flange element projecting at least partially radially outward.

8. The covering of claim 7, wherein the one or more first tips include at least two or more tips, and wherein the flange element extends between tips of the two or more tips of the first portion.

9. The covering of claim 1, wherein the first portion is formed of a more flexible material relative to a material of the second portion.

10. A covering for a prosthetic valve, the covering comprising:

a first portion configured to couple to an outflow side of the prosthetic valve, the first portion being annular in shape and having a first edge alternating between one or more first tips and one or more first valleys; and a second portion configured to couple to an inflow side of the prosthetic valve, the second portion being annular in shape and having a second edge alternating between one or more second tips and one or more second valleys, wherein the one or more second tips are configured to couple to the one or more first tips to at least partially cover posts of the prosthetic valve, wherein the one or more second tips have a tapered form, wherein the first portion and the second portion are configured to be coupled together about a frame of the prosthetic valve, and wherein the first portion is configured to couple to the second portion at an interface between a sewing cuff and the frame of the prosthetic valve.

11. The covering of claim 10, wherein the one or more first tips and the one or more second tips are configured to be coupled together by at least one of a swaging, a snap fit, a click fit, one or more staples, tape, adhesives, one or more screws, one or more rivets, insert molding, or overmolding.

12. The covering of claim 10, wherein the one or more second tips form free ends, and wherein the one or more second tips increase in width towards the free ends.

13. The covering of claim 10, wherein the first portion includes a fillet operable to limit tissue ingrowth beyond the fillet.

14. A covering for a prosthetic valve, the covering comprising:

a first portion configured to couple to an outflow side of the prosthetic valve, the first portion being annular in shape and having a first edge alternating between one or more first tips and one or more first valleys; and a second portion configured to couple to an inflow side of the prosthetic valve, the second portion being annular in shape and having a second edge alternating between one or more second tips and one or more second valleys, wherein the one or more second tips are configured to couple to the one or more first tips to at least partially cover posts of the prosthetic valve, wherein the one or more second tips have a tapered form, and wherein the first portion includes a fillet operable to limit tissue ingrowth beyond the fillet.

15. The covering of claim 14, wherein the one or more first tips and the one or more second tips are configured to be coupled together by at least one of a swaging, a snap fit, a click fit, one or more staples, tape, adhesives, one or more screws, one or more rivets, insert molding, or overmolding.

16. The covering of claim 14, wherein the one or more second tips form free ends, and wherein the one or more second tips increase in width towards the free ends.

* * * * *